(12) United States Patent
Coleman et al.

(10) Patent No.: US 7,750,180 B2
(45) Date of Patent: Jul. 6, 2010

(54) PROCESS FOR THE PREPARATION OF N-PHOSPHONOMETHYLGLYCINE AND DERIVATIVES THEREOF

(75) Inventors: James P. Coleman, Maryland Heights, MO (US); Jerry R. Ebner, St. Louis, MO (US); Eric A. Haupfear, O'Fallon, MO (US); Patrick J. Lennon, St. Louis, MO (US); Joseph A. Schaper, St. Louis, MO (US); Samuel J. Tremont, Manchester, MO (US); Serge G. Wolfson, Chesterfield, MO (US); Philip H. Brodsky, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 811 days.

(21) Appl. No.: 10/924,265

(22) Filed: Aug. 23, 2004

(65) Prior Publication Data
US 2005/0054871 A1   Mar. 10, 2005

Related U.S. Application Data

(60) Provisional application No. 60/497,288, filed on Aug. 22, 2003.

(51) Int. Cl.
*C07F 9/22* (2006.01)
(52) U.S. Cl. ............................................. 562/17; 562/22
(58) Field of Classification Search .................. 562/22, 562/17
See application file for complete search history.

(56) References Cited

U.S. PATENT DOCUMENTS

| | | | |
|---|---|---|---|
| 2,328,358 | A | 8/1943 | Pikl |
| 3,799,758 | A | 3/1974 | Franz |
| 3,977,860 | A * | 8/1976 | Franz ........................ 504/206 |
| 4,369,142 | A | 1/1983 | Moser |
| 4,661,298 | A | 4/1987 | Mirviss et al. |
| 4,810,426 | A | 3/1989 | Fields, Jr. et al. |
| 5,627,125 | A | 5/1997 | Ebner et al. |
| 5,689,000 | A | 11/1997 | Ebner et al. |
| 6,005,140 | A | 12/1999 | Morgenstern et al. |
| 6,232,494 | B1 | 5/2001 | Morgenstern et al. |

FOREIGN PATENT DOCUMENTS

| | | |
|---|---|---|
| DE | 2 528 633 A1 | 2/1976 |
| DE | 2 741 504 A | 3/1979 |
| EP | 0 139 140 A1 | 5/1985 |
| FR | 2 276 312 | 1/1976 |
| FR | 2 568 882 A1 | 2/1986 |
| GB | 1 147 179 | 4/1969 |
| SU | 547451 A | 7/1977 |

| | | |
|---|---|---|
| WO | WO 95/00523 A1 | 1/1995 |

OTHER PUBLICATIONS

Avila, et al., "Chemical and Mutagenic Analysis of Aminomethylphosphonate Biodegradation," *J. Am. Chem. Soc.*, 1987, pp. 6758-6764, vol. 109, No. 22.

Cameron, et al., "Organophosphorus Compounds as Potential Fungicides. Part 1. (N-(w-Guanidinoalkyl) Aminoalkanephosphonic Acids and Their Aminophosphonic Precursors: Preparation, NMR Spectroscopy, and Fast Atom Bombardment Mass Spectrometry ," *Phosphorus and Sulfur*, 1988, pp. 183-197, vol. 40, United Kingdom.

Du, et al., "Synthesis and Evaluation of Putative Oxocarbenium Intermediate Mimic in the KDO8P Synthase-Catalyzed Reaction as a Tool for the Design of Potent Inhibitors for Lipopolysaccharide Biosynthesis," *Bioorganic & Medicinal Chemistry Letters*, 1997 pp. 2469-2472, vol. 7, No. 19, Great Britain.

Hudson, et al., "An Approach to the Development of Organophosphorus Fungicides," *Phosphorus, Sulfur, and Silicon*, 1996, pp. 345-348, vols. 109-110, Netherlands.

Lombaert, et al., "N-Phosphonomethyl Dipeptides and Their Phosphonate Prodrugs, a New Generation of Neutral Endopeptidase (NEP, EC 3.4.24.11) Inhibitors," *J. Med. Chem.*, 1994, pp. 498-511, vol. 37, No. 4.

(Continued)

*Primary Examiner*—Jafar Parsa
(74) *Attorney, Agent, or Firm*—Senniger Powers LLP; Joseph A. Schaper

(57) ABSTRACT

N-phosphonomethylamines are produced by reaction of an amine substrate with a halomethylphosphonic acid or salt thereof, a hydroxymethylphosphonic acid or salt thereof, or a dehydrated self-ester dimer, trimer or oligomer of hydroxymethylphosphonic acid. Among the products that may be prepared according to the process are N-phosphonomethylaminocarboxylic acids such as (e.g.) glyphosate, N-phosphonomethylaminoalkanols such as (e.g.) hydroxyethlaminomethylphosphonic acid, and N-acylaminomethylphosphonic acids such as (e.g.) N-carbamylaminomethylphosphonic acid. Certain reactions are conducted with a substantial excess of amine reactant in order to drive the conversion while avoiding excessive formation of bis(N-phosphonomethyl)amine by-products. Other reactions use a secondary amine substrate (such as iminodiacetic acid) and can be conducted at substantial equimolar ratios of halomethylaminomethylphosphonic acid or hydroxyaminomethylphosphonic acid to secondary amine reactant without significant formation of bis(phosphonomethyl)amine by-products. Further disclosed is a process for the preparation of hydroxymethylphosphonic acid self-ester dimers, trimers and oligomers by azeotropic dehydration.

39 Claims, 6 Drawing Sheets

OTHER PUBLICATIONS

Figure 1:
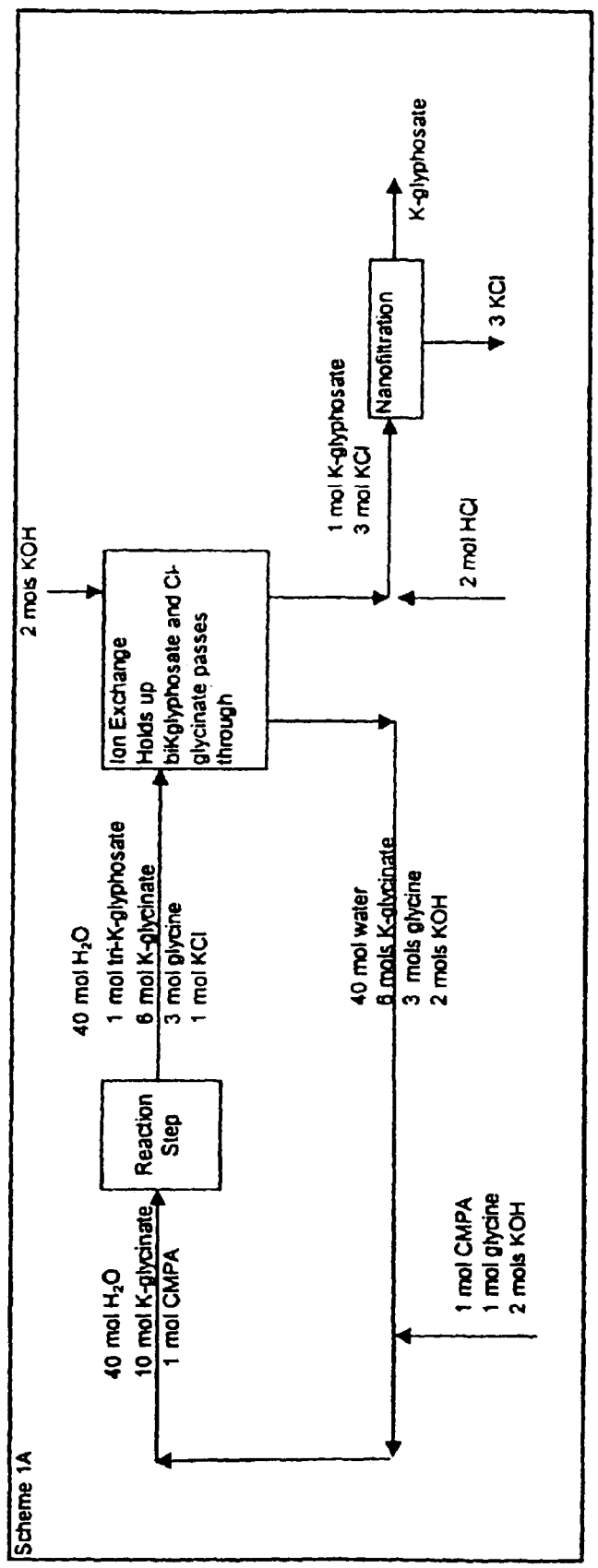

Maier, Ludwig, "Organic Phosphorus Compounds 98. Synthesis and Properties of N-Methylaminomethylphosphonic Acid and Derivatives," *Phosphorus, Sulfur and Silicon*, 1991, pp. 29-34, vol. 62, United Kingdom.

Storz, et al., "N-Monoalkylation of Tetra-O-benzyl-D-arabinonamide: Synthesis of Some Open-Chain Analogues of N-Acetylneuraminic Acid and Their Evaluation as Sialidase Inhibitors," *Helvetica Chimica Acta*, 1998, pp. 1896-1907, vol. 81, No. 10.

Wallace, et al., "Design and Synthesis of Potent, Selective Inhibitors of Endothelin-Converting Enzyme," *J. Med. Chem.*, 1998, pp. 1513-1523, vol. 41, No. 9.

International Search Report, PCT/US2004/027413, from the European Patent Office dated May 12, 2005 (3 pages).

Partial International Search Report, PCT/US2004/027413, from the European Patent Office dated Mar. 7, 2005 (3 pages).

Franz, J. et al., "Glyphosate: A Unique Global Herbicide," American Chemical Society, 1997, pp. 233-262, Washington, DC.

Fredericks, P. et al., "Synthesis and Biological Activity of Aminomethylphosphonic Acids Related to the Herbicide Glyphosate," Zeitschrift für Naturforschung, 1981, pp. 242-245, vol. 36c, No. 3/4.

Griffiths, W., et al., "The Reaction of Phosophorus Trichloride and Paraformaldehyde: Hydroxymethane and Chloromethane Phosphonyl Compounds," Phosphorus, 1976, pp. 223-230, vol. 6, Gordon and Breach Science Publishers Ltd., Great Britain.

Liu, P., "Determination of Chloride Ions In Intermediate and End Product in Glyphosate Nanlin Z Process," Journal of Nanjing Institute of Forestry, 1984, pp. 33-39, vol. 3, Kai hsüeh yüan, China.

Petrov, K. et al., "Reactions in the Dibenzylphosphine Oxide-Formaldahyde-Aniline System; replacement of the hydroxyl group in hydroxymethyiphosphonic acid by amino groups," Khim. Elementorg. Soed., 1976, pp. 200-204, "Nauka", Leningr. Otd., Leningrad, USSR.

Xiba, H. et al., "A Comprehensive Study on the Preparation of Glyphosate "Nanlin Z" by Chloromethylphosphonic Acid Process Under Pressure on Pilot Plant Scale," Department of Chemical Processing of Forest Products, 1984, pp. 43-59, vol. 1, Nanjing, Peoples Republic of China.

* cited by examiner

PROCESS FOR THE PREPARATION OF N-PHOSPHONOMETHYLGLYCINE AND DERIVATIVES THEREOF

This invention relates to the preparation of N-(phosphonmethyl)glycine and derivatives thereof, and more particularly to an improved process for the preparation of such com.1pounds based on reactions of a halomethylphosphonic acid.

N-(phosphonomethyl)glycine, also known by its common name glyphosate, is a highly effective and commercially important herbicide useful for combating the presence of a wide variety of unwanted vegetation, including agricultural weeds. Between 1988 and 1991, approximately 13 to 20 million acres per year worldwide were treated with glyphosate, making it one of the most important herbicides in the world. Substantial growth in the manufacture and use of glyphosate has continued throughout the 1990s and the market has continued to be strong in the early 2000s. Convenient and economical methods of preparing glyphosate and other amino carboxylic acids are, therefore, of major commercial importance.

Franz, et al. in *Glyphosate: A Unique Global Herbicide* (ACS Monograph 189, 1997) at p. 233-257 identify a number of routes by which glyphosate can be prepared. According to one of these, iminodiacetic acid disodium salt (DSIDA) is treated with formaldehyde and phosphorous acid or phosphorous trichloride to produce N-(phosphonomethyl)-iminodiacetic acid and sodium chloride. A carboxymethyl group on the N-(phosphonomethyl)iminodiacetic acid is then oxidatively cleaved in the presence of a carbon catalyst to produce glyphosate acid. Oxidation produces by-products that are not readily recovered, compromising yields on basic raw materials, and creating waste disposal requirements. For example, DSIDA may be produced by oxidation of diethanolamine, which in turn is produced from ethylene oxide and ammonia. In glyphosate synthesis based on IDA or DSIDA, yields on ethylene oxide are 50% or lower.

Processes are known for the preparation of glyphosate by reaction of chloromethylphosphonic acid with glycine. For example, U.S. Pat. No. 4,661,298 describes the reaction between chloromethylphosphonic acid ("CMPA") and glycine in an aqueous alkaline medium (3.6 equivalents of NaOH per equivalent CMPA) either without catalyst or in the presence of polyethyleneimine at a ratio of 1:1 CMPA:glycine. Under these conditions in the absence of catalyst, the highest yield of glyphosate was 40.4% (with glyphosine as the major side-product, 43.3%). In the presence of polyethyleneimine the yield of glyphosate increased to 57.6% (with glyphosine as a side-product). German Patent No. DE 2528633 (1976), CA 85:21610, and a Chinese paper (J. Nanjing Institute of Forestry #1, 1984, pp. 43-59, CA 101:213023, 102:1868) also each describe the reaction of CMPA and glycine where the yield of glyphosate was claimed 85 to 95% for a ratio of 1:1 CMPA:Glycine, but analytical corroboration (e.g., by HPLC or NMR) was not reported. U.S. Pat. No. 3,977,860 (1976) reported glyphosate preparation from a weight ratio of 2:1 CMPA:glycine without reporting the yield. Generally, yields of glyphosate based on chloromethylphosphonic acid have been rather poor, largely due to the formation of glyphosine or other N,N-bis(phosphonomethyl) species.

SUMMARY OF THE INVENTION

Among the several objects of the present invention, therefore, may be noted the provision of a process for the preparation of glyphosate; the provision of a process for the preparation of a precursor of glyphosate; the preparation of such processes which produce glyphosate or a glyphosate precursor without producing stoichiometric equivalents of carbonaceous by-products; the provision of processes which are based on halomethylphosphonic acid; the provision of processes based on halomethylphosphonic acid which achieve relatively high yields of glyphosate or glyphosate precursor; and the provision of processes which achieve high conversions of halomethylphosphonic acid without excessive formation of glyphosine or other N,N-bis(phosphonomethyl) species. A further object of the invention is to provide processes for the preparation of glyphosate or glyphosate salt based on hydroxymethyl-phosphoric acid or a source thereof.

Other objects will be in part apparent and in part pointed out hereafter.

Briefly therefore, the present invention is directed a process for preparing a product corresponding to the formula:

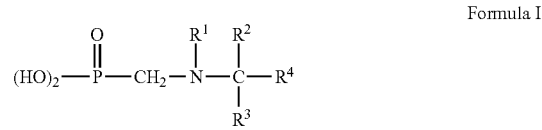

Formula I or a phosphonic acid ester or salt thereof. $R^1$ is selected from the group consisting of hydrogen and substituted or unsubstituted alkyl, alkenyl, alkynyl, aryl, aralkyl, aralkenyl or aralkynyl. $R^2$ and $R^3$ are independently selected from the group consisting of hydrogen, nitro, cyano and substituted or unsubstituted alkyl, alkenyl, alkynyl, aryl, aralkyl, aralkenyl or aralkynyl and $R^4$ is selected from the group consisting of cyano and a substituent corresponding to the formula:

Formula II wherein $R^5$ is hydrogen or a moiety forming a carboxylate salt or ester. The process comprises contacting a halomethylphosphonic acid or a salt thereof with an amine reactant comprising a compound corresponding to the formula:

Formula III wherein $R^1$, $R^2$, $R^3$ and $R^4$ are as defined above, or a dimer, oligomer or polymer of a compound of Formula III in which $R^4$ corresponds to Formula II, in a ratio of least about 1.5 moles of said amine reactant per mole halomethylphosphonic acid.

The invention is also directed to a process for preparing a product corresponding to Formula I, as described above, comprising contacting a halomethylphosphonic acid or a salt thereof with an amine reactant comprising a compound corresponding to Formula III, as described above, in a condensed phase alkaline reaction medium containing a cation selected from the group consisting of tetraalkylammonium and substituted phosphonium, sulfonium or sulfoxonium, and mixtures thereof.

The invention is also directed to a process for the preparation of a product corresponding to the formula:

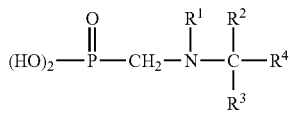

Formula I or a phosphonic acid ester or salt thereof. $R^1$ is selected from the group consisting of substituted or unsubstituted alkyl, alkenyl, alkynyl, aryl, aralkyl, aralkenyl or aralkynyl. $R^2$ and $R^3$ are independently selected from the group consisting of hydrogen, nitro, cyano and substituted or unsubstituted alkyl, alkenyl, alkynyl, aryl, aralkyl, aralkenyl or aralkynyl. $R^4$ is selected from the group consisting of cyano and a substituent corresponding to the formula:

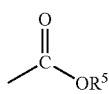

Formula II wherein $R^5$ is hydrogen or a moiety forming a carboxylate salt or ester. The process comprises contacting a halomethylphosphonic acid reactant with an amine reactant, said halomethylphosphonic acid reactant comprising halomethylphosphonic acid, a halomethylphosphonic acid salt halomethylphosphonic acid ester, or mixtures thereof, said amine reactant comprising a compound corresponding to the formula:

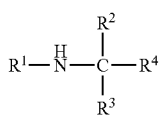

Formula III wherein $R^1$, $R^2$, $R^3$ and $R^4$ are as defined above, or a dimer, oligomer or polymer of a compound of Formula III in which $R^4$ corresponds to Formula II.

The invention is further directed to a process for the preparation of a product corresponding to the formula:

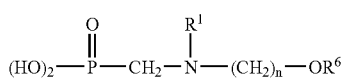

Formula IV or a phosphonic acid ester or salt thereof. $R^1$ is selected from the group consisting of hydrogen and substituted or unsubstituted alkyl, alkenyl, alkynyl, aryl, aralkyl, aralkenyl or aralkynyl. $R^6$ is hydrogen or an ether forming moiety, and $R^7$ is selected from the group consisting of alkylene and alkenylene. The process comprising contacting a halomethylphosphonic acid or a salt thereof with an amine reactant comprising an amino alcohol or source thereof. Said reactant comprising a compound corresponding to the formula:

Formula V wherein $R^1$, $R^6$ and $R^7$ are as defined above.

The invention is further directed to a process for the preparation of a product selected from the group consisting of hydroxyethylaminomethylphosphonic acid, an N-alkylhydroxyethylaminomethylphosphonic, a salt or ester of hydroxyethylaminomethylphosphonic acid, or a salt or ester of an N-alkylhydroxyethylaminomethylphosphonic. The process comprises contacting a halomethylphosphonic acid or a salt thereof with an amino alcohol source selected from the group consisting of ethanolamine, an N-alkylethanolamine, an ether of ethanolamine, or an ether of an N-alkylethanolamine.

The invention is further directed to a process for the preparation of triphosphonomethylamine comprising contacting an ammonia source with a halomethylphosphonic acid.

The invention is still further directed to a process for the preparation of an alkali metal salt of glyphosate. The process comprises the following steps:

contacting halomethylphosphonic acid or a salt thereof with a stoichiometric excess of glycine, a glycinate salt, N-substituted glycine or N-substituted glycinate salt to produce a reaction mixture comprising an alkali metal glycinate or N-substituted glycinate and a trialkali metal salt of glyphosate;

partially neutralizing a product recovery feed mixture, said product recovery feed mixture comprising glyphosate or a glyphosate salt produced in said reaction mixture and unreacted glycine, glycinate salt, N-substituted glycine or N-substituted glycinate salt, thereby converting alkali metal glycinate or N-substituted glycinate contained therein to glycine or N-substituted glycine; and, crystallizing glycine or N-substituted glycine from the acidified reaction mixture.

The invention is still further directed to a process for the preparation of an alkali metal salt of glyphosate. The process comprises the following steps:

contacting a halomethylphosphonic acid or salt thereof with a stoichiometric excess of glycine, glycinate salt, N-substituted glycine or N-substituted glycinate salt to produce a reaction mixture comprising a trialkali metal salt of glyphosate and an unreacted amine constituent selected from the group consisting of glycine, an alkali metal glycinate, N-substituted glycine, or an N-substituted glycinate;

contacting a product recovery feed mixture with an ion exchange resin selective for glyphosate versus said unreacted amine constituents, said product recovery feed mixture comprising glyphosate or glyphosate salt produced in said reaction mixture and an unreacted amine constituent, thereby loading an anion of glyphosate onto said resin and producing an effluent phase containing said unreacted amino acid constituent; and contacting the ion exchange resin bearing said glyphosate anion with a base, thereby eluting a glyphosate salt from said resin and producing an aqueous eluate comprising said glyphosate salt and a halide salt of said base.

The invention is further directed to a process for the preparation of a product corresponding to the formula:

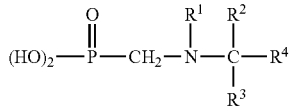

Formula I or a phosphonic acid ester or salt thereof, wherein $R^1$ is selected from the group consisting of hydrogen and substituted or unsubstituted alkyl, alkenyl, alkynyl, aryl, aralkyl, aralkenyl or aralkynyl, $R^2$ and $R^3$ are independently selected from the group consisting of hydrogen, nitro, cyano and substituted or unsubstituted alkyl, alkenyl, alkynyl, aryl, aralkyl, aralkenyl or aralkynyl, and $R^4$ is selected from the group consisting of cyano and a substituent corresponding to the formula:

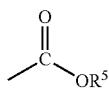

Formula II wherein $R^5$ is hydrogen or a moiety forming a carboxylate salt or ester. In the process, hydroxymethylphosphonic acid, salt thereof or a source thereof is contacted with an amine reactant comprising a compound corresponding to the formula:

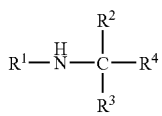

Formula III wherein $R^1$, $R^2$, $R^3$ and $R^4$ are as defined above, or a dimer, oligomer or polymer of a compound of Formula III in which $R^4$ corresponds to Formula II, in a ratio of least about 1.5 moles of said amine reactant per mole halomethylphosphonic acid.

The invention also comprises a process for producing a substantially anhydrous dimeric, trimeric or oligomeric self ester of hydroxymethylphosphonic acid. Hydroxymethylphosphonic acid is heated at a temperature between about 100° and about 200° C. and a pressure between about 1 and about 70 mm Hg in the presence of an organic solvent. The organic solvent is characterized by forming an azeotrope with water at a temperature between about 100° and about 170° C.

The invention is also directed toga process for the preparation of a product corresponding to the formula:

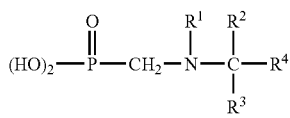

Formula IV or a phosphonic acid ester or salt thereof, wherein $R^1$ is selected from the group consisting of hydrogen and substituted or unsubstituted alkyl, alkenyl, alkynyl, aryl, aralkyl, aralkenyl or aralkynyl, $R^6$ is hydrogen or an ether forming moiety, and $R^7$ is selected from the group consisting of alkylene and alkenylene. In the process, hydroxymethylphosphonic acid, a salt thereof, or a source thereof, is contacted with an amine reactant comprising an amino alcohol or source thereof. The amine reactant comprises a compound corresponding to the formula:

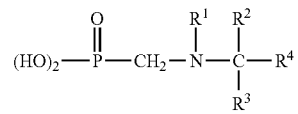

Formula V wherein $R^1$, $R^6$ and $R^7$ are as defined above.

The invention also comprises a process for the preparation of aminomethylphosphonic acid or derivative thereof. In the process, hydroxymethylphosphonic acid, a salt thereof or a source thereof is contacted with an amide, thereby forming an N-acylaminomethylphosphonic acid intermediate. The intermediate is hydrolyzed to produce aminomethylphosphonic acid or a derivative thereof.

DESCRIPTION OF THE PREFERRED EMBODIMENTS

In accordance with the present invention, it has been discovered that favorable yields of glyphosate or another monophosphonomethyl glyphosate derivative can be achieved by reaction of a halomethylphosphonic acid reactant with glycine, a glycine salt, an N-substituted glycine, or salt of an N-substituted glycine. The halomethylphosphonic acid reactant comprises a halomethylphosphonic acid such as chloromethylphosphonic acid, bromomethylphosphonic acid, iodomethylphosphonic acid, a salt thereof or an ester thereof.

In a preferred embodiment of the invention, a halomethylphosphonic acid reactant is reacted with a substituted or unsubstituted glycine or alkali metal glycinate substrate, in a ratio of at least about 1.5 moles of the substrate per mole of the total of halomethylphosphonic acid reactants. The process of the invention is applicable to the preparation of esters of glyphosate, and especially to the preparation of glyphosate salts.

Further in accordance with the invention, hydroxyethylaminomethylphosphonic acid (HEAMPA), an ester thereof or a salt thereof, may be prepared by reaction of monoethanolamine (MEA) with a halomethylphosphonic acid reactant. HEAMPA is a valuable intermediate for the preparation of glyphosate, glyphosate salts and glyphosate esters. The process is also effective for the preparation of various derivatives of glyphosate and HEAMPA based on the use of substrates which are derivatives of glycine or monoethanolamine.

Further in accordance with the invention, triphosphonomethylamine may be prepared by reaction of a halomethylphosphonic acid reactant with an ammonia source. Triphosphonomethylamine is a useful sequestrant, as well as a precursor to glyphosate.

Reactions of Glycine and Glycine Derivatives

More generally, a compound corresponding to the formula:

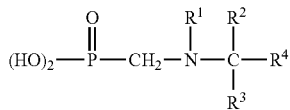

Formula I or a salt or phosphonic acid ester thereof, can be produced by contacting a halomethylphosphonic acid with a compound of Formula III:

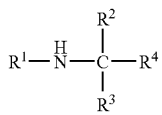

Formula III

In the compounds of Formulae I and III, $R^1$ is hydrogen or substituted or unsubstituted alkyl, alkenyl, alkynyl, aryl, aralkyl, aralkenyl or aralkynyl, $R^2$ and $R^3$ are independently hydrogen, nitro, cyano or substituted or unsubstituted alkyl, alkenyl, alkynyl, aryl, aralkyl, aralkenyl or aralkynyl and $R^4$ is cyano or a substituent corresponding to the formula:

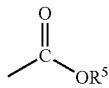

Formula II wherein $R^5$ is hydrogen or a moiety forming a carboxylate salt or ester. For example, $R^5$ may be selected from among hydrogen, alkali metal, substituted ammonium, sulfonium, phosphonium, or sulfoxonium, or substituted or unsubstituted alkyl, alkenyl, alkynyl, aryl, aralkyl, aralkenyl or aralkynyl. Among the substituted alkyl groups which may constitute $R^1$ are hydroxycarbonylmethyl (carboxy methyl), alkoxycarbonylmethyl, and a carboxymethyl anion, i.e., where the compound of formula I and/or III is a carboxylate salt.

In addition to hydrogen, typical substituents which may constitute $R^1$, $R^2$ and/or $R^3$ include methyl, ethyl, n-propyl, isopropyl, n-butyl, isobutyl, pentyl, hexyl, octyl, decyl, vinyl, allyl, pentenyl, ethynyl, butynyl, benzyl, phenylethyl, phenylvinyl, phenylallyl, p-methylphenylethyl, phenylethynyl and the like. These same groups may serve as ester-forming moieties of the substituents which can constitute $R^4$. $R^5$ may comprise any of the same species, but may alternatively be sodium, potassium, ammonium, isopropylammonium, tetramethylammonium or other tetraalkylammonium, benzyltriethylammonium or other benzyltrialkylammonium, trialkylsulfonium, and comparably substituted phosphonium and sulfoxonium salts.

Where $R^1$ is other than hydrogen, the compounds of Formulas I and III are "N-substituted" compounds. Several methods for the preparation of N-substituted glycines and their salts and amides comprised by Formula III are provided by U.S. Pat. No. 6,005,140 (1999) and U.S. Pat. No. 6,232,494 (2001), which are expressly incorporated herein by reference in their entirety. For example, N-substituted glycine may be prepared: 1) by the condensation of hydrogen cyanide, formaldehyde, and N-substituted amines, followed by hydrolysis to N-substituted glycine or a salt thereof; 2) by the reductive alkylation of glycine achieved by reacting carbonyl compounds with glycine and hydrogen in the presence of a catalyst; 3) by condensation (carboxymethylation) of N-substituted amides, formaldehyde, and carbon monoxide in the presence of a catalyst to produce N-acetyl of the N-substituted glycine which may be hydrolyzed to the N-substituted glycine; and 4) by dehydrogenation of N-substituted ethanolamine in the presence of a base (preferably sodium hydroxide) to form salts of N-substituted glycines, described by Ebner et al. in U.S. Pat. No. 5,627,125, expressly incorporated herein by reference in its entirety. The N-substituted ethanolamine precursor may be prepared in at least two ways. First, ketones may be condensed with monoethanolamine in the presence of hydrogen, a solvent, and a noble metal catalyst. N-substituted ethanolamines also may be prepared by reacting a mono-substituted amine (such as methylamine) with ethylene oxide to form the mono-substituted ethanolamine.

Alternatively to reaction with a compound of Formula III, a halomethylphosphonic acid may be reacted with a dimer, oligomer or polymer of the compound of Formula III wherein $R^4$ corresponds to Formula II.

The reaction between halomethylphosphonic acid and a monomer of Formula III proceeds in the following manner:

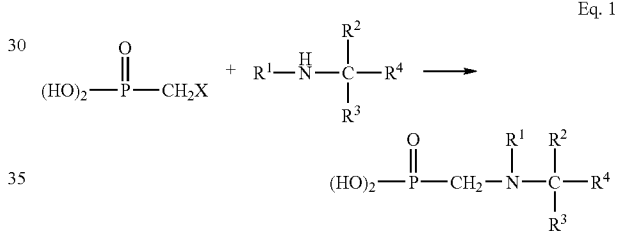

Eq. 1 where X is halogen, preferably Cl, Br or I, most preferably Cl. Preferably, the reactants are charged to a reaction zone in a ratio of moles of the glycine or glycinate substrate per mole halomethylphosphonic acid of at least about 3, more preferably at least about 5, most preferably at least about 8. Operation at a high ratio of substrate to halomethylphosphonic acid has been found to provide high conversion of halomethylphosphonic with minimal formation of glyphosine or other N,N-bis(phosphonomethyl) species. Thus, high yields of glyphosate or glyphosate derivative based on halomethylphosphonic acid are achieved. Moreover, unreacted glycine or glycinate can be recovered from the reaction mixture and recycled, providing ultimately high yields on the substrate as well.

Reaction at lower ratios of substrate to halomethylphosphonic acid is available in the reaction of halomethylphosphonic acid with N-substituted glycine or N-substituted glycinate substrate, i.e. a compound according to Formula III wherein $R^1$ is other than hydrogen. High conversion of halomethylphosphonic with minimal formation of glyphosine or other N,N-bis(phosphonomethyl) species and high yields of N-substituted glyphosate or glyphosate derivative based on halomethylphosphonic acid are achieved at ratios of 3 or lower. Preferably the reactants are charged to a reaction zone with substantially molar equivalents of N-substituted glycine or N-substituted glycinate substrate and halomethylphosphonic acid. Thereby the amount of unreacted N-substituted glycine or N-substituted glycinate substrate may be minimized or eliminated, advantageously reducing reactant recycle and reducing the load on post-reaction separation processes.

Preferably, $R^1$ in Formulae I and III is hydrogen or alkyl, most typically hydrogen, methyl, isopropyl, or hydroxycarbonyl methyl. $R^4$ preferably corresponds to Formula II, and $R^5$ is hydrogen, alkali metal, isopropylammonium, or dimethylsulfonium. Most preferably, the compound of Formula III is glycine (or its hydrochloride), an alkali metal glycinate, iminodiacetic acid (or its hydrochloride) or an alkali metal salt of iminodiacetic acid such as disodium iminodiacetic acid. The principal commercial application of the process is in the preparation of glyphosate acid or glyphosate salt herbicidal applications.

Reaction is preferably carried out in a medium comprising a polar solvent, most preferably water or a mixture of water and a water-miscible organic solvent such as a primary alcohol, glycol, dioxane, or tetrahydrofuran. Polar organic solvents such as dimethylformamide, glycols, glycol ethers, acetonitrile, and crown ethers can sometimes be used in an anhydrous system, but alkali metal glycinates have low solubilities in solvents other than water. Tetraalkylammonium glycine may have a higher solubility in polar organic solvents, and even reaction in suspension may be feasible. However, the presence of water is preferred to provide favorable selectivity to glyphosate or other compound of Formula I rather than glyphosine or other bis(phosphonomethyl) species. Water or a mixture of water and a water-miscible solvent provides further advantages that are discussed below.

The reaction medium is also preferably alkaline. If the amine substrate comprises an alkali metal salt of an amino acid, e.g., sodium glycinate, the reaction may proceed effectively in the absence of any other base. However, in addition to the amino acid carboxylate salt, another base is preferably present in the reaction medium, most preferably an alkali metal hydroxide such as NaOH or KOH. It has been found that the reaction can be driven to completion at modest ratios of the total base charge to the total halomethylphosphonic acid reactant charge. For example, where the amine reactant is alkali metal glycinate, only a modest excess of additional base, e.g., between about 0.01 and about 3.5 moles alkali metal hydroxide per mole of halomethylphosphonic acid, is required to drive the reaction to high conversion. Alternatively or additionally, other bases can be present in addition to, or in lieu of an alkali metal hydroxide such as, for example, alkaline phosphate salts and hydroxides of countercations such as substituted ammonium, phosphonium, sulfonium or sulfoxonium, and mixtures thereof.

Promotion of the reaction by use of KOH as the base is particularly advantageous where the ultimately desired herbicidal product is potassium glyphosate. Potassium glyphosate has been found to have a high solubility in water to produce solutions having high density and therefore high concentrations of glyphosate acid equivalent per unit volume. The use of alkaline earth hydroxides, such as $Ca(OH)_2$ can be advantageous in effecting precipitation of glyphosate from the reaction medium.

Where an excess of base is present during the course of the reaction, it will be understood that the halomethylphosphonic acid reactant may effectively constitute the salt of halomethylphosphonic acid rather than the acid itself. Moreover, regardless of whether any excess base is present, some fraction of halomethylphosphonate anion is necessarily present, either as the salt or by dissociation of the acid. Thus, wherever it is stated herein that the reaction is between "halomethylphosphonic acid" and an amine reactant, unless the context indicates to the contrary, those skilled in the art will understand that this is intended to encompass reaction between the amine substrate and halomethylphosphonate anion(s), whether effectively present in the form of a halomethylphosphonate salt or otherwise. Wherever the reaction is said to be with a "salt of halomethylphosphonic acid," those skilled in the art will understand that this encompasses reaction with halomethylphosphonate anion(s).

The proportion of water present has been found to have a significant effect on the glyphosate yield. Thus, the reaction medium preferably contains at least about 12 moles water, more preferably at least about 25 moles, most preferably at least about 40 moles per mole halomethylphosphonic acid. The presence of a high molar concentration of water contributes to favorable yields, though unnecessarily high water concentrations should be avoided to prevent undue dilution of the product with consequent penalty in reactor payload and productivity.

Where the reaction is conducted in batch mode, excess amine reactant and halomethylphosphonic acid are charged to the reaction vessel in the preferred ratios stated above. The initial concentration of halomethylphosphonic acid in the reaction medium is preferably at least about 3% by weight, more typically between about 5% and about 15% by weight; and the initial concentration of amine reactant is between about 4% and about 60%, preferably between about 35% and about 60%, by weight. At the end of the reaction, the reaction mixture contains between about 4% and about 30%, preferably between about 15% and about 25%, by weight of alkali metal glyphosate or other product corresponding to Formula I.

Reaction may be carried out at a temperature in the range of ambient temperature to about 150° C., preferably between about 70° and about 140° C., most preferably between about 100° and about 1300C. The reaction is preferably performed in a pressure vessel or the like. In a batch reaction system, reaction times may typically range from about 5 to about 40 hours, more typically from about 10 to about 20 hours.

The reaction is preferably conducted in the presence of an additive which promotes the progress of the reaction. Particularly preferred promoters include halide ions, Lewis acids, and organic bases.

Particularly preferred nitrogenous organic bases include polyamines, polyimines such as polyethyleneimine, or a heterocyclic base such as pyridine, polyvinylpyridine or a polyazomacrocycle. Without being bound to any particular theory, it is postulated that an organic base may effectively catalyze the reaction by serving to deprotonate the amine reactant and thereby enhance its activity for reaction with the methyl halide moiety of the halomethylphosphonic acid. Preferably, the reaction medium may contain between about 0.1% and about 10% by weight, more preferably between about 1% and about 3% by weight, of polyethyleneimine or other organic base.

Where the halomethylphosphonic acid is chloromethylphosphonic, other preferred promoters include bromide ion and iodide ion, typically provided in the form of the sodium, potassium or ammonium salt. It is believed that bromide and iodide participate in a reversible halogen exchange reaction with chloromethylphosphonic acid, producing an equilibrium concentration of the bromomethyl- or iodomethylphosphonic acid. According to this hypothesis, consumption of bromomethyl- or iodomethylphosphonic acid by reaction with the amine substrate drives the halogen exchange equilibrium reaction to generate additional bromomethyl- or iodomethylphosphonic acid for further reaction with the substrate. Thus, only a catalytic amount of iodide or bromide ion is required to provide a beneficial effect on the reaction, e.g., between about 5 mole % and about 10 mole % based on chloromethylphosphonic acid. Note that, where the halomethylphosphonic acid reactant is bromomethylphosphonic, the use of a comparable proportion of iodide ion may serve to promote the reaction.

Other additives may also be useful as promoters for the reaction. For example, compounds which function as Lewis acids in the reaction environment may also serve to promote the reaction. Such additives include species such as silica, phenolates, e.g., polyvinylphenol, aluminum oxide, zinc chloride, boron trifluoride, and rare earth metal hydroxides such as lanthanum hydroxide. These may typically be present in the reaction medium in proportions of between about 0.1% and about 10% by weight, more typically 1% to 5% by weight. These additives generally exhibit a catalytic effect on the reaction, though the mechanism by which they promote the reaction is not well understood.

Because the reaction is preferably conducted with a substantial excess of amine reactant and/or with a substantial molar excess of water, the reaction is advantageously conducted in a continuous mode to enhance productivity. Under the preferred conditions, the reaction proceeds substantially to completion in a single stage continuous stirred tank reactor. Where the reaction is conducted in a single phase system, it may also be advantageously carried out in a pipeline or other flow reactor. Since the reaction is endothermic, the use of a continuous stirred tank reactor is advantageous in facilitating supply of reaction heat by transfer of heat from steam or other heat transfer fluid to the reaction medium via either jacket, internal coils or circulation through an external exchanger. However, satisfactory heat transfer can also be achieved in a pipeline reactor, either from a steam jacket, by live steam injection into the reactor, or intermediate reheating of the reacting mixture in heat exchangers positioned between successive pipeline reactors oriented in series.

Where a substantially plug flow reaction system is used, reactant concentrations at the reactor inlet are comparable to those prevailing at the start of a batch reaction cycle as described above. Where a continuous stirred tank or other substantially backmixed reactor is used, the composition of the reaction medium is essentially that of the finished reaction mixture. In either case, charge ratios are similar to those prevailing in the batch process.

Evaporative concentration of the reaction mixture can also be conducted on a continuous basis if desired, as may crystallization of glyphosate or other product of Formula I from the concentrated reaction mixture, e.g., by use of a scraped surface heat exchanger followed by a centrifuge or continuous filter for recover of the crystallized product.

Recovery Schemes for Glycine Reactions

Glyphosate or other product of Formula I may be separated from the reaction mixture by any of various process alternatives. Regardless of the ultimate method of recovery, it is generally desirable to produce a concentrated solution of the Formula I product by evaporation of excess water and/or other solvent. Any alkali metal halide by-product, as well as any heterogeneous additives such as silica, aluminum oxide or rare earth hydroxides, should be removed, as by filtration, prior to evaporation of solvent, or in any event before the reaction mixture or concentrate is further processed for recovery of glyphosate or other product of Formula I.

In accordance with one alternative for ultimately recovering the product, an insoluble glyphosate chelate can be formed by addition of a salt, oxide or hydroxide of a heavy metal or other polyvalent metal to a product recovery feed mixture comprising the reaction mixture, filtrate thereof, or preferably a concentrate obtained by evaporation of excess solvent therefrom. After separation of the chelate precipitate by filtration or centrifugation, glyphosate may be liberated from the chelate by contact with an acid, or alternatively a base, and the reconstituted salt or hydroxide recovered in a suitable manner and recycled for use in further precipitation of glyphosate from the reaction mixture. The supernatant filtrate obtained in separation of the chelate typically contains unreacted amine reactant and may be recycled to provide part of the amine reactant to be used in the reaction. A fraction of the filtrate may need to be purged or processed for removal of glyphosine and other by-products.

In another alternative recovery process, glyphosate may be recovered by acidification of the reaction mixture or reaction mixture concentrate, e.g., by addition of HCl thereto, thereby reducing the pH to the about isoelectric point of glyphosate, i.e., about 5.5 to about 6.5 and causing precipitation of the free acid form of the product. After recovery of the free acid by filtration or centrifugation, the resultant filtrate can be recycled to the reaction step as a source of amine reactant, with an appropriate fractional purge or other processing for removal of by-products.

According to a still further alternative, the product of Formula I may be recovered by crystallization thereof. Crystallization may be an especially attractive alternative where the reaction medium comprises a mixture of water and a polar solvent, e.g., water and a primary alcohol. In such a process, the reaction mixture is concentrated by evaporation and the product crystallized by concentration alone, or by the combined effect of concentration and subsequent cooling of the concentrate obtained as the residue of the evaporation. Crystalline product may then be recovered by filtration or centrifugation and crystallization mother liquor recycled to the reaction step, again with whatever purge, ion exchange treatment, and/or other processing may be appropriate for removal of impurities. FIGS. 1-4 illustrate separation scheme flow diagrams representing equipment systems which are designed to perform the separation unit operations in accordance with certain preferred embodiments of the present invention.

Exemplary compositions of the various streams are disclosed infra. The water content of the streams described in the exemplary separation schemes, infra, is generally selected to yield a stream which is at least about 65% by weight water to ensure no unintended "salting out" of dissolved reactants or products in process equipment and to arrive at a product which is about 90% water on a molar basis. More or less water may be used depending on process economics and efficiencies, so long as a minimum amount of water is present to avoid "salting out."

Illustrated in FIG. 1 is a preferred process for recovery of an alkali metal salt of glyphosate from an aqueous mixture obtained by reaction of a halomethylphosphonic acid or a salt thereof with glycine or an alkali metal glycinate in the presence of a base. Specifically illustrated is a process for recovering potassium glyphosate produced in the reaction of chloromethylphosphonic acid with potassium glycinate. In the embodiment of the process as illustrated, reactants are charged in a K glycinate to CMPA molar ratio of 10:1, together with water in a molar ratio to K glycinate of 4:1. In this embodiment, CMPA is reacted substantially to completion, producing a reaction mixture containing tripotassium glyphosate (1 mole), K glycinate (6 moles) glycine (3 moles), KCl (1 mole) and water (40 moles).

An aqueous product recovery feed mixture comprising or derived from the reaction mixture is charged to an anion exchange column containing a suitable resin. Generally, the resin is selected with consideration for the relative propensity of the substituents of the product recovery feed mixture to be adsorbed to the ion exchange medium. For example, the $pK_a$ of the substituents may provide a guide for a resin which exchanges out OH⁻ ions, and the column may then be designed to be initially loaded with anions in descending order of $pK_a$.

In the embodiment of FIG. 1, the column is designed such that the column is preferentially loaded with Cl⁻ and (K₂glyphosate)⁻ ions as ion exchange progresses, though more specialized ion exchange materials and column designs may be used to selectively isolate individual anions. The unreacted amino acid constituents of the reaction mixture, i.e., glycine and glycinate ion, pass through the column, producing an aqueous column effluent containing K glycinate (6 moles), glycine (3 moles), KOH (2 moles), and water (40 moles). This aqueous effluent from the ion exchange column, containing unreacted glycine and glycinate, is recycled to the reaction step to provide a portion of the amine reactant for further formation of glyphosate salt. Additional CMPA (1 mole), glycine (1 mole) and KOH (2 moles) are mixed with the recycle stream or separately introduced into the reaction system.

The loaded column is eluted with an aqueous KOH solution (2 moles KOH; 40 moles water) to produce an eluate comprising tripotassium glyphosate (1 mole), KCl (1 mole) and water (40 moles). The eluate is neutralized with HCl (2 moles; 7 moles water) to yield a neutralized eluate containing monopotassium glyphosate (1 mole), KCl (3 moles) and water (47 moles). The neutralized eluate is subjected to nanofiltration with the addition of dilution water as required, e.g. an additional 40 moles, yielding a filtrate containing KCl (3 moles) and water (78 moles), and a halide-depleted retentate comprising K glyphosate (1 mole) and water (9 moles).

Figure 2:
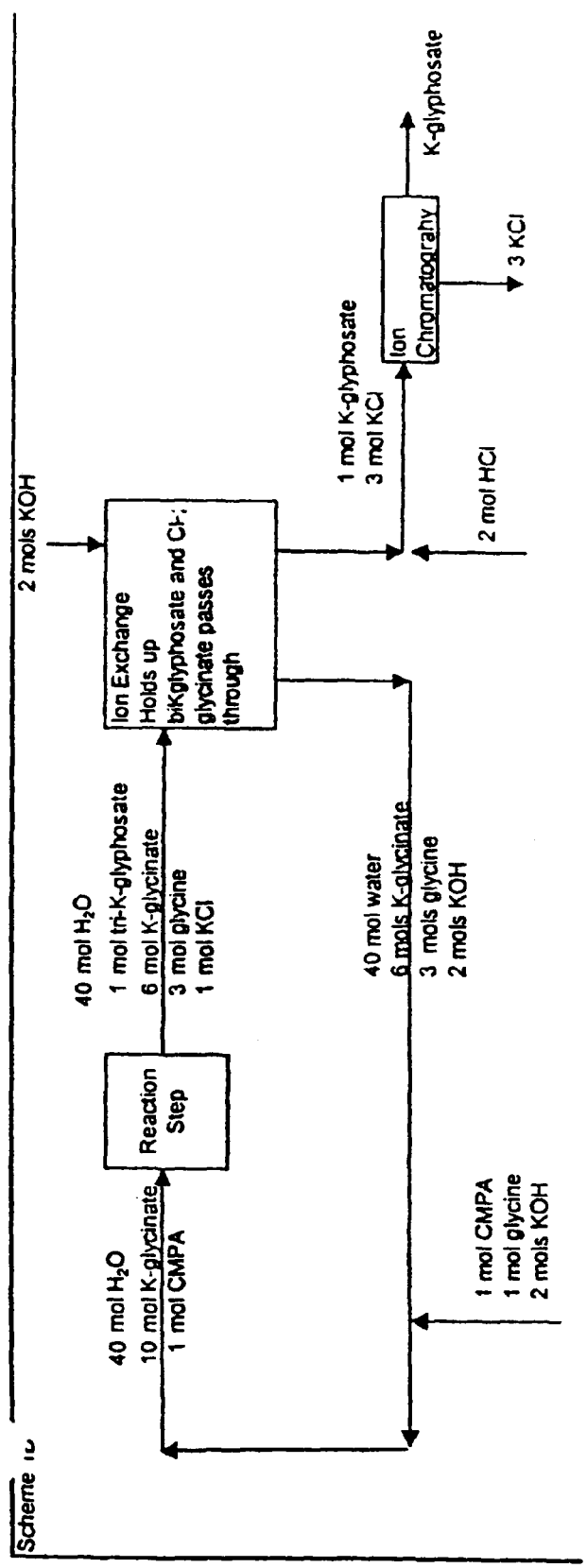

FIG. 2 illustrates an alternative embodiment of FIG. 1 wherein KCl is separated from the K glyphosate product by chromatography rather than by nanofiltration. The product recovery feed mixture is contacted with an ion exchange resin in a primary separation zone, producing an aqueous effluent having the same composition as the ion exchanger effluent described above with respect to the process of FIG. 1. The ion exchange resin is eluted with aqueous KOH (2 moles KOH; 40 moles water) to produce a primary eluate containing K₃ glyphosate (1 mole), KCl (1 mole) and water (40 moles). This eluate is mixed with HCl (2 moles; 7 moles water) to produce a neutralized primary eluate comprising monopotassium glyphosate (1 mole), KCl (3 moles) and water (47 moles).

The neutralized primary eluate is subjected to a chromatographic separation system, e.g. one or more size exclusion or ion chromatography columns. In one embodiment, the eluate stream is contacted with a chromatographic medium in a secondary separation zone comprising a beds or columns containing a chromatographic medium. The medium may be selective for Cl⁻ ion in preference to the (glyphosate)⁻ ion or may be selective for (glyphosate)⁻ ion in preference to the Cl⁻ ion. In one embodiment according to FIG. 2, the chromatographic separation is performed with one or more columns with media which performs a size exclusion separation, so that the rate of passage (glyphosate)⁻ ion of through the bed or column is retarded relative to the rate of passage of Cl⁻ therethrough. The column system is operated to produce a first eluate comprising K glyphosate (1.0 mole) and water (9 moles) and a second eluate comprising KCl (3 moles) and water (47 moles). The first eluate comprises a product solution useful as an herbicide or herbicide concentrate.

Alternatively, by proper selection of ion exchange resin and elution conditions in the primary ion exchange operation, the loaded ion exchange column can first be eluted for preferential recovery of K₃ glyphosate, and thereafter be eluted for removal of chloride ions which are retained on the column during elution of K₃ glyphosate. The aqueous glyphosate eluate contains between about 10% and about 50% by weight K₃ glyphosate (1.0 mole) in water. After addition of HCl, the resultant neutralized eluate contains only about 2 moles chloride ion per mole glyphosate ion, thereby proportionately reducing the load on the nanofiltration system or ion chromatography column for removal of residual chlorides.

Instead of ion exchange, the primary separation of glycine and glycinate from glyphosate can be conducted by ion chromatography or size exclusion chromatography. The aqueous product recovery feed mixture is contacted with a chromatographic medium that is relatively selective for glyphosate anion versus other amino acid constituents of the mixture such as unreacted glycine, glycine salt, N-substituted glycine or N-substituted glycine salt. The aqueous feed mixture is passed through a bed or column containing the chromatographic medium, the medium being effective to retard passage of glyphosate species through the bed or column relative to flow of unreacted amino acid constituents of the feed mixture, i.e., glycine or glycine salt, therethrough. Thus, glyphosate or glyphosate salt is loaded onto the medium, and an aqueous effluent stream is produced which contains unreacted amine constituents but is depleted in glyphosate anion. The aqueous effluent stream containing glycine or glycinate salt is preferably recycled to the reaction zone where the glycine or glycinate salt reacts with a further supply of halomethylphosphonic acid reactant. Glyphosate is ultimately eluted with an aqueous alkaline solution, typically as trialkali metal glyphosate. Depending on selection of the chromatographic or ion exchange medium and system design for each separation operation, chlorides may elute with glyphosate, or with the other amino acid constituents, or in a fraction separate from either of the amino acid fractions. As in the embodiments of FIGS. 1 and 2, the chloride load on the post-neutralization nanofiltration or ion chromatography separation step can be reduced by separation of chlorides from glyphosate in the primary chromatographic separation step.

Figure 3:
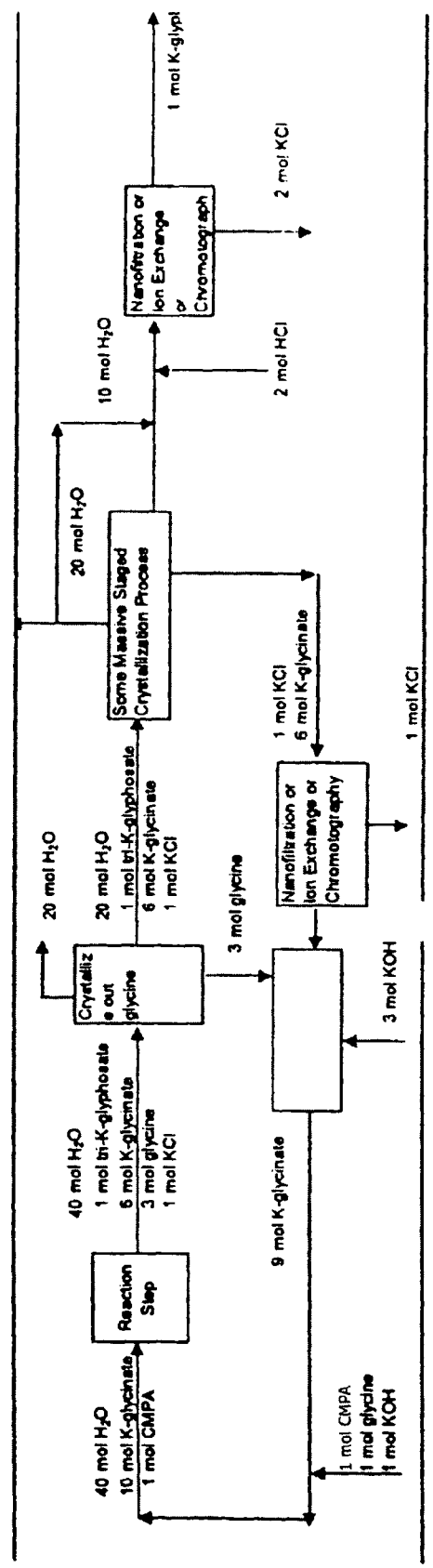

An alternative recovery process is illustrated in FIG. 3 wherein glyphosate product is separated from unreacted amine constituents by crystallization rather than ion exchange or chromatography. In the process of FIG. 3, the reaction step is conducted in the same manner as described above for the system of FIG. 1. An aqueous product recovery feed mixture comprising or derived from the reaction mixture is subjected to a preliminary evaporative crystallization and the resulting slurry subjected to solids/liquid separation (as by filtration or centrifugation) to yield crystalline glycine (3 moles), an overhead vapor stream consisting mainly of water vapor (20 moles) and a preliminary crystallization mother liquor comprising dipotassium hydrogen glyphosate (1 mole), K glycinate (6 moles), KCl (1 mole) and water (20 moles). The preliminary crystallization mother liquor is subjected to further multi-stage evaporative crystallization for recovery of crystalline tripotassium glyphosate (1 mole). In the multistage crystallization of K₃ glyphosate, additional water vapor (20 moles) is driven overhead, and a glyphosate salt crystallization mother liquor is produced comprising K glycinate (6 moles) and KCl (1 mole). The crystalline tripotassium product is redissolved in water, preferably overhead condensate from the K₃ glyphosate crystallization (10 moles), and neutralized with HCl (2 moles) and additional water to produce a product repulp solution containing monopotassium glyphosate (1.0 mole) and KCl (2.0 moles). The product repulp solution is subjected to nanofiltration and the addition of more water to produce a filtrate comprising KCl (2.0 moles) and water (78 moles) and a halide-depleted retentate comprising K glyphosate (1.0 mole) and water (9 moles). Alternatively, the alkali metal halide salt may be separated by ion exchange or by chromatography. For example, a chromatographic medium may be first eluted with water to produce a first eluate comprising KCl (2.0 moles) and water (47 moles). The medium is thereafter eluted with water to produce a second eluate comprising monopotassium glyphosate (1 mole) and water (9 moles).

Crystalline glycine obtained in the preliminary crystallization step is repulped in an aqueous medium to produce an amine reactant repulp solution that is recycled to the reaction zone.

Figure 4:
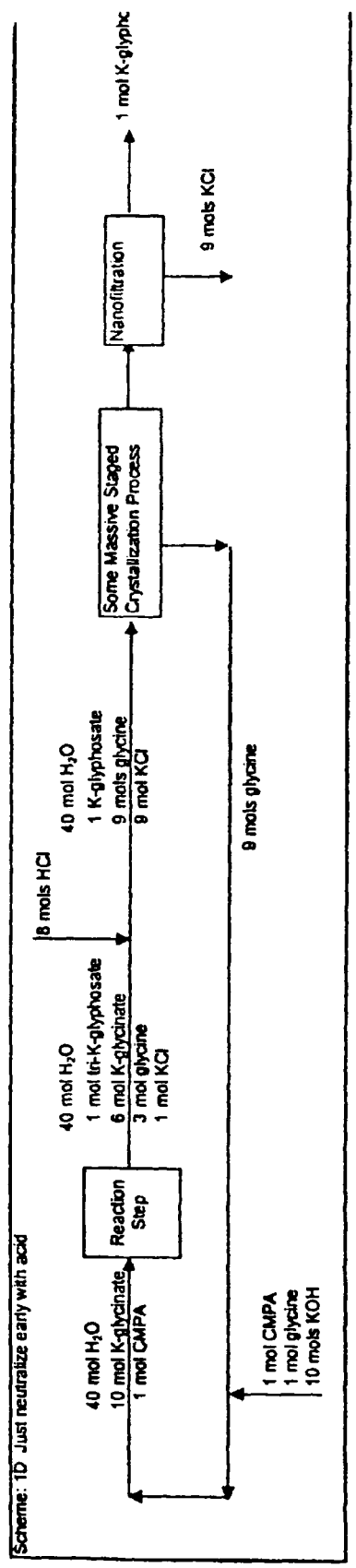

FIG. 4 illustrates an alternative crystallization process for recovery of K glyphosate. The reaction is conducted in the manner described above with respect to FIG. 3, but the reaction mixture is neutralized by addition thereto of HCl (8 moles) sufficient to neutralize all the K glycinate present, forming a neutralized reaction mixture comprising glycine (9 moles) comprising monopotassium glyphosate (1 mole), KCl (9 moles) and water (40 moles). The neutralized reaction mixture is concentrated by evaporation of water therefrom, resulting in crystallization. Preferably, evaporation of water is conducted at reduced pressure so that the liquid phase is cooled, resulting in further crystallization of glycine. To enhance the separation, a multistage fractional crystallization is preferably conducted. The crystallization mother liquor containing monopotassium glyphosate (1.0 mole) and KCl (9 moles) is subjected to nanofiltration with additional water to yield a filtrate containing KCl (9 moles) and water (71 moles), and a halide-depleted retentate comprising K glyphosate (1 mole) and water (9 moles).

Crystallized glycine (9 moles) is recycled to the reaction step, preferably in the form of an aqueous amine reactant repulp solution (containing 40 moles water). Additional CMPA (1 mole), glycine (1 mole) and KOH (9 moles) are mixed with the recycle stream or separately introduced into the reaction system. To minimize KOH consumption and salt generation, the process of FIG. 4 is preferably conducted at a glycine/CMPA ratio substantially lower than 10, preferably <5, more preferably <3. At such lower reactant ratios, the compositions of the FIG. 4 process streams vary from those described above, as may be determined from the material balance.

It will be understood that the flow sheets of FIGS. 1-4 are simplified schematics. Within the scope of the invention, the reaction mixture may be subjected to various preliminary operations to provide the aqueous product recovery feed mixture that is introduced into the ion exchange column of FIG. 1 or 2, the crystallizer of FIG. 3 or the neutralization step of FIG. 4. Thus the aqueous product recovery feed mixture may constitute, e.g., a concentrate, dilution, filtrate or other stream derived from preliminary processing of the reaction mixture.

As discussed elsewhere herein, the ratio of glycine to CMPA in the processes of FIGS. 1 to 4 can be significantly lower than the 10:1 ratio described immediately above. As also discussed elsewhere herein, the water/glycine and water/CMPA ratios can be adjusted to increase or decrease the degree of dilution. The KOH/glycine ratio may also be adjusted as discussed herein. The compositions of other process streams vary with the glycine/CMPA ratio, water/CMPA ratio and KOH/glycine ratio in accordance with the dictates of the material balance.

Recovered products and product streams from these separation processes may serve as reactor feed streams for further reaction of the compound of Formula I in the preparation of other products. For example, N-substituted products may be converted to unsubstituted forms which are useful as herbicides or herbicide concentrates.

Oxidation of N-Substituted N-(phosphonomethyl)glycine and Derivatives

Where the products according to Formula I are N-substituted, i.e. $R^1$ is not hydrogen but otherwise as described above, such products comprise valuable intermediates in the production of glyphosate and other glyphosate derivatives. Methods are available to further convert N-substituted products into unsubstituted forms. For example, the novel methods described in U.S. Pat. No. 6,005,140 (1999), U.S. Pat. No. 6,232,494 (2001), and co-pending U.S. application Ser. No. 09/248,655 (filed Feb. 11, 1999) teach a catalyzed oxidation process as a means to remove the substituted groups. Specifically, these references disclose a novel and useful method for manufacturing glyphosate, its salts, and its esters, in an aqueous medium wherein an N-substituted glyphosate or a salt or ester thereof (collectively referred to as "N-substituted glyphosate product") is oxidatively cleaved with oxygen over a noble metal catalyst. These references are incorporated herein by reference in their entirety.

In general, glyphosate and its salts and esters may be prepared, in accordance with these references, from N-substituted glyphosate products of a halophosphonomethylization process corresponding to Formula I, wherein $R^1$ is preferably a substituted or unsubstituted alkyl, alkenyl, alkynyl, aryl, aralkyl, aralkenyl or aralkynyl, and $R^2$, $R^3$, and $R^4$ are as defined above. Compounds wherein $R^1$ is a substituted group, e.g. N-(phosphonomethyl)iminodiacetic acid (sometimes referred to as "PMIDA"), as well as compounds wherein $R^1$ is an unsubstituted group may be produced according to the present invention.

PMIDA is a well-known glyphosate intermediate according to Formula III having two N-carboxymethyl groups, i.e. $R^1$ is —$CH_2CO_2H$. PMIDA may be synthesized from phosphorus trichloride, formaldehyde, and an aqueous solution of the disodium salt of iminodiacetic acid, as described by Gentilcore in U.S. Pat. No. 4,775,498.

PMIDA may be converted into glyphosate by heterogeneous oxidation over carbon catalysts as described, for example, in U.S. Pat. No. 3,950,402 to Franz and U.S. Pat. No. 4,654,429 to Balthazor et al.; by homogenous catalytic oxidation as described, for example, in Riley et al. J. Amer. Chem. Soc. 113, 3371-78 (1991) and Riley et al. Inorg. Chem. 30, 4191-97 (1991); and by electrochemical oxidation using carbon electrodes as described, for example, in U.S. Pat. No. 3,835,000 to Frazier et al. In U.S. application Ser. No. 09/248,655, Ebner et al. ("Ebner") teach a catalyst and process to catalyze liquid phase oxidation reactions and disclose a preferred embodiment for the oxidation of PMIDA to glyphosate.

In U.S. Pat. Nos. 6,005,140 and 6,232,494, Morgenstern et al. ("Morgenstern") teach a catalyst and process for the oxidation of compounds wherein $R^1$ is other than a carboxymethyl group. Typical unsubstituted substituents which may constitute $R^1$ include methyl, ethyl, n-propyl, isopropyl, n-butyl, isobutyl, pentyl, hexyl, octyl, decyl, vinyl, allyl, pentenyl, ethynyl, butynyl, benzyl, phenylethyl, phenylvinyl, phenylallyl, p-methylphenylethyl, phenylethynyl and the like. Preferably $R^1$ is methyl or isopropyl. Most preferably $R^1$ is methyl.

The oxidation reaction is normally a heterogenous catalysis reaction. Preferably, an aqueous solution containing an N-substituted glyphosate product is introduced into a reactor along with an oxidizing agent, preferably an oxygen-containing gas or a liquid comprising dissolved oxygen. In the presence of a noble metal catalyst (i.e., a catalyst comprising a noble metal), the N-substituted glyphosate product is oxidatively converted to a compound of Formula Ia or a salt or ester thereof:

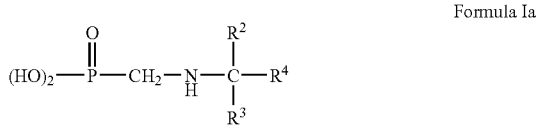

Formula Ia wherein $R^2$, $R^3$, and $R^4$ are as defined above.

The N-substituted glyphosate product is preferably a product of a halophosphonomethylization reaction of a N-substituted glycine reactant according to Formula III. The reaction of a halomethylphosphonic acid with an N-substituted glycine reactant has several process advantages over a reaction with an unsubstituted compound. For example, the ratio of N-substituted glycine to CMPA may be far less than the 10:1 glycine: CMPA ratio in the preferred embodiment described above for reaction of substrates wherein $R^1$=H. Preferably the N-substituted glyphosate product is prepared from a reaction where such a ratio is no greater than about 3, more preferably no greater than about 2, even more preferably no greater than about 1.5, still more preferably no greater than about 1.25, and even still more preferably no greater than about 1.1. Most preferably the ratio is about 1, i.e. the halomethylphosphonic acid reactant and the N-substituted glycine reactant are contacted in substantially equivalent proportions. Lowering the ratio to approach stoichiometric proportions provides the process advantages of simplifying product recovery and of reducing or eliminating the recycle of reactants as well as reducing the amount of salt to be removed from the product stream in the separation schemes described above. Preferably, separation is achieved in a single-step process to remove halides with no additional steps being required or practiced to remove unreacted precursors of N-substituted glyphosate product.

Because strong acids tend to inhibit the conversion of halomethylphosphonic acid, the N-substituted glyphosate product solution is neutral or basic but may be acidic as a result of the separation steps. It is preferred that the N-substituted glyphosate product solution be substantially free of halide ions. Halide ions have been observed to inactivate some preferred noble metal catalysts. The N-substituted glyphosate product may be separated from halide ions by any suitable separation process, for example the novel separation schemes described above. Preferably, the N-substituted glyphosate product is separated by nanofiltration alone, without the other steps required for separation of unreacted glycine or glycinate.

In a particularly advantageous embodiment, the "N-substituted" reactant according to Formula III preferably comprises iminodiacetic acid (IDA) and the halomethylphosphonic acid reactant preferably comprises CMPA. CMPA is preferably reacted with IDA in about equimolar amounts. The reaction is performed in the presence of a aqueous base solution. The base is preferably an inorganic base, such as sodium hydroxide or potassium hydroxide, or an organic base selected from alkyl-substituted ammonium, phosphonium, sulfonium, or sulfoxonium hydroxides. Preferably a molar ratio of the base to the IDA or CMPA reactant is between about 3 and about 5 preferably at least about 4.

Conversion of halomethylphosphonic is promoted if IDA is charged at a molar ratio to halomethylphosphonic acid of at least about 1.5. Advantageously, however, as in the case of other secondary amines, the reaction may conducted at a substantially 1:1 ratio without formation of the bis(phosphonomethyl adduct). Preferably, therefore, the ratio of IDA to halomethylphosphonic acid is not greater than about 1.2 to one, more preferably not greater than about 1.1 to one.

IDA and CMPA react to produce N-phosphonomehtyliminodiacetic acid (Glyphosate Intermediate or "GI") as an N-substituted product according to Formula I. As discussed, GI is a valuable intermediate in the production of glyphosate. GI may be oxidatively cleaved to produce glyphosate according to the methods described infra.

GI yields in the range about 55-70% on the basis of CMPA may be achieved at preferred reaction temperatures of from about 80° C. to about 110° C., more typically 90°-100° C. over preferred reaction times of from about 15 hours to about 20 hours. As in the case of primary amines, the reaction is preferably conducted in a relatively dilute aqueous medium having a relatively high ratio of water to halomethylphosphonic acid. The ratios of water to halomethylphosphonic acid, as discussed above, are generally applicable to secondary amines such as IDA also.

In an alternative embodiment, the reaction of halomethylphosphonic acid and IDA is catalyzed. In the presence of a Cu-containing catalyst, for example, GI yields of about 35% to about 98% may be achieved in reaction times from about 1.5 hours to about 6 hours. Either homogeneous or heterogeneous catalysts may be used to promote the reaction with IDA. Homogeneous catalysts may comprise copper salts such as cupric chloride, cuprous chloride, or cupric perchlorate that are soluble in water or in an alkaline aqueous medium. Heterogeneous catalysts may include, e.g., cupric hydroxide, cupric acetate on a polyvinylpyridine support, cupric oxide, copper powder, Raney copper, cupric oxide on a silica, alumina, $C_{R2}O_3$ or $MnO_2$ support, etc. Other useful copper catalysts include catalysts described in Ebner et al. U.S. Pat. No. 5,689,000 comprising metallic copper anchored to a carbon support with a noble metal such as palladium or platinum, and the various copper/nickel sponge catalysts described in WO 03/033140. Whether in homogeneous or heterogeneous form, a copper catalyst is typically present in a copper concentration between about 0.01 and about 10 wt. %, basis the entire reaction mass. According to a further alternative, a heterogeneous catalyst may be formed as a fixed or fluidized bed through which a reaction medium containing IDA and HMPA or HMPA source is passed.

Heterogeneous catalyst may be removed from the reaction mixture by filtration and recycled for use in conversion of further amounts of IDA to PMIDA. A homogeneous catalyst remains in the mother liquor upon precipitation of PMIDA. At least a fraction of the mother liquor may typically be recycled and incorporated into the medium for further reaction of IDA and halomethylphosphonic acid. Copper contained in the mother liquor is made available to catalyze such further reaction. At least a portion of the mother liquor is typically removed from the process to purge by-products and impurities. Fresh catalyst is added to compensate for Cu removed in a mother liquor purge. The extent to which catalyst may be recycled can be increased by concentrating the mother liquor to precipitate by-product salt such as NaCl or KCl. If process economics so justify, Cu losses in purged mother liquor, or in precipitated salt, may be minimized by treating the mother liquor or mother liquor purge by ion exchange for recovery of cupric Cu.

As noted, the halomethylphosphonic acid reactant preferably comprises chloromethylphosphonic acid. Bromomethylphosphonic and iodomethylphosphonic acids are equally reactive, possibly more reactive, but chloromethylphosphonic acid serves as a more economical raw material for an industrial manufacturing process. Further, as discussed below, the use of additives may render chloromethylphosphonic effectively as reactive as other halomethylphosphonic acid species.

Glyphosate intermediate (also referred to herein as "PMIDA") may be recovered from the reaction mixture according to any of the various schemes described hereinbelow. According to an alternative and preferred embodiment, the reaction solution may be brought to the isoelectric point of PMIDA, typically by addition of acid such as HCl or HBr, causing precipitation of PMIDA. The PMIDA can be recovered by centrifugation or filtration, redissolved in water and converted to glyphosate by catalytic oxidation according to the processes well know to the art.

The copper catalysts that are useful in the reactions of IDA with halophosphonic acid are generally useful in the reactions of other secondary amines as well. It is understood that such catalysts are also active in the reactions of primary amines. However, in the latter case, they tend to foster the formation of the bis(phosphonomethyl) adducts such as glyphosine.

Oxidation of PMIDA and Like Compounds

Though directed at oxidation reactions in general and the oxidation of tertiary amines to form secondary amines, the catalyst taught by Ebner is particularly suited for oxidizing PMIDA because the catalyst is also effective to oxidize the resulting formaldehyde and formic acid by-products into carbon dioxide and water. The preferred oxidation catalyst comprises a carbon support having a noble metal, and optionally a promoter and carbon, at its surface.

The form of the carbon support is not critical. In one embodiment of this invention, the support is a monolithic support. Suitable monolithic supports may have a wide variety of shapes. Such a support may be, for example, in the form of a screen or honeycomb. Such a support may also, for example, be in the form of a reactor impeller. In a particularly preferred embodiment, the support are in the form of particulates.

The catalyst preferably has one or more noble metal(s) at its surface. Preferably, the noble metal(s) is selected from the group consisting of platinum (Pt), palladium (Pd), ruthenium (Ru), rhodium (Rh), iridium (Ir), silver (Ag), osmium (Os), and gold (Au). In general, platinum and palladium are more preferred, and platinum is most preferred.

In addition to the noble metal, at least one promoter may be at the surface of the carbon support. Although the promoter typically is deposited onto the surface of the carbon support, other sources of promoter may be used (e.g., the carbon support itself may naturally contain a promoter). A promoter tends to increase catalyst selectivity, activity, and/or stability. A promoter additionally may reduce noble metal leaching.

The promoter may, for example, be an additional noble metal(s) at the surface of the carbon support. For example, ruthenium and palladium have been found to act as promoters on a catalyst comprising platinum deposited at a carbon support surface. The promoter(s) alternatively may be, for example, a metal selected from the group consisting of tin (Sn), cadmium (Cd), magnesium (Mg), manganese (Mn), nickel (Ni), aluminum (Al), cobalt (Co), bismuth (Bi), lead (Pb), titanium (Ti), antimony (Sb), selenium (Se), iron (Fe), rhenium (Re), zinc (Zn), cerium (Ce), and zirconium (Zr). Preferably, the promoter is selected from the group consisting of bismuth, iron, tin, and titanium. In a particularly preferred embodiment, the promoter is tin. In another particularly preferred embodiment, the promoter is iron. In an additional preferred embodiment, the promoter is titanium. In a further particularly preferred embodiment, the catalyst comprises both iron and tin.

The oxidation catalyst is preferably prepared as follows. First, the carbon support is deoxygenated. Second, the noble metal is deposited on the support. Third, a promoter may be deposited on the support, either before, simultaneously, or after the deposition of the noble metal. Fourth, the carbon support surface is reduced, as by methods known in the art, e.g., heating in a non-oxidizing atmosphere or treating with an amine.

The above-described catalyst is especially useful in liquid phase oxidation reactions at pH levels less than 7, and in particular, at pH levels less than 3. It also is especially useful in the presence of solvents, reactants, intermediates, or products which solubilize noble metals. One such reaction is the oxidation of PMIDA or a salt thereof to form N-(phosphonomethyl)glycine or a salt thereof in an environment having pH levels in the range of from about 1 to about 2. The description below will disclose with particularity the use of the above-described catalyst to effect the oxidative cleavage of PMIDA or a salt thereof to form N-(phosphonomethyl)glycine or a salt thereof. It should be recognized, however, that the principles disclosed below are generally applicable to other liquid phase oxidative reactions.

To begin the PMIDA oxidation reaction, it is preferable to charge the reactor with the PMIDA reagent (i.e., PMIDA or a salt thereof), catalyst, and a solvent in the presence of oxygen. The solvent is most preferably water, although other solvents (e.g., glacial acetic acid) are suitable as well. The reaction may be carried out in a wide variety of batch, semi-batch, and continuous reactor systems. The configuration of the reactor is not critical.

When conducted in a continuous reactor system, the residence time in the reaction zone can vary widely depending on the specific catalyst and conditions employed. Typically, the residence time can vary over the range of from about 3 to about 120 minutes. Preferably, the residence time is from about 5 to about 90 minutes, and more preferably from about 5 to about 60 minutes. When conducted in a batch reactor, the reaction time typically varies over the range of from about 15 to about 120 minutes. Preferably, the reaction time is from about 20 to about 90 minutes, and more preferably from about 30 to about 60 minutes.

In a broad sense, the oxidation reaction may be practiced in accordance with the present invention at a wide range of temperatures, and at pressures ranging from sub-atmospheric to super-atmospheric. Preferably, the PMIDA reaction is conducted at a temperature of from about 20 to about 180° C., more preferably from about 50 to about 140° C., and most preferably from about 80 to about 110° C. At temperatures greater than about 180° C., the raw materials tend to begin to slowly decompose.

The pressure used during the PMIDA oxidation generally depends on the temperature used. Preferably, the pressure is sufficient to prevent the reaction mixture from boiling. If an oxygen-containing gas is used as the oxygen source, the pressure also preferably is adequate to cause the oxygen to dissolve into the reaction mixture at a rate sufficient such that the PMIDA oxidation is not limited due to an inadequate oxygen supply. The pressure preferably is at least equal to atmospheric pressure. More preferably, the pressure is from about 30 to about 500 psig, and most preferably from about 30 to about 130 psig.

The catalyst concentration preferably is from about 0.1 to about 10 wt. % ([mass of catalyst÷total reaction mass]× 100%). More preferably, the catalyst concentration preferably is from about 0.2 to about 5 wt. %, and most preferably from about 0.3 to about 1.5 wt. %. Concentrations greater than about 10 wt. % are difficult to filter. On the other hand, concentrations less than about 0.1 wt. % tend to produce unacceptably low reaction rates.

The concentration of PMIDA reagent in the feed stream is not critical. Use of a saturated solution of PMIDA reagent in water is preferred, although for ease of operation, the process is also operable at lesser or greater PMIDA reagent concentrations in the feed stream. If the catalyst is present in the reaction mixture in a finely divided form, it is preferred to use a concentration of reactants such that all reactants and the N-(phosphonomethyl)glycine product remain in solution so that the catalyst can be recovered for re-use, for example, by filtration. Alternatively, if the catalyst is present as a stationary phase through which the reaction medium and oxygen source are passed, it may be possible to use greater concentrations of reactants such that a portion of the N-(phosphonomethyl)glycine product precipitates.

Normally, a PMIDA reagent concentration of up to about 50 wt. % ([mass of PMIDA reagent÷total reaction mass]× 100%) may be used (especially at a reaction temperature of from about 20 to about 180° C.). Preferably, a PMIDA reagent concentration of up to about 25 wt. % is used (particularly at a reaction temperature of from about 60 to about 150° C.). More preferably, a PMIDA reagent concentration of from about 12 to about 18 wt. % is used (particularly at a reaction temperature of from about 100° to about 130° C.). PMIDA reagent concentrations below 12 wt. % may be used, but their use is less economical because less N-(phosphonomethyl) glycine product is produced in each reactor cycle and more water must be removed and energy used per unit of N-(phosphonomethyl)glycine product produced. Lower temperatures (i.e., temperatures less than 100° C.) often tend to be less advantageous because the solubility of the PMIDA reagent and N-(phosphonomethyl)glycine product are both reduced at such temperatures.

The oxygen source for the PMIDA oxidation reaction may be any oxygen-containing gas or a liquid comprising dissolved oxygen. Preferably, the oxygen source is an oxygen-containing gas. The oxygen may be introduced by any conventional means into the reaction medium in a manner which maintains the dissolved oxygen concentration in the reaction mixture at the desired level. If an oxygen-containing gas is used, it preferably is introduced into the reaction medium in a manner which maximizes the contact of the gas with the reaction solution. Such contact may be obtained, for example, by dispersing the gas through a diffuser such as a porous frit or by stirring, shaking, or other methods known to those skilled in the art.

The oxygen feed rate preferably is such that the PMIDA oxidation reaction rate is not limited by oxygen supply. If the dissolved oxygen concentration is too high, however, the catalyst surface tends to become detrimentally oxidized. Generally, it is preferred to use an oxygen feed rate such that at least about 40% of the oxygen is utilized. More preferably, the oxygen feed rate is such that at least about 60% of the oxygen is utilized. Even more preferably, the oxygen feed rate is such that at least about 80% of the oxygen is utilized. Most preferably, the rate is such that at least about 90% of the oxygen is utilized.

Reduced losses of noble metal may be observed with this invention if a sacrificial reducing agent is maintained or introduced into the reaction solution. Suitable reducing agents include formaldehyde, formic acid, and acetaldehyde. Most preferably, formic acid, formaldehyde, or mixtures thereof are used. In one preferred embodiment, unreacted formaldehyde and formic acid are recycled back into the reaction mixture for use in subsequent cycles. In this instance, the recycle stream also may be used to solubilize the PMIDA reagent in the subsequent cycles.

Typically, the concentration of N-(phosphonomethyl)glycine in the product mixture may be as great as 40% by weight, or greater. Preferably, the N-(phosphonomethyl)glycine concentration is from about 5 to about 40%, more preferably from about 8 to about 30%, and still more preferably from about 9 to about 15%. Concentrations of formaldehyde in the product mixture are typically less than about 0.5% by weight, more preferably less than about 0.3%, and still more preferably less than about 0.15%.

Following the oxidation, the catalyst preferably is subsequently separated by filtration. The N-(phosphonomethyl) glycine product may then be isolated by precipitation, for example, by evaporation of a portion of the water and cooling.

It should be recognized that the catalyst has the ability to be reused over several cycles, depending on how oxidized its surface becomes with use. Even after the catalyst becomes heavily oxidized, it may be reused by being reactivated. To reactivate a catalyst having a heavily oxidized surface, the surface preferably is first washed to remove the organics from the surface. It then preferably is reduced in the same manner that a catalyst is reduced after the noble metal is deposited onto the surface of the support, as described above.

Oxidation of Other Glyphosate Intermediates

The Morgenstern references teach a catalyst and process which is preferred for oxidizing N-substituted, glyphosate intermediates with one n-carboxymethyl group. The catalyst comprises a noble metal catalyst.

The noble metal catalyst preferably comprises a noble metal selected from the group consisting of platinum (Pt), palladium (Pd), rhodium (Rh), iridium (Ir), osmium (Os), and gold (Au). In general, platinum and palladium are more preferred, with platinum being most preferred. Because platinum is most preferred, much of the following discussion will be directed to the use of platinum. It should be understood, however, that the same discussion is generally applicable to the other noble metals and combinations thereof.

The noble metal catalyst may be unsupported, e.g., platinum black. Alternatively, the catalyst may comprise a noble metal on the surface of a support, such as carbon, alumina ($Al_2O_3$), silica ($SiO_2$), titania ($TiO_2$), zirconia ($ZrO_2$), siloxane, or barium sulfate ($BaSO_4$). As described in U.S. Pat. No. 6,232,494, supported metals are common in the art and may be commercially obtained from various sources or also may be prepared by depositing the noble metal onto the surface of the support using any of the various methods well-known in the art.

If a carbon support is used, preferably the support is graphitic because such supports tend to have greater glyphosate selectivity, or the support has a surface which has been oxidized with a strong oxidizing agent before the noble metal is deposited onto the surface. A method for preparation of a carbon support by oxidation is described in U.S. Pat. No. 6,232,494. Useful catalytic structures where the noble metal is supported on a polymeric support (i.e., a support comprising a polymer) are also described. Various polyamides, polyimides, polycarbonates, polyureas, and polyesters may be used as the polymer. Preferably, the polymer is selected from the group consisting of polyethylene imine, salts of polyacrilic acid, polystyrene, polyaminostyrene, polystyrene substituted with dimethylamine groups, sulfonated polystyrene, and polyvinyl pyridine ("PVP"). More preferably, the polymer is selected from the group consisting of PVP and sulfonated polystyrene. In some embodiments, PVP is most preferred. In a particularly preferred embodiment, the noble metal is platinum and is deposited onto the surface of the support using a solution comprising $H_2PtCl_6$.

The concentration of the noble metal on the surface of a support may vary within wide limits. Preferably it is in the range of from about 0.5 to about 20 wt. % ([mass of noble metal÷total mass of catalyst]×100%)), more preferably from about 3 to about 15 wt. %, and even more preferably from about 5 to about 10 wt. %. At concentrations greater than about 20 wt %, layers and clumps of noble metal tend to form. Thus, there are fewer surface noble metal atoms per total amount of noble metal used. This tends to reduce the activity of the catalyst and is an uneconomical use of the costly noble metal.

The weight ratio of the noble metal to the N-substituted glyphosate product in the reaction mixture preferably is from about 1:500 to about 1:5. More preferably, the ratio is from about 1:200 to about 1:10, and even more preferably from about 1:50 to about 1:10. The catalyst may comprise a promoter in addition to a noble metal. The promoter may be on the surface of an unsupported noble metal, or on the surface of the noble metal and/or its support in the case of a supported noble metal catalyst. Preferably, the promoter comprises a metal selected from the group consisting of aluminum (Al), ruthenium (Ru), osmium (Os), indium (In), gallium (Ga), tantalum (Ta), tin (Sn), and antimony (Sb). More preferably, the promoter comprises a metal selected from the group consisting of gallium, indium, ruthenium, and osmium. Although a promoter may come from various sources (e.g., the catalyst may comprise a support which naturally contains a promoter), it typically is added to the surface of the noble metal. It should be recognized that if the catalyst comprises a support, the promoter typically is added to the surface of the noble metal, the surface of the support, or both. Methods used to deposit the promoter are generally known in the art and include the same methods which may be used to deposit a noble metal onto a support discussed above. The amount of promoter used (whether associated with the noble metal, a support on which the noble metal is deposited, or both) may vary within wide limits, depending in part on the promoter used. Preferably, the weight percentage of the promoter is at least about 0.05% ([mass of promoter÷total mass of the catalyst]×100%).The catalyst taught by U.S. Pat. No. 6,232,494 may also comprises an electroactive molecular species (i.e., a molecular species that may be reversibly oxidized or reduced by electron transfer). Preferably, this electroactive molecular species is on the surface of the noble metal (if the catalyst comprises a support, the electroactive molecular species preferably is on the surface of the noble metal, the surface of the support, or both). Selectivity and/or conversion of the noble metal catalyst may be improved by the presence of the electroactive molecular species, particularly where the catalyst is being used to effect the oxidation of N-methyl substituted glyphosate to form glyphosate. In this instance, the electroactive molecular species preferably is hydrophobic and has an oxidation potential ($E_{1/2}$) of at least about 0.3 volts vs. SCE (saturated calomel electrode). Electroactive molecular species also are useful in the context of the oxidation of N-isopropyl substituted glyphosate to form glyphosate. In that context, it is especially preferable for the catalyst to comprise a noble metal and an electroactive molecular species on a graphitic carbon support.

Examples of generally suitable electroactive molecular species include triphenylmethane; N-hydroxyphthalimide; 5,10,15,20-tetrakis(pentafluorophenyl)-21H,23H-porphine iron (III) chloride (abbreviated "Fe(III)TPFPP chloride"); 2,4,7-trichlorofluorene; triarylamines, such as N,N'-bis(3-methylphenyl)-N,N'-diphenyl benzidine (sometimes referred to as "TPD") and tris(4-bromophenyl)amine; 2,2,6,6-tetramethyl piperidine n-oxide (sometimes referred to as "TEMPO"); 5,10,15,20-tetraphenyl-21H,23H-porphine iron (III) chloride (sometimes referred to as "Fe(III)TPP chloride"); 4,4'-difluorobenzophenone; 5,10,15,20-tetraphenyl-21H,23H porphine nickel(II) (sometimes referred to as "Ni (II) TPP"); and phenothiazine. When the noble metal catalyst is being used to catalyze the oxidation of N-methyl substituted glyphosate to glyphosate, the particularly preferred electroactive molecular species are triarylamines; -hydroxyphthalimide; TEMPO; Fe(III)TPP chloride; and Ni(II) TPP. In many embodiments, triarylamines (especially TPD) are the most preferred electroactive molecular species. For example, at reaction temperatures greater than about 130° C., the most preferred electroactive molecular species is TPD.

The oxidation potentials for electroactive molecular species may be found in the literature. A compilation showing the oxidation potential and reversibility for a large number of electroactive molecular species may be found in *Encyclopedia of Electrochemistry of the Elements* (A. Bard and H. Lund eds., Marcel Dekker, New York, publication dates vary between volumes). Other sources for oxidation potentials are identified in U.S. Pat. Nos. 6,005,140 and 6,232,494. Various methods generally known in the art may be used to deposit an electroactive molecular species onto a noble metal catalyst. Alternatively, the electroactive molecular species may be added directly to the oxidation reaction mixture separately from the noble metal catalyst.

The concentration of N-substituted glyphosate product initially in the reaction medium may vary widely. Typically, the concentration is from about 1 to about 80 wt. % ([mass of N-substituted glyphosate÷total reaction mass]×100%). More preferably, the concentration is from about 5 to about 50 wt. %, and still more preferably from about 20 to about 40 wt. %.

The oxygen source for the oxidation reaction may be, for example, any oxygen-containing gas or a liquid comprising dissolved oxygen. Preferably, the oxygen source is an oxygen-containing gas, comprising molecular oxygen and which optionally may comprise one or more diluents which are non-reactive with the oxygen, the reactant, and the product under the reaction conditions. Examples of such gases include air, pure molecular oxygen, or molecular oxygen diluted with helium, argon, neon, nitrogen, or other non-molecular oxygen-containing gases. Preferably, at least about 20% by volume of the oxygen-containing gas is molecular oxygen, and more preferably, at least about 50% of the oxygen-containing gas is molecular oxygen.

The oxygen preferably is fed into the reaction mixture at a rate which is sufficient to maintain the dissolved oxygen concentration at a finite level. At reaction temperatures of about 125° C. or below, the oxygen is fed at a rate sufficient to maintain the dissolved oxygen concentration at no greater than about 2.0 ppm, but at a high enough concentration to sustain the desired reaction rate. The oxygen may be introduced by any convenient means into the reaction medium in a manner which maintains the dissolved oxygen concentration in the reaction mixture at the desired level. If an oxygen-containing gas is used, it preferably is introduced into the reaction medium in a manner which maximizes the contact of the gas with the reaction solution. Such contact may be obtained, for example, by dispersing the gas through a diffuser such as a porous glass or metal frit (preferably having pores which are no greater than about 20 μm in their largest dimension, and more preferably no greater than about 1 μm in their largest dimension), while shaking or stirring the reactor contents to improve liquid-gas contact and dissolution of the oxygen. Less preferred, although suitable, alternative methods for introducing the oxygen include, for example (1) introducing oxygen into the headspace of the reactor and then drawing it into the reaction mixture using a vortex created by an impeller (this method is sometimes described as a back-mixed operation); or (2) passing the oxygen through a tubular reactor packed with catalyst through which the reaction medium also passes.

To promote selectivity, it is preferable to minimize the amount of undissolved oxygen in the solution, and particularly preferable to minimize the amount of undissolved oxygen which comes into contact with the noble metal catalyst. One way to achieve this is to introduce the oxygen through a membrane which is in contact with the solution. Membranes for bubble-free gas transfer are known in the art.

In a particularly preferred embodiment, the reaction is conducted in a stirred-tank reactor employing a rotating impeller and having oxygen-containing gas bubbles introduced into the reaction solution below the upper surface of the solution. To avoid (or at least diminish) the reduction in selectivity due to the oxygen-containing bubbles, the impeller speed preferably is no greater than the speed necessary to prevent the oxygen-containing bubbles from rising directly to the surface of the solution upon their introduction into the solution. Alternatively, oxygen-containing bubbles may be introduced into the solution at a distance from the impeller such that essentially no bubbles enter the region of the reactor through which the impeller passes, and more preferably such that no bubbles enter the region through which the impeller passes. For example, the oxygen may be introduced just below the upper surface of the liquid and well above the impeller, thereby allowing the bubbles to escape into the headspace rather than forming a gas/liquid turbulent zone around the impeller. The adverse effects of undissolved oxygen also may often be avoided or diminished by introducing oxygen into the reaction mixture in a manner such that no greater than about 10% by volume of the reaction mixture consists of undissolved oxygen. More preferably, no greater than about 4% by volume of the reaction mixture consists of undissolved oxygen, and still more preferably, no greater than about 1% by volume of the reaction mixture consists of undissolved oxygen. The adverse effects of undissolved oxygen in the reaction solution also may often be avoided or diminished by using a noble metal catalyst comprising an electroactive molecular species, as described above. The presence of an electroactive molecular species (particularly N,N'-bis-(3-methylphenyl)-N-N'-diphenyl benzidine) has been found to be especially beneficial for the oxidation of N-methyl glyphosate to glyphosate.

Preferably, the oxidation reaction is conducted at a temperature between about 50 and about 200° C. More preferably, the reaction is conducted at a temperature between about 100 and about 190° C., and still more preferably between about 125 and about 160° C.

The pressure in the reactor during the oxidation depends, in part, on the temperature used. Preferably, the pressure is sufficient to prevent the reaction mixture from boiling. If an oxygen-containing gas is used as the oxygen source, the pressure also preferably is adequate to cause the oxygen to dissolve into the reaction mixture at a rate sufficient to sustain the desired rate of reaction. The pressure preferably is at least equal to atmospheric pressure. More preferably, the oxygen partial pressure is from about 5 to about 500 psig. More preferably still, when the temperature is in the range between about 125 and about 160° C., the oxygen partial pressure is from about 50 to about 200 psig.

The oxidation reaction may be carried out using a wide variety of batch, semi-batch, or continuous reactor systems. Such systems may also include recycling a residual solution remaining after at least a portion of the glyphosate product has been removed from the reaction product mixture. Recycling the residual solution allows any unreacted N-substituted glyphosate to be utilized and enhances recovery of any unprecipitated glyphosate product in the reaction product mixture. To reduce the rate of contaminant build up, a portion of the residual solution may be purged (this purged portion is sometimes referred to as the "waste solution"). The remaining portion (sometimes referred to as the "recycle solution") is recycled back to the oxidation reaction zone. The purging may be achieved by, for example, pressurizing the residual solution and contacting it with a membrane which selectively passes the contaminant to form the waste solution while retaining N-substituted glyphosate and unprecipitated glyphosate product to form the recycle solution. Preferably, the membrane has a molecular weight cutoff of less than about 1,000 daltons and is mechanically stable under the reaction conditions.

Alternatively, the oxidation reaction may be discontinued before complete conversion of N-substituted glyphosate is obtained. According to U.S. Pat. No. 6,232,494, the activity and selectivity of the catalyst tends to decline as the oxidation reaction nears completion. Further, many N-substituted glyphosates (including N-methyl glyphosate and N-isopropyl glyphosate) are more soluble in the aqueous reaction mixture than glyphosate itself, the decline in activity and selectivity can be overcome by removing the product glyphosate before the oxidation is complete. This may be achieved by, for example, removing the catalyst (by, for example, filtration), evaporating a portion of the water in the reaction mixture, and cooling the reaction mixture before there has been less-than-complete conversion. The evaporation and cooling steps precipitate much of the glyphosate product in the solution, thereby facilitating its removal. The residual solution comprising unreacted, -substituted glyphosate is then recycled back to the oxidation reactor.

Preferably, the glyphosate is precipitated and removed when from about 20 to about 95% of the N-substituted glyphosate has been consumed. More preferably, the glyphosate is precipitated and removed when from about 50 to about 90% of the N-substituted glyphosate has been consumed, even more preferably when from about 50 to about 80% of the N-substituted glyphosate has been consumed, and most preferably when from about 50 to about 70% of the N-substituted glyphosate has been consumed. Lower conversions lead to undesirably high recycle rates, whereas greater conversions (as discussed above) are associated with poor catalyst activity and reduced selectivity.

Reactions of Monoethanolamine and Derivatives Thereof

In accordance with a further embodiment of the process, MEA is reacted with a halomethylphosphonic acid to produce HEAMPA. HEAMPA may in turn be converted to glyphosate by known oxidation processes, e.g., by the processes disclosed in U.S. Pat. Nos. 5,627,125, 5,689,000, copending U.S. application Ser. No. 09/547,373 , and U.S. application Ser. No. 09/832,541 (published as No. US-2002-0019564-A1 on Feb. 14, 2002), all of which are expressly incorporated herein by reference in their entirety. For example, HEAMPA may be contacted with molecular oxygen in the presence of a copper catalyst for oxidation of the terminal carbinol moiety to a carboxylic acid group. More generally, a product of Formula IV:

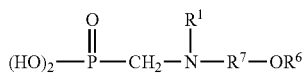

Formula IV or a phosphonic acid ester or salt thereof, can be produced by contacting a halomethylphosphonic acid with an amine reactant of Formula V:

Formula V wherein the halogen substituent of the halomethylphosphonic acid is preferably Cl, Br or I, $R^1$ is hydrogen or substituted or unsubstituted alkyl, alkenyl, alkynyl, aryl, aralkyl, aralkenyl or aralkynyl, $R^6$ is hydrogen or an ether forming moiety, and $R^7$ is alkylene or alkenylene. Preferably $R^7$ is $-(CH_2)_n-$ where n is an integer between 2 and 6. Where $R^7$ is alkenylene it is preferably selected from

—CH=CH—CH$_2$—

—CH$_2$—CH=CH—

—CH$_2$—CH=CH—CH—

—CH=CH—CH$_2$—CH$_2$—

—CH$_2$—CH$_2$—CH=CH— and similar $C_5$ to $C_8$ alkenylene groups, including alkenylene linkages substituted with alkyl substituents.

Generally $R^1$ in Formulae IV and V can be constituted by any of the substituents which can constitute $R^1$ in the compound of Formula I. Any of the alkyl, alkenyl, alkynyl, aryl, aralkyl, aralkenyl and aralkynyl groups which can constitute $R^1$, $R^2$ or $R^3$ of Formula I can also serve as $R^6$ of Formula IV. Preferably, $R^1$ in Formulae IV and V is hydrogen, alkyl or most preferably, hydrogen, methyl, or isopropyl. The value of n is preferably 2.

In one embodiment, the reaction proceeds as follows:

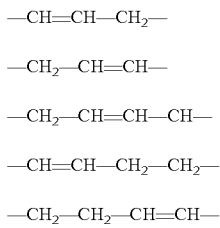

Eq. 2

Preferably the molar ratio of monoethanolamine or other compound of Formula V to halomethylphosphonic acid is at least about 1.5, more preferably at least about 3, still more preferably at least about 5, and most preferably at least about 8. A high ratio of Formula V compound to halomethylphosphonic acid promotes high yield of HEAMPA or other compound of Formula IV, and minimal formation of by-product N,N-bis(phosphonomethyl)ethanolamine or other N,N-bis(phosphonomethyl) derivative.

As in the reactions of glycine and glycine derivatives, the halomethylphosphonic acid is preferably chloromethylphosphonic acid.

Reaction can be conducted at elevated temperature in a reaction system comprising water and/or other polar organic solvent, e.g., dimethylformamide, acetonitrile, glycols such as ethylene glycol, glycol ethers such as tetraethylene glycol monomethyl ether or tetraethylene glycol dimethyl ether, a crown ether, preferably comprising three to about eight $C_2$ or $C_3$ alkylene units (e.g., 18-crown-6, 15-crown-5, or 12-crown-3), primary alcohols such as methanol, polyols such as glycerol, polyvinyl alcohol, pentaerythritol and reduced sugars, and mixtures of one or more of these organic solvents with water. It has been observed that some solvents, while useful, tend to increase the degree of overalkylation of the amine reactant, i.e. to the N,N-bis(phosphonomethyl) species. This tendency has been observed in solvents such as dimethylformamide, acetonitrile and glycol ethers. However, a favorable effect on yields has been observed in the use of certain other surfactants, especially mixtures of glycerol and water. A 10% to 20% by weight solution of glycerol in water has been found particularly advantageous.

As in the reactions of glycine and glycine derivatives, the reaction is preferably conducted in an alkaline reaction medium. Preferably, the base is an alkali metal hydroxide, most preferably NaOH or KOH, and is present in a ratio of at least about 1.5 moles base per mole halomethylphosphonic acid. More preferably, base is charged to the reaction medium in a ratio of at least about 2 moles per mole halomethylphosphonic acid, more preferably in a ratio of at least about 3. Optionally, other bases can be present in addition to, or in lieu of an alkali metal hydroxide such as, for example, alkaline phosphate salts and hydroxides of countercations such as substituted ammonium, phosphonium, sulfonium or sulfoxonium, and mixtures thereof.

The proportion of water present also has a significant effect on the HEAMPA yield. Preferably, water is charged to the reaction medium in a ratio of at least about 25 moles, more preferably at least about 40 moles, per mole halomethylphosphonic acid. Total water content of the reaction medium is preferably at least about 35% by weight, more preferably at least about 45% by weight. Alternatively, however, the reaction may be run under substantially anhydrous conditions to facilitate product recovery and recycle of unreacted amine reactant, as described in further detail hereinbelow.

The reaction may be conducted at a temperature between room temperature and 150° C., preferably between 70° and 120° C., more preferably between about 75° and about 105° C.

The reaction may be promoted by the presence of additives that are the same or similar to those described above for the reaction of a halomethylphosphonic acid with the amine reactant of Formula III. The contemplated mechanisms and proportions of such additives, promoters, and catalysts are substantially the same as described for the preparation of the compounds of Formula I.

Where the reaction is conducted in a medium comprising only an organic solvent, NaCl or other salt by-product of the reaction may precipitate during the reaction. For example, the process may be conducted in a substantially anhydrous reaction system to which substantially anhydrous alkali metal hydroxide is charged to promote the reaction. The salt is preferably removed by filtration or centrifugation prior to recovery of the product of Formula IV. To facilitate recovery of the product from a reaction mixture comprising an aqueous solvent system, it may first be desirable to concentrate the resulting solution to precipitate the by-product salt.

Where the reaction is conducted with an excess of monoethanolamine or other compound of Formula V relative to the charge of halomethylphosphonic acid, recovery of the product further requires removal of the unreacted Formula V compound contained in the reaction mixture. If an aqueous solvent is used for the reaction, unreacted Formula V compound may conveniently be removed by extraction with a water-immiscible solvent such as methylene dichloride. Solvents other than methylene dichloride which are effective for the extraction include lower alkyl esters of low molecular weight organic acids, e.g., ethyl acetate or butyl acetate. Conveniently, the extract may be distilled to separate the compound of Formula V from the extraction solvent, with the former being recycled to the reaction step and the latter to the extraction step. Distillation may also produce an appropriate purge fraction for removal of impurities, or the impurities may be removed by purging or further processing of the recycle amine reactant or the recycle solvent, or both.

Alternatively, ethanolamine or other compound of Formula V may be distilled from the reaction mixture. Where an organic solvent is used for the reaction, by-product salt is preferably removed first, and the filtered reaction mixture is distilled for removal of both solvent and unreacted compound of Formula V. Solvent and unreacted compound of Formula V may be recovered in a mixed condensate and recycled to the reaction step, with appropriate purge to remove impurities. Optionally, solvent may be separated from compound of Formula V either in the same distillation system in which both are removed from the filtered reaction mixture, or in a subsequent distillation. As in the distillation of a solvent extract, further distillation may produce a concentrated purge stream for removal of impurities with minimum loss of solvent and/or compound V.

Raffinate from the extraction of the filtered reaction mixture, or the residue of a distillation step, contains the product of Formula IV. The compound of Formula IV may be recovered by further processing of the raffinate or residue in any convenient manner known to those skilled in the art. Optionally, the raffinate or distillation bottoms stream may be used directly as a reactor feed stream for further reaction of the compound of Formula IV in the preparation of other products. For example, where the compound of Formula IV comprises HEAMPA or a salt or ester thereof, it may be directly oxidized to glyphosate or a glyphosate salt or ester, e.g., by reaction with molecular oxygen in the presence of a copper catalyst as by the processes disclosed in the references incorporated elsewhere herein: U.S. Pat. No. 5,627,125, U.S. Pat. No. 5,689,000, copending U.S. application Ser. No. 09/547,373, and U.S. application Ser. No. 09/832,541 (published as No. US-2002-0019564-A1 on Feb. 14, 2002)

Recovery Schemes for MEA Reactions

Figure 5:
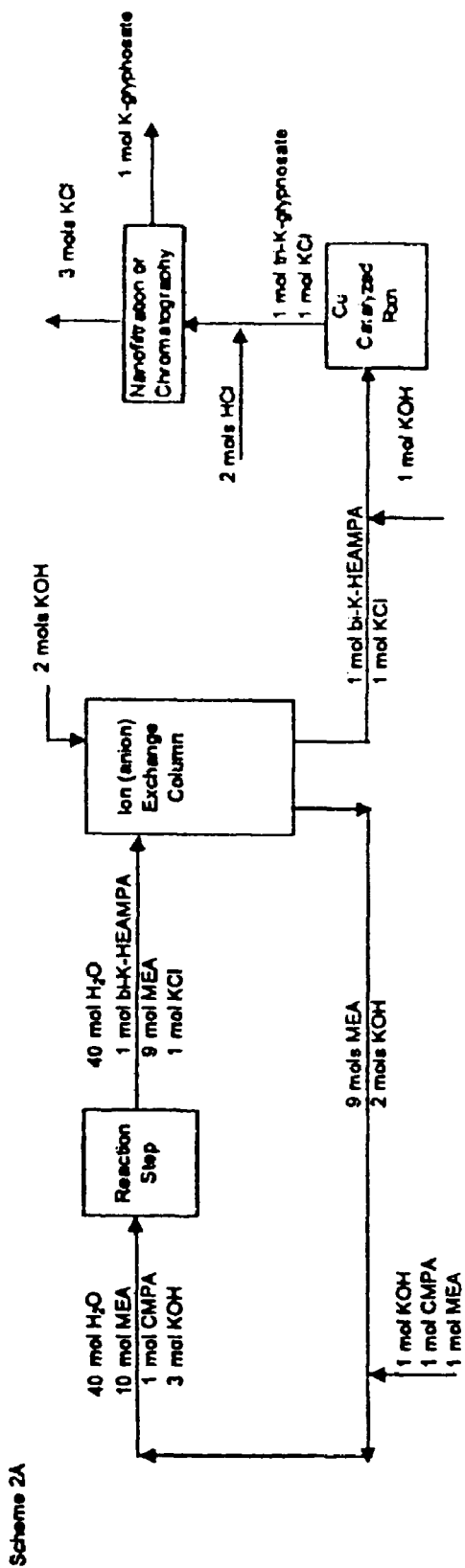

Illustrated in FIG. 5 is a preferred embodiment of the invention for recovery of an alkali metal salt of HEAMPA from an aqueous mixture obtained by reaction of a halomethylphosphonic acid (CMPA) or salt thereof with monoethanolamine (MEA) in the presence of base. Specifically illustrated is a process in which the base is KOH. In the process of FIG. 5, HEAMPA or N-substituted HEAMPA salt recovered from the reaction mixture is converted to glyphosate or N-substituted glyphosate salt by catalytic dehydrogenation.

In the embodiment of the process as illustrated, the starting reactants are charged in a MEA to CMPA molar ratio of 10:1 together with water in molar ratio to MEA of 4:1. The reaction mixture contains dipotassium HEAMPA (1 mole), MEA (9 moles), KCl (1 mole) and water (40 moles). An aqueous product recovery feed mixture comprising or derived from the reaction mixture is charged to an anion exchange column containing a resin selected to hold up HEAMPA. As ion exchange progresses, the column is preferentially loaded with Cl$^-$ and(K HEAMPA)$^-$ ions. MEA passes through the column producing a column effluent depleted in HEAMPA and containing MEA, which is preferably recycled to the reaction zone to serve as an amine reactant for reaction with a further supply of CMPA. The loaded column is eluted with an aqueous KOH solution (2 moles KOH; 40 moles water) to produce an eluate containing dipotassium HEAMPA (1 mole), KCl (1 mole) and water (40 moles).

Further base may be introduced into the eluate to produce a dehydrogenation reaction feed mixture that is introduced into a dehydrogenation reaction zone where it is contacted with a dehydrogenation catalyst, thereby converting hydroxyethylaminomethylphosphonic acid anion or N-substituted hydroxyethylaminomethylphosphonic acid anion to glyphosate anion or N-substituted glyphosate anion. In accordance with the teaching of the incorporated references, dehydrogenation is preferably conducted in the presence of a strong base having a pKa value of at least about 11, more preferably at least about 12, and even more preferably at least about 13. Suitable bases include, for example, alkali metal hydroxides (LiOH, NaOH, KOH, RbOH, or CsOH), alkaline-earth metal hydroxides (e.g., Mg(OH)2 or Ca(OH)2), NaH, and tetramethyl ammonium hydroxide. Of these bases, alkali metal hydroxides (particularly NaOH and KOH) are often preferred because of their solubility in water under the reaction conditions, as well as their ready commercial availability and ease of handling. For the dehydrogenation of HEAMPA, KOH is a particularly preferred base.

The preferred amount of base introduced into the reaction zone depends on, for example, the moles of primary alcohol groups introduced into the reaction zone. Preferably, at least about one molar equivalent of base is introduced per mole of primary alcohol hydroxy groups. In the preferred embodiment of FIG. 5, 1 mole of KOH is added per mole of HEAMPA product to produce a dehydrogenation reaction feed mixture.

Dehydrogenation is preferably catalyzed with a metal catalyst. Copper catalysts are preferred, e.g., Cu on a carbon support as described in U.S. Pat. Nos. 5,627,125 and 5,689,000 or a Cu sponge catalyst as described in copending U.S. application Ser. No. 09/547,373 and U.S. Application Publication US-2002-0019564-A1. The preferred catalyst loading (i.e. the preferred amount of catalyst introduced into the reaction zone) depends on, for example, the amount of HEAMPA charged into the reaction zone. On sponge substrates, catalytic Cu is preferably present in the reaction zone in a proportion of at least about 1% by weight of HEAMPA. More preferably, the catalyst loading is from about 1 to about 70% and still more preferably from about 10 to about 40% by weight of the HEAMPA.

The preferred catalyst loading also depends on, for example, the amount of total reaction mass. Typically, the catalyst loading is at least about 0.1% by weight of the total reaction mass. More preferably, the catalyst loading is from about 0.1 to about 10%, even more preferably from about 3.5 to about 10%, and still even more preferably from about 3.5 to about 5% by weight of the total reaction mass. Concentrations of greater than about 10 wt. % are difficult to filter. On the other hand, concentrations of less than about 0.1 wt. % tend to produce unacceptably low reaction rates.

The references describe dehydrogenation temperatures between about 70° C. and about 250° C. For a carbon-supported Cu catalyst the temperature preferably ranges between about 100° C. and about 190° C. and more preferably between about 140° C. and about 180° C. For a Cu sponge catalyst the temperature preferably ranges between about 120° C. and about 220° C., more preferably between about 140° C. and about 200° C., and still more preferably between about 145° C. and about 155° C.

Pressure in excess of atmospheric pressure is normally but not always required to proceed at suitable rate at the temperatures indicated above. Generally it is necessary to exceed the minimum pressure at which the reaction proceeds in the liquid phase. For carbon-supported Cu catalyst processes, the reaction pressure in the headspace above the liquid reaction mixture is preferably between about $1.96 \times 10^5$ Pascals and about $2.94 \times 10^5$ Pascals, more preferably between about $4.90 \times 10^5$ Pascals and about $1.96 \times 10^6$ Pascals. For Cu sponge processes, the reaction pressure in the headspace above the liquid reaction mixture is at least about $4.90 \times 10^5$ Pascals, more preferably between about $4.90 \times 10^5$ Pascals and about $2.94 \times 10^6$ Pascals, even more preferably between about $4.90 \times 10^5$ Pascals and about $1.96 \times 10^6$ Pascals, still even more preferably between about $7.85 \times 10^5$ Pascals and about $1.08 \times 10^6$ Pascals, and most preferably about $9.22 \times 10^5$ Pascals. Although greater pressures may be used, they are normally less desirable because they tend to reduce the reaction rate.

Dehydrogenation is preferably conducted under a non-oxidizing atmosphere to avoid oxidation of the catalyst surface, more preferably under an atmosphere containing a noble gas and/or $N_2$, and even more preferably under $N_2$ when the reaction is conducted on a commercial level. Because the dehydrogenation reaction proceeds with the liberation of hydrogen, the atmosphere will also contain gaseous hydrogen, which is preferably vented with care from the pressurized reaction vessel. The venting may be monitored to determine the rate and the completeness of the reaction.

In a preferred embodiment, the headspace above the reaction mixture is filled with a non-oxidizing gas at atmospheric pressure. Reactants and catalyst are charged to the reactor, and the reaction mixture temperature is maintained at reaction temperatures described elsewhere herein while the reactor pressure is allowed to increase autogenously until a desired reaction pressure is achieved in the reactor. The headspace is thereafter vented to control the reactor pressure at this desired reaction pressure until the reaction nears completion as the rate of hydrogen gas generation decreases.

The dehydrogenation reaction may be carried out in a wide variety of batch, semi-batch, and continuous reactor systems. Suitable conventional reactor configurations include, for example, stirred-tank reactors, fixed bed reactors, trickle bed reactors, fluidized bed reactors, bubble flow reactors, plug flow reactors, and parallel flow reactors. Often, the more preferred reactor configurations are stirred-tank reactors.

When the dehydrogenation is conducted in a continuous reactor system, the residence time in the reaction zone can vary widely depending on the specific catalyst and conditions employed. Likewise, when the dehydrogenation is conducted in a batch reactor, the reaction time typically will also vary widely depending on such factors. Normally, the dehydrogenation behaves as a first order reaction, particularly toward the end of the reaction. Thus, the preferred residence time in a continuous reaction zone (or the preferred reaction time in a batch reaction zone) will also depend on the desired degree of conversion.

In an embodiment according to FIG. 5, the dehydrogenation reaction mixture contains tripotassium glyphosate (1.0 mole), KCl (1.0 mole) and a sufficient amount of water to run the reaction (for example, about 40 moles). A mineral acid, preferably HCl (2.0 moles) in water (7 moles), is introduced into the dehydrogenation reaction mixture to produce a neutralized dehydrogenation reaction mixture comprising monopotassium glyphosate (1.0 mole), KCl (3.0 moles) and water (47 moles). Water is added and KCl is removed from the neutralized dehydrogenation reaction mixture by nanofiltration, producing a filtrate comprising KCl (3.0 moles) and water (78 moles) and a halide-depleted retentate comprising monopotassium glyphosate (1.0 mole) and water (9 moles). Alternatively, KCl may be separated from the neutralized dehydrogenation reaction mixture by ion chromatography. The retentate produced by nanofiltration, or the monopotassium glyphosate eluate from the ion chromatographic medium, constitutes a product solution useful as an herbicide or herbicide concentrate.

In an alternative embodiment of the process of FIG. 5, an aqueous product recovery feed mixture comprising or derived from the reaction mixture is contacted with a chromatographic medium that is relatively selective for HEAMPA, an HEAMPA salt, an N-substituted HEAMPA, or N-substituted HEAMPA salt versus unreacted amine constituents of the product recovery feed mixture. The aqueous mixture is caused to flow through a bed or column comprising the ion exchange resin. Passage of HEAMPA or N-substituted HEAMPA species through the bed or column is retarded relative to the flow of the aqueous phase containing MEA or N-substituted MEA. An aqueous effluent is thereby produced containing MEA or N-substituted MEA, which is preferably recycled to the reaction zone. The chromatographic medium is thereafter contacted with an aqueous alkaline eluant to produce an eluate comprising HEAMPA, HEAMPA salt, N-substituted HEAMPA or N-substituted HEAMPA salt. The remainder of this embodiment of the process is as shown in FIG. 5 and described above.

Figure 6:
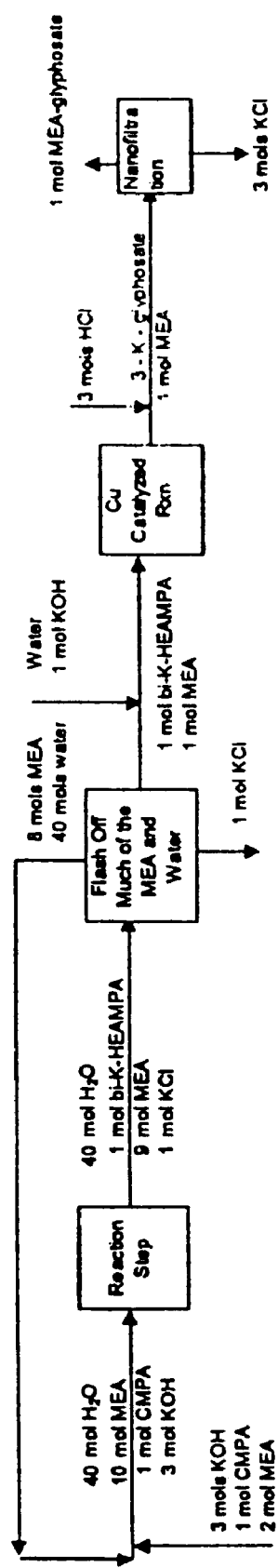

Illustrated in FIG. 6 is an alternative process for recovery of HEAMPA or N-substituted HEAMPA salt from the reaction mixture obtained by reacting MEA with CMPA, and conversion of the HEAMPA or N-substituted HEAMPA salt to a salt of glyphosate or N-substituted glyphosate. In the process of FIG. 6, MEA (10 moles), CMPA (1 mole), KOH (3 moles) and water (40 moles) are charged to the reaction zone and reacted in the manner described hereinabove to produce a reaction mixture containing dipotassium HEAMPA (1 mole), unreacted MEA (9 moles), KCl (1 mole) and water (40 moles). A product recovery feed mixture comprising or derived from the reaction mixture is introduced into an evaporator or distillation unit where water (40 moles) and MEA (8 moles) are removed as a vapor stream which is recycled to the reaction zone, either as a condensate or in the vapor phase as a heat source for bringing the reactor charge to the desired temperature for the reaction. KCl (1 mole) is removed as a precipitate, leaving a concentrate comprising HEAMPA, an HEAMPA salt, N-substituted HEAMPA, or an N-substituted HEAMPA salt. An aqueous base, e.g. KOH (1 mole), is then introduced into the concentrate to produce an alkaline concentrate containing the dipotassium salt of HEAMPA (1 mole) and MEA (1 mole) and a sufficient amount of water to perform the dehydrogenation reaction.

The alkaline concentrate is then contacted with a dehydrogenation catalyst in a reaction system which has been optimized for minimal dehydration of MEA to convert HEAMPA to a glyphosate salt. Any glycine produced from the reaction may be handled according to the separation schemes represented in FIGS. 1-4. The resultant aqueous dehydrogenation reaction mixture comprises $K_3$ glyphosate (1 mole), and MEA (1 mole). HCl (3 moles) is added in water (10.5 moles) to the dehydrogenation reaction mixture to produce an aqueous neutralized dehydrogenation reaction mixture that contains glyphosate anion (1 mole), MEA (1 mole), and KCl (3 moles). The neutralized dehydrogenation reaction mixture is subjected to nanofiltration to produce a filtrate comprising KCl (3 moles) and water (preferably more than 75 moles), and a halide depleted retentate comprising the monoethanolamine salt of glyphosate (1 mole) and water (12 moles).

In a further alternative embodiment of FIG. 6, the catalyst used for the dehydrogenation is not sufficiently selective to prevent dehydrogenation of MEA to glycine. In this instance, the glycine produced in the dehydrogenation step is converted to glyphosate by reaction with additional CMPA. For this purpose a final reaction feed mixture comprising glyphosate salt and glycine contained in the dehydrogenation reaction mixture is introduced into a final reaction zone wherein CMPA reacts with glycine to produce additional glyphosate. The final reaction feed mixture comprises the dehydrogenation reaction mixture, neutralized dehydrogenation reaction mixture, or other aqueous mixture derived from the dehydrogenation reaction mixture. To minimize formation of glyphosine in the final reaction step, the final reaction is conducted in final reaction system comprising a plurality of reaction stages arranged in series with respect to the flow or transfer of reaction mixture containing glycine. The supply of CMPA is distributed among the series of stages so that each stage except the last stage comprises an excess of glycine with respect to CMPA, thereby enhancing the rate of consumption of CMPA in reaction with glycine to glyphosate versus the competing reaction with glyphosate to glyphosine. Halide salt is thereafter removed from the final reaction mixture, as by the nanofiltration or ion chromatography operations described above, to produce a final product solution of glyphosate salt that is useful as an herbicide.

Glyphosine produced in the final reaction step may be separated from the final reaction mixture and oxidized to produce additional glyphosate and formylphosphonic acid. Similar oxidizing processes are described in U.S. Pat. No. 6,218,570. Glyphosate is separated and combined with that which has been obtained by separation of glyphosine from the final reaction product mixture. Furthermore, if desired, the formylphosphonic acid may be used in the reductive alkylation of glycine to produce additional glyphosate. Significantly, these processes provide an avenue to operate a reaction of glycine with CMPA at molar ratios as low as 1:1.

As discussed elsewhere herein, the ratio of MEA to CMPA in the processes of FIGS. 5 and 6 can be significantly lower than the 10:1 ratio described immediately above. As also discussed elsewhere herein, the water/MEA and water/CMPA ratios can be adjusted to increase or decrease the degree of dilution. The KOH/MEA ratio may also be adjusted as discussed herein. The compositions of other process streams vary with the MEA/CMPA ratio, water/CMPA ratio and KOH/MEA ratio in accordance with the dictates of the material balance.

The processes of the present invention allow the preparation of glyphosate, a glyphosate salt or ester, or a glyphosate precursor, without producing stoichiometric equivalents of carbonaceous by-products. In contrast to conventional processes for the manufacture of glyphosate, the processes of the invention do not require the preparation of an N-phosphonomethyl tertiary amine intermediate from which an acetic acid moiety must be cleaved by oxidation. As a result, no waste by-product formaldehyde, formic acid and/or carbon dioxide is produced, and the process of the invention can achieve relatively high yields on ethylene oxide or other ultimate source of the two carbons of the glycine moiety of glyphosate.

Unlike the conventional process that is based on the phosphonomethylation of disodium iminodiacetic acid, the process of the invention does not produce three moles of NaCl by-product per mole of glyphosate produced. Favorable yields based on CMPA substrate are achieved by using a substantial excess of amine reactant which can be recovered and recycled to the reaction zone, e.g., in a continuous process for the preparation of HEAMPA or glyphosate.

Preparation of Triphosphonomethylamine

CMPA may also be reacted with ammonia, ammonium hydroxide or other ammonia source to produce triphosphonomethylamine, a sequestrant useful in various known applications and sold under the trade designation "Dequest." Except for the reactant ratios employed, conditions for the reaction are substantially similar to those described above for the reactions of glycine, Na glycinate and/or MEA with CMPA. In order to achieve triphosphonomethylation, it is desirable to use a proportion of CMPA at least substantially stoichiometrically equivalent to ammonia, i.e., at least about 3 moles CMPA, but preferably not more than about 3.5 moles CMPA, per mole ammonia. At the stoichiometrically equivalent 3:1 ratio, the reaction product contains approximately 20 to 40 mole % monophosphonomethylamine, approximately 20 to 40 mole % diphosphonomethylamine, and approximately 20 to 40 mole % triphosphonomethylamine. At higher ratios of CMPA to ammonia source, the fraction of triphosphonomethylamine can be increased. The primary and secondary amine products can be separated from the reaction mixture and recycled to the reaction zone if desired to produce additional triphosphonomethylamine. Alternatively, the monophosphonomethylamine can be reacted with a reagent such as monochloroacetic acid to produce glyphosate.

Reactions of Hydroxymethyl Phosphonic Acid

It has further been discovered that an amine compound such as glycine, iminodiacetic acid or monethanolamine can be reacted with hydroxymethylphosphonic acid to produce glyphosate, HEAMPA or derivatives thereof. In certain preferred embodiments of these processes, hydroxymethylphosphonic acid ("HMPA") or a source thereof is reacted with the amine compound substrate in a ratio of at least about 1.5 moles substrate per mole HMPA. The process is applicable to the preparation of glyphosate acid, salts of glyphosate, esters of glyphosate, HEAMPA acid, HEAMPA salts, and esters and ethers of HEAMPA.

HMPA may also be reacted with ammonia or an ammonia source to produce triphosphonomethyl amine.

Reaction of HMPA with Glycine or Glycine Derivative

In the preparation of glyphosate or its salts, HMPA can be reacted with a glycine acid salt such as glycine hydrochloride or with a glycinate salt such as an alkali metal glycinate. Glycine may also be charged to a glycine/HMPA reaction system in the free base form. More generally, a compound corresponding to Formula I, above, or a salt or phosphonic ester thereof, can be produced by reacting HMPA with an amine compound of Formula III, above. Substituents in Formulae I and III are as defined above with reference to the reactions of halomethylphosphonic acids with glycine derivatives. Alternatively to reaction with a compound of Formula III, HMPA may be reacted with a dimer, oligomer, or polymer of the compound of Formula III.

The reaction between HMPA and a monomer of Formula III proceeds in the following manner where the substrate of Formula III comprises a glycinate or other carboxylate salt:

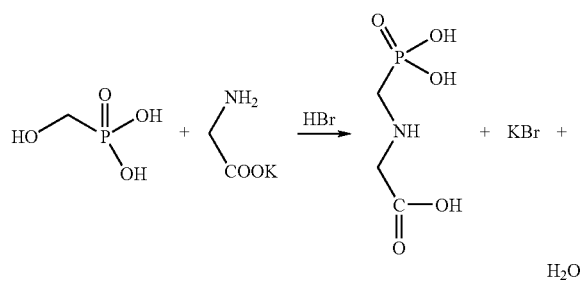

Reaction of glycine hydrochloride involves addition of a strong base, and is believed to proceed as follows:

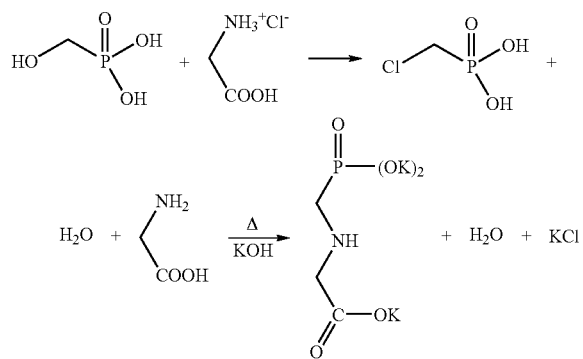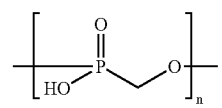

In the latter reaction, contacting the amine hydrochloride salt with HMPA is believed to cause intermediate formation of CMPA and glycine free base. CMPA and glycine are then reacted in the presence of a strong base such as KOH or NaOH to yield a salt of glyphosate.

Regardless of the selection of amine substrate, the reactants are preferably charged to the reaction zone in a ratio of moles of glycine or glycinate substrate per mole HMPA of at least about 3, more preferably at least about 5, most preferably at least about 10. As in the case of the reactions of halomethylphosphonic acids, the operation at relatively high amine compound to HMPA ratio is effective to enhance conversion of HMPA with minimal formation of glyphosine or related species, and thus to provide reasonable yields based on HMPA. As in the process based on the reactions of halomethylphosphonic acid, unreacted glycine, glycine acid salt, glycinate or other amine compound can be recovered from the reaction mixture and recycled, providing ultimately high yields on the amine compound substrate.

Where the amine compound substrate is an N-substituted glycine derivative, i.e., a compound of Formula III wherein $R^1$ is other than hydrogen, it is possible to achieve significant conversion of HMPA at relatively low amine/HMPA ratios, and without excessive formation of glyphosine or other N,N-bis-(phosphonomethyl) species. For example, bis(phosphonomethyl) by-product formation remains minimal at an amine/HMPA ratio of 3 or even lower, though ratios of at least about 5 are more effective for conversion of HMPA. As discussed below, conversion may in some instances be enhanced by the presence of a catalyst. If the catalyst can be selected to provide reasonable conversions, the reaction may preferably be conducted on a substantially equimolar basis, advantageously reducing the requisite extent of amine reactant recycle and reducing the load on post-reaction separation processes.

In the reactions of HMPA, as in the case of the reactions of halomethylphosphonic acids, the $R^1$ substituent of amine substrate of Formula III is preferably hydrogen, methyl, isopropyl or carboxymethyl (hydroxycarbonylmethyl), $R^4$ preferably corresponds to Formula II, and $R^5$ is preferably hydrogen, alkali metal, isopropylammonium, or dimethylsulfonium. Most preferably, the compound of Formula III is glycine (or its hydrochloride), an alkali metal glycinate, iminodiacetic acid (or its hydrochloride), or an iminodiacetic acid salt such as disodium iminodiacetic acid.

In various preferred embodiments of the invention, the reaction is conducted within a medium into which HMPA is introduced in the form of a self-ester dimer, trimer or oligomer, or HMPA. It has been discovered that a HMPA self-ester dimer, trimer or oligomer is more reactive than HMPA monomer with an amine substrate such as glycine or glycinate. Whether in monomer, dimer or oligomer form, the HMPA is preferably substantially anhydrous.

An HMPA self-ester oligomer typically corresponds to the formula:

where typically n is 2 or greater. As provided, an HMPA self-ester reagent typically comprises a mixture of HMPA monomer, dimers and oligomers. As discussed below, the oligomers may also be crosslinked by —P—O—P— linkages, which are generated by condensation of phosphonyl groups of adjacent HMPA monomers or oligomer chains. The melting point of the self ester mixture is generally in the range of about 90° C. to about 200° C.

The self ester oligomers may be prepared by dehydration of neat (100%) HMPA or an aqueous solution thereof. A process for dehydrating HMPA is described by Petrov, et al., *Khim. Elementorg. Soed.* (1976), pp. 200-204. In this process HMPA is dehydrated at relatively high temperature, e.g., 180° to 220° C. at 40 to 50 mm Hg. The Petrov article further describes reaction of the dehydrated HMPA with aniline or benzyl amine. Generally, it has been found that HMPA can be dehydrated at temperatures in the range of 100° to 200° C. and pressures of 1 to 70 mm Hg.

In a particularly advantageous embodiment, it has been found that HMPA can be dehydrated at low temperature and pressure, e.g., 100° to 120° C. and 0.5 to 5 mm for one to two hours, or by azeotropic distillation with toluene, xylene, mesitylene, or other solvents that form an azeotrope with water at temperatures in the range of 100° to 170° C. Adequate dehydration by azeotropic distillation can ordinarily be accomplished within 5 to 16 hours to yield the dimeric, trimeric and oligomeric self esters. Where obtained by azeotropic distillation with mesitylene (b.p. 164° C.), for example, the dehydrated HMPA comprises oligomeric and polymeric derivatives of the self-ester dimer of Formula VI. Such oligomeric and polymeric derivatives contain —O—P—O—CH$_2$—P— repeating units and may further comprise branching or crosslinking groups having an —O—P—O—CH$_2$—P— or —P—O—P— structure. Such oligomeric derivatives may comprise symmetric branching chain forms corresponding to Formula VIA:

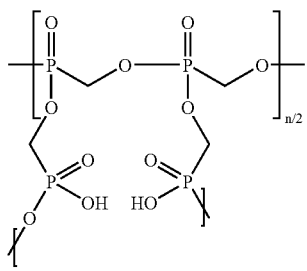

as well as asymmetric branching chain forms corresponding to Formula VIB:

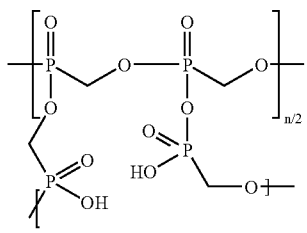

Dehydration of HMPA may also yield the linear and cyclic dimer of HMPA such as for example:

Formula VI

Formula VIC

Formula VID

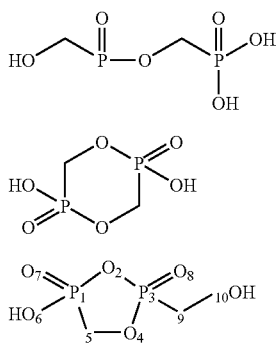

The product of the azeotropic dehydration may comprise a mixture of linear chains of Formula VI, symmetric branched chains of Formula VIA, asymmetric branched chains of Formula VIB, and either of the cyclic dimers of Formulae VIC and/or VID. Where dehydration is conducted simply under vacuum, the principal dehydrated species may be the linear dimer, and a significant fraction of "free" or monomeric HMPA may remain. Where dehydration is conducted in the presence of an azeotroping solvent, most of the monomeric HMPA can be converted to dimers, trimers and oligomers. For example, azeotropic distillation in the presence of xylene may typically yield a dehydrated HMPA composition that is a viscous syrup under ambient conditions, and which contains not more than about 10% or 20% linear dimer and the rest substantially trimers, oligomers, and cyclic dimers, with significantly reduced residual monomer content. Azeotropic distillation in the presence of mesitylene may produce a dehydrated HMPA composition that is solid at room temperature, and contains only a trace of linear dimer. The exact mix of linear oligomers of varying length, symmetric branched chain oligomers, asymmetric branched chain oligomers, cyclic dimers and cross-linked oligomers is not known, but can vary widely depending on the time, temperature, pressure and other conditions of the azeotropic distillation. Generally, however, where the dehydrated HMPA is produced by azeotropic distillation, the proportion of linear species wherein n<3 is typically not greater than about 20 wt. %, more typically not more than about 10 wt. %. The melting point of such derivatives is typically in the range between about 90° and about 200° C.

Reaction of dehydrated HMPA (self esters) with an amine substrate is preferably carried out at relatively elevated temperature, e.g., 125° to 200° C., more typically 150° to 200° C. The reaction may be conducted neat, i.e., in an HMPA/amine melt, or in a non-aqueous polar solvent such as sulfolane, a crown ether acetonitrile or anisole. Preferred charge ratios are as discussed above. A solvent may be useful in reducing the viscosity of the reaction medium, thereby enhancing heat transfer and minimizing concentration gradients. However, somewhat higher payloads may be realized where the reaction is conducted in a molten reaction medium substantially devoid of solvent other than water produced by the reaction. According to a further option, a solvent may be used in preparation of a homogeneous mixture of dehydrated HMPA and amine substrate, and then evaporated off at an elevated temperature at which the neat mixture of dehydrated HMPA and amine substrate is a liquid of reasonable viscosity. In this manner, a solvent may contribute to the operation of the process without diluting the reaction medium and reducing payload.

Water is a product of the reaction. Optionally, water may be removed from the reaction medium as the reaction proceeds, which may help to drive the reaction in the forward direction. In any event, water from extraneous sources is preferably substantially excluded, i.e., the reaction medium is maintained substantially free of moisture from any source other than water produced in the reaction between the amine reactant and hydroxymethylphosphonic acid monomer, dimer, trimer or oligomer.

Where the substrate comprises a carboxylate salt or amino acid free base, the reaction is initially conducted under alkaline conditions. Where the amine substrate as charged to the reaction medium comprises an alkali metal salt of an amino acid, the reaction may proceed effectively in the absence of any other base; but where the substrate as charged comprises a substantial fraction of glycine free base, it is generally necessary to add a strong base to promote the initial step of reaction. This procedure is essentially equivalent to charging a glycinate salt rather than the free base. As described below, the initial reaction under alkaline conditions produces an intermediate which is then subjected to acid hydrolysis to form the desired phosphonomethylated amine product of Formula I.

Where the substrate as charged comprises substantially the amine acid salt, such as glycine hydrochloride, it is believed that the reaction may typically proceed in two successive steps. According to such mechanism, glycine hydrochloride is first reacted with HMPA or HMPA source to produce an intermediate reaction mixture. The intermediate reaction mixture is then contacted with base to produce the desired phosphonomethylamine product of Formula I. As illustrated in the proposed reaction equation as set forth above (but without being held to any particular theory), it is believed that an amine acid salt such as glycine hydrochloride initially reacts with HMPA to form the halomethylphosphonic acid such as CMPA and the amine free base. The amine free base is then believed to react with halomethylphosphonic acid in the presence of another base to yield the desired phosphonomethylated product, such as glyphosate.

Optionally, the reaction with either the carboxylate salt or the amine acid salt of the substrate may be carried out in the presence of an additive such as bromide ion or iodide ion. In such embodiments, it is believed that the halide ion may undergo a reversible exchange with the hydroxyl of an HMPA molecule, forming a halomethylphosphonic acid which is generally more reactive with the amine substrate than HMPA itself, in which case it may be the halomethylphosphonic species which actually condenses with the amine moiety of the substrate, thereby regenerating the halide ion for reversible exchange with another HMPA molecule. In turn, this results in further condensation with the amine and continuing regeneration of the halide. As noted above, where the amine substrate comprises an amine acid salt, e.g., glycine hydrochloride, a Br$^-$ or I$^-$ ion may undergo a reversible exchange with the chlorine substituent of the intermediate CMPA, thus promoting the reaction in substantially the manner described hereinabove with respect to the reactions of halomethylphosphonic acids and amine substrates. The halide ion additive may conveniently be supplied in the form of an alkali metal salt, such as NaI, KI, KBr, etc. Where a halide ion additive is used, it is preferably present in the reaction mixture in molar excess with respect to the concentration of equivalent HMPA throughout the reaction cycle; and, in the case of a batch reaction system, is preferably in molar excess with the respect to the cumulative charge of equivalent HMPA to the reaction medium. Typically, the ratio of iodide ion equivalents to HMPA equivalents is at least about 1.2, more typically at least about 1.5. Higher ratios in the range of 2 or higher may also be useful.

Optionally, other additives such as Lewis acids, etc., may also be incorporated into the reaction medium during the initial contact of dehydrated HMPA and amine substrate, substantially as described above with reference to the reactions of halomethylphosphonic units and amine reactants.

Where the reaction is conducted in a batch mode with a primary amine substrate such as Na glycinate or K glycinate, excess amine reactant and anhydrous HMPA are charged to a reaction vessel in the preferred ratios stated above. In a reaction medium comprising glycinate or substituted glycinate and polar solvent, the initial concentration of anhydrous HMPA in is preferably at least about 2 wt. %, more preferably at least about 3 wt. %. Where reaction is conducted in the melt, in the absence of a polar solvent, the initial concentration of HMPA is preferably at least about 5 wt. %, more typically at least about 10 wt. %. Where the amine substrate comprises a secondary amine such as sarcosine or N-isopropylglycine, it may be feasible to operate at lower amine/HMPA ratios, and thus at significantly higher initial HMPA concentration.

At temperatures in the above noted range of about 150° to about 200° C. batch reaction cycles are typically in the range between about 2 hours to about 100 hours, more typically about 3 hours to about 10 hours.

Because the reaction is preferably conducted with a substantial excess of amine reactant, it may advantageously be conducted in a continuous mode. Either a continuous stirred tank or flow reactor may be used, generally for the same reasons as discussed above with respect to the reactions of halomethylphosphonic acids with Na glycinate.

Reaction of HMPA self-ester oligomer with either amine free base or a carboxylate or N-substituted carboxylate salt produces an intermediate, the structure of which is not fully understood. Once conversion of HMPA is substantially complete, the intermediate reaction product may be hydrolyzed to form the desired phosphonomethylated reaction product of Formula I. Hydrolysis is conveniently effected by addition of an aqueous acid to the reaction mixture. Hydrohalide acids such as hydrobromic or hydrochloric are suitable for this purpose. Where the amine compound substrate is a carboxylate salt, e.g., an alkali metal or ammonium salt, the product of the hydrolysis is an aqueous solution of the desired product. Depending on the pH of the hydrolysis reaction mixture, the product may be present in any of various forms, e.g., zwitterion, amine acid salt, or carboxylate salt. Preferably, a substantial excess of mineral acid is added for purposes of the hydrolysis, so that the product of the hydrolysis is predominantly in the form of the amine acid salt.

For example, a mineral acid may typically be added in an excess of 2 equivalents per total amine equivalents in the reaction mixture, more preferably in excess of 4 equivalents per total amine equivalents. If a hydrohalide acid is introduced, its concentration as delivered may be in the range of about 5 to about 30 wt. %, typically in the range of about 10% to saturation. Hydrolysis is conveniently conducted at a temperature between about 70° and about 160° C., more typically between about 90° and about 130° C., more preferably between about 100° and about 120° C.

Where the initial substrate is an amine acid salt, such as glycine hydrochloride, the initial reaction of the amine salt and HMPA is typically conducted within the same range of temperature conditions, and at the same preferred ratios of amine substrate to HMPA that are discussed above. Base is then added to the intermediate reaction mixture, preferably in a proportion between about 3 and about 5 moles per mole HMPA contained in the initial charge, and conversion to the phosphonomethylated amine product of Formula III proceeds at a temperature typically in the range between about 70C and about 150° C., more typically in the range between about 90° C. and about 100° C.

In a particularly preferred embodiment, the "N-substituted" reactant according to Formula III preferably comprises iminodiacetic acid (IDA) or a salt thereof.

Where the amine substrate comprises a carboxylate salt of an N-substituted amino acid such as, e.g., Na glycinate or disodium iminodiacetic acid, a catalyst may advantageously be included in the reaction medium to promote the progress of the initial reaction step. Suitable catalysts may be compounds of transition metals such as, e.g., salts of ruthenium or osmium. The catalysts may either be homogeneous, e.g., salts of Ru or Os that are soluble in water or in an alkaline aqueous medium, or heterogeneous, such as oxides of Ru or Os. Heterogeneous catalysts may also be provided on an inert support such as silica or alumina. Where the reaction is catalyzed, it may be feasible to operate at a relatively low ratio of amine substrate to HMPA as discussed hereinabove.

Recovery Schemes for HMPA/Glycinate Reactions

Glyphosate or other product of Formula I may be separated from the reaction mixture by any of various process alternatives. Regardless of the ultimate method of recovery, it is generally desirable to produce a concentrated solution of the product of Formula I by evaporation of excess water and other solvent, or by other means such as, e.g., microfiltration. Any heterogeneous additives such as silica, aluminum oxide or rare earth hydroxides, should be removed by filtration or centrifugation.

According to one alternative, an insoluble glyphosate chelate can be formed and separated from the reaction mixture or concentrated reaction mixture in the manner described above with respect to recovery of the product of a halomethylphosphonic acid reaction.

As further described above with respect to the reaction of glycinate and halomethylphosphonic acid, another method of recovery comprises acidification of the reaction mixture or concentrate to the glyphosate isoelectric point, and precipitation of the free acid (free base) form of the product. The supernatant liquid can be recycled as a source of amine reactant for further preparation of glyphosate using HMPA or a halomethylphosphonic acid.

According to a still further alternative, the product of Formula I may be recovered by crystallization, also generally as described above with respect to the product of glycinate reaction with halomethylphosphonic acid.

Separation of glyphosate from unreacted glycinate may also be conducted by processes comprising ion exchange, generally along the lines of the processes described above with respect to FIGS. 1-4. In these cases, the reaction product is diluted with water to prevent salting out of dissolved reactants or products in process equipment, and yield a product which has a high concentration of water on a molar basis. Ion exchange separation schemes are substantially as shown in FIGS. 1-4, and the separation processes can be conducted substantially as described above. For example, resins capable of separating glyphosate from glycinate and chloride ions can be used in a comparable separation scheme for separating glyphosate from glycinate and bromide ions. If tripotassium (or other tri-alkali metal) hydroxymethylphosphonate elutes with tripotassium (or other trialkali metal) glyphosate in the ion exchange separation of glyphosate from glycinate and halide ions, it may be necessary to transfer the eluate to another column for separation of HMPA and glyphosate.

Alternatively, where the amine reactant comprises IDA, PMIDA may be recovered in the manner described above for PMIDA produced in the reaction of a halomethylphosphonic acid and glycinate. The PMIDA product may be converted to glyphosate by catalytic oxidation.

Reaction of HMPA with MEA or Derivative

In the preparation of HEAMPA or derivatives thereof, HMPA may be reacted with an alkanolamine, or an alkanolamine hydrohalide. Alkanolamine substrates for reaction with HMPA generally conform to Formula V as described above with reference to reactions of halomethylphosphonic acid.

Preferably, the ratio of equivalents monoethanolamine or other compound of Formula V to equivalents HMPA is at least about 1.5, more preferably at least about 3, still more preferably at least about 5, and most preferably at least about 8. A high ratio of Formula V compound to halomethylphosphonic acid promotes conversion of the alkanolamine substrate to HEAMPA or other compound of Formula IV, and minimal formation of by-product N,N-bis(phosphonomethyl)ethanolamine or other N,N-bis(phosphonomethyl) derivative.

As in the case of the conversion of glycinate to glyphosate, the HMPA reagent is preferably in the form of dehydrated self ester oligomers. Reaction is preferably conducted at elevated temperature, e.g., in a range between 125° and about 200° C., more typically in a range between about 150° and about 200° C. Water is a product of the reaction; but may optionally be removed from the reaction medium as the reaction proceeds. The reaction may be conducted in the melt (neat) or in the presence of any of the solvents discussed hereinabove for the reaction of HMPA with glycine and/or for the reaction of halomethylphosphonic acids with MEA. Because MEA and similar alkanolamines are liquid at room temperature, the use of a solvent is not generally necessary for the reactions of such alkanolamines and HMPA. In part because of the absence of solvent, it may be feasible to conduct the reactions of HMPA and MEA or other alkanolamine at relatively higher concentrations of reactants than in the case of the reaction of glycine or glycinate with HMPA. For example, it may be feasible to conduct the reaction at an initial HMPA concentration greater than about 5 wt. %, more typically greater than about 10 wt. %, preferably greater than about 15 wt. %.

Where the substrate comprises an MEA acid salt such as MEA:HCl, it is believed that the reaction may typically proceeds in two successive steps. According to such mechanism, MEA:HCl is first reacted with HMPA or an HMPA source to produce an intermediate reaction mixture; and the intermediate reaction mixture is then contacted with base to produce the desired phosphonomethylamine product of Formula IV. Without being held to any particular theory, it is believed that of MEA hydrochloride or other hydrohalide initially reacts with HMPA to form halomethylaminomethyl-phosphonic acid and the latter reacts with MEA free base to yield HEAMPA. Preferably, the base is an alkali metal hydroxide, most preferably NaOH or KOH, and is added in a ratio of at least about 1.5 moles base per mole hydroxymethylphosphonic acid initially present. More preferably, base is charged to the reaction medium in a ratio of at least about 2 moles per mole initial hydroxymethylphosphonic acid charge, more preferably in a ratio of at least about 3. Optionally, other bases can be present in addition to, or in lieu of an alkali metal hydroxide such as, for example, alkaline phosphate salts and hydroxides of countercations such as substituted ammonium, phosphonium, sulfonium or sulfoxonium, and mixtures thereof.

Where the substrate comprises MEA free base or other alkanolamine free base, the reaction of MEA and HMPA produces an intermediate adduct and or other intermediate species which has not been identified. Regardless of its structure, the intermediate reaction product may be hydrolyzed to the desired phosphonomethylated reaction product. Hydrolysis is conveniently effected by addition of an aqueous acid to the reaction mixture. Hydrohalide acids such as hydrobromic or hydrochloric are suitable for this purpose. The ratio of acid to amine equivalent in the reaction mixture is suitably comparable to the ratio used in the conversion of intermediate to desired product in the reactions of HMPA and glycinate. Hydrolysis is conveniently carried out at a temperature between about 60° and about 150° C., more typically between about 70° and 110° C., preferably between about 80° and 100° C.

Formation of the intermediate species from MEA free base and HMPA is understood to be a base-catalyzed reaction. Optionally, this step in the reaction may be conducted in the presence of a strong base. However, since MEA itself is alkaline, the formation of the intermediate may proceed without the addition of any base other than MEA.

Additives of the type described above with reference to the reactions of glycine and HMPA may also be useful in the first step of the reaction of either MEA amine salt or MEA free base and HMPA.

HMPA or dehydrated HMPA may also be reacted with a secondary alkanolamine such as diethanolamine or N-methyl monoethanolamine to produce N,N-bis(hydroxyethyl)aminomethylphosphonic acid or N-methyl-N-hydroxyethylaminomethylphosphonic acid. Because the use of a secondary amine substrate effectively inhibits or obstructs formation of by-product bis(phosphonomethyl) species, it may be possible to reduce the amine to HMPA ratio to a relatively low level and thereby minimize the extent to which unreacted amine must be recovered and recycled. Operation at relatively low amine to HMPA ratios may be facilitated by use of a Ru, Os, or other platinum metal or transition metal catalyst.

As discussed in connection with the reaction between glycinate and HMPA, the reaction of MEA and HMPA may also be conducted in a continuous mode.

Recovery of HEAMPA or Other Phosphonomethylated Alkanolamine

Where the reaction is conducted with an excess of monoethanolamine or other compound of Formula V relative to the charge of HMPA, recovery of the product further requires removal of the unreacted Formula V compound contained in the reaction mixture. Removal of unreacted Formula V compound from the hydrolysis reaction mixture may conveniently be accomplished by extraction with a water-immiscible solvent such as methylene dichloride. Solvents other than methylene dichloride which are effective for the extraction are discussed above with respect to extraction of MEA from a reaction mixture produced by the reaction of a halomethylphosphonic acid and MEA. As discussed above, the extract may be distilled to separate the compound of Formula V from the extraction solvent, with the former being recycled to the reaction step and the latter to the extraction step. Distillation may also produce an appropriate purge fraction for removal of impurities, or the impurities may be removed by purging or further processing of the recycle amine reactant or the recycle solvent, or both.

As further described above with respect to the reactions of halomethylphosphonic acids, MEA or other compound of Formula V may be distilled from the reaction mixture. The distillation process schemes there described may be used starting with the hydrolysis reaction mixture obtained after conversion of the HMPA/MEA intermediate adduct. Where an organic solvent is used for the reaction, by-product salt is preferably removed first, and the filtered reaction mixture is distilled for removal of both solvent and unreacted compound of Formula V.

Raffinate from the extraction may also processed as described above.

The recovery scheme of FIG. 5 may be used in recovering HEAMPA, substantially in the manner described above.

Dehydrogenation of HEAMPA or substituted HEAMPA to glyphosate or substituted glyphosate may also be carried out in the manner described above.

Reactions of HMPA with Amides

It has further been discovered that aminomethylphosphonic acid ("AMPA") can be prepared by reaction of HMPA with an amide. In accordance with this process, HMPA, or an HMPA self ester oligomer is reacted with an amide such as urea or formamide. Reaction between the amide and the methylol moiety of HMPA yields an intermediate adduct which comprises an N-acyl AMPA wherein the acyl group is derived from the amide. Thus, in the case of urea, the intermediate adduct comprises N-carbamyl AMPA, and in the case of formamide it comprises N-formyl AMPA. Hydrolysis with a base yields a salt of AMPA and a by-product salt of the carboxylic acid corresponding to the amide. Thus, where the amide is urea and the base is KOH, the by-product of the reaction is potassium carbamate. In the case of formamide and KOH, the by-product is potassium formate.

To carry out the process, HMPA, or preferably a self ester oligomer thereof, is contacted with an amide at a temperature typically in the range of 125° to 250° C., preferably between about 150° and about 200° C. The reaction can be conducted in the melt, or in the presence of any of the solvents discussed above with respect to the reactions of HMPA with glycine or MEA. Reactant ratios are also typically in the same ranges as those discussed above for glycine and MEA. After conversion of HMPA and the amide to the aforesaid adduct, base is added to the intermediate reaction mixture and the adduct hydrolyzed to yield the salt of AMPA and salt of the carboxylic acid from which the amide is derived.

AMPA recovered from the reaction mixture may be converted to glyphosate or HEAMPA by methods known to the art. For example, see WO 96/14135.

Any of a variety of amides may be selected for use in the reaction scheme of this embodiment of the invention. Formamide and urea are preferred. Generally, the amide may correspond to the formula $R^1C(O)NH_2$ wherein $R^1$ is selected from the group consisting of alkyl, substituted alkyl, aryl, substituted aryl, amino and substituted amino.

As in the case of halomethylphosphonic acid systems as described above, the media in which HMPA reacts with an amine or amide substrate are in some cases alkaline; and even where they are acidic, HMPA may not be fully protonated. Thus, it will be understood herein that wherever it is stated that the reaction is between "hydroxymethylphosphonic acid" and an amine or amide reactant, unless the context indicates otherwise, this is intended to encompass reaction between the amine or amide reactant and hydroxymethylphosphonate anion(s) as well, and wherever it is stated that the reaction is with a "salt of hydroxymethylphosphonic acid" this also encompasses reaction with hydroxymethylphosphonate anion(s).

The following examples illustrate the invention.

EXAMPLE 1

Preparation of Glyphosate from Chloromethylphosphonic Acid (CMPA) and Glycinate

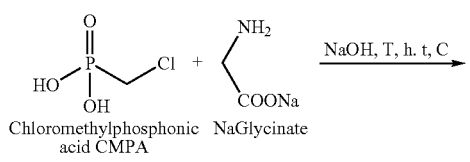
Chloromethylphosphonic acid CMPA    NaGlycinate

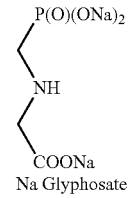
Na Glyphosate

Sodium glycinate (1.126 g) and chloromethylphosphonic acid ("CMPA") (0.132 g) were charged to an aqueous alkaline reaction medium (0.9 g NaOH in 0.7 ml water). Reaction was conducted at a temperature of 80° C. for 16 hours. Four additional reaction runs were conducted substantially in the same manner as the first run, but with some variation in conditions. In the third, fourth and fifth runs, the charge of sodium glycinate with respect to CMPA was double that of the first and second runs. In the second and fourth runs, no base other than sodium glycinate was charged. In the fifth run, calcium hydroxide was substituted for NaOH, the temperature was increased to 95° C. and the reaction time increased to 120 hours. Yields of glyphosate, glyphosine and HMPA were measured by HPLC and NMR. The respective glycine/CMPA ratios, base identity and ratio to CMPA, CMPA conversions, reaction temperatures, reaction times, glycine conversions, glyphosate yields, glyphosine yields and HMPA yields are set forth in Table 1.

TABLE 1

Influence of Glycine Amount on Reaction of CMPA with Sodium Glycinate.

| Molar Ratio CMPA:NaGly | Base | T, h | t, °C | CMPA Convers % | Glycine Convers % | Glyphosate Yield % | Glyphosine Yield % | HMPA Yield % | Analytical Method |
|---|---|---|---|---|---|---|---|---|---|
| 1:5 | 2 eq. NaOH | 16 | 80 | — 93.5 | 30.2 | 81.2 72.0 | 15.0 29 | 11.4 1.4 | HPLC NMR |
| 1:5 | none | 16 | 80 | — 84 | 18.1 | 77.6 65.6 | 15.8 65.6 | 10.4 0.9 | HPLC NMR |
| 1:10 | 2 eq. NaOH | 16 | 80 | — 100 | 36.6 | 86.9 85.4 | 9.6 12.6 | 13.1 2.0 | HPLC NMR |
| 1:10 | none | 16 | 80 | — 95.4 | 36.3 | 87.4 82.1 | 6.6 9.8 | 13.1 3.5 | HPLC NMR |
| 1:10 | Ca(OH)$_2$ | 120 | 95 | — 80.6 | — | 69.3 | 5.9 | 5.4 | HPLC NMR |

Additives such as La(OH)$_3$, or, preferably, polyethyleneimine, can be used to produce glyphosate in yields of 90 to 98% based on HMPA.

EXAMPLE 2

Further reactions runs were conducted in an aqueous alkaline reaction medium generally in the manner described in Example 1, but with variations in the water content of the reaction medium, reaction time and reaction temperature. Additives were included in certain of these runs, i.e., NaI at a concentration of 2.0% by weight in the second run and at a concentration of 0.5% by weight in the third run, tetrabutylammonium hydrogen sulfate in the fourth run at a concentration of 2.0% by weight, 15-crown-5 ether in the fifth run at a concentration of 6.0% by weight, lanthanum hydroxide in the sixth run at a concentration of 3.6% by weight and polyethyleneimine in the seventh and last run at a concentration of 1.9% by weight. Tetrabutylammonium hydroxide was substituted for NaOH as the base component in the fifth run.

The time and temperature conditions of each run, the identity of the base and molar ratio to CMPA, the ratio of water to CMPA, identity of additives, glycine conversion, glyphosate yield, glyphosine yield, phosphoric acid/phosphate yield, and analytical methods used in determining yields for the runs of this example are set forth in Table 2.

TABLE 2

Influence of Certain Additives on Reaction of CMPA with 10-Fold Excess of Sodium Glycinate.

| Additive Base Molar Ratio H$_2$O:CMPA | T, h | t, °C | CMPA Conversion % | Glycine Conversion % | Glyphosate Yield % | Glyphosine Yield % | HMPA Yield % | PO$_4$ Yield % | Analytical Method |
|---|---|---|---|---|---|---|---|---|---|
| none 2 eq. NaOH H$_2$O:CMPA 50:1 | 16 | 80 | — 100 | 36.6 | 86.9 85.4 | 9.6 12.6 | 13.1 2.0 | 0 0 | HPLC NMR |
| NaI 2 eq. NaOH H$_2$O:CMPA 39:1 | 16 | 90 | — 78 | — | 78 83 | 6.2 8.8 | 3.6 1.0 | 0 0 | HPLC NMR |
| NaI 2eq. NaOH H$_2$O:CMPA 65:1 | 18 | 90 | 100 | — | 88.0 91.1 | 4.4 4.3 | 5.4 4.3 | 2.5 0 | HPLC NMR |
| NBu$_4$HSO$_4$ 2eq. NaOH H$_2$O:CMPA 53:1 | 16 | 80 | — 100 | 28.2 | 85.7 87.1 | 8.6 11.0 | 2.7 1.9 | 1.1 0 | HPLC NMR |
| 15-crown-5 2eq. NBu$_4$OH, H$_2$O:CMPA 53:1 | 26 | 80 | — 100 | 18.1 | 83.1 88.0 | 6.9 11.0 | 2.8 1.9 | 1.0 0 | HPLC NMR |
| La(OH)$_3$ 1.5 eq. NaOH H$_2$O:CMPA 54:1 | 26 | 80 | — 100 | 25.2 | 93.6 87.4 | 7.4 11.6 | 2.6 1.0 | 1.2 0 | HPLC NMR |

TABLE 2-continued

Influence of Certain Additives on Reaction of CMPA with 10-Fold Excess of Sodium Glycinate.

| Additive Base Molar Ratio $H_2O$:CMPA | T, h | t, °C. | CMPA Conversion % | Glycine Conversion % | Glyphosate Yield % | Glyphosine Yield % | HMPA Yield % | $PO_4$ Yield % | Analytical Method |
|---|---|---|---|---|---|---|---|---|---|
| Polyetheyleneimine 2eq. NaOH $H_2O$:CMPA 54:1 | 26 | 80 | — 100 | 23.7 | 97.6 98.2 | 2.4 0 | 2.1 1.8 | 0.9 0 | HPLC NMR |

EXAMPLE 3

Reactions of Monoethanolamine with Chloromethylphosphonic Acid (CMPA)

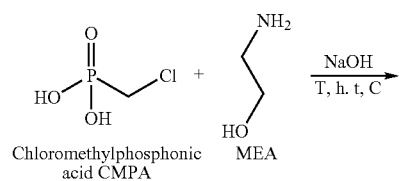

Chloromethylphosphonic acid CMPA    MEA

Chloromethylphosphonic acid (CMPA) can be reacted with MEA in an alkaline reaction system. MEA (10-fold excess) in the presence of NaOH reacts with CMPA in water or water-organic media at temperatures of 80 to 100° C. over 16 to 22 hours to produce HEAMPA in yields of 55 to 86% based on HMPA. The reaction rate depends on the amount of NaOH (see Table 3).

Monoethanolamine ("MEA") (0.9 g) and chloromethylphosphonic acid ("CMPA") (0.167 g), i.e., a ten fold molar excess of MEA, were charged to an aqueous alkaline reaction reaction medium (0.132 g NaOH in 0.6 ml water). Reaction was conducted at a temperature of 100° C. for 19 hours. Three additional reaction runs were conducted substantially in the same manner as the first run, but with some variation in conditions. The time and temperature conditions, molar ratio of NaOH to MEA, CMPA conversion, HEAMPA selectivity and yield, bis-adduct selectivity, selectivity to HMPA, and selectivity to phosphoric acid or phosphates is set forth in Table 3, together with the analytical methods used in determining the yields.

TABLE 3

CMPA Reactions with a 10-Fold Excess of MEA and Different Amounts of NaOH

| T, h t, °C. | NaOH Equivalents | CMPA Conversion % | HEAMPA Selectivity (Yield) % | Bis-adduct Selectivity % | HMPA Selectivity % | $PO_4$ Selectivity % | Analytical Method |
|---|---|---|---|---|---|---|---|
| 19 100° | 1.5 | — 94.5 | 83.2(78.6) 76.3(72.1) | — 21.3 | — 0 | — 2.6 | HPLC NMR |
| 16 80° | 2.6 | — 100 | 77.3 76.8 | — 20.3 | 5.6 2.9 | 1.8 0 | HPLC NMR |
| 48 80° | 3 | — 100 | 89.5 82.3 | — 13.7 | — 4.0 | — 0 | HPLC NMR |
| 21.5 95 | 3.5 | 100 | 81.7 | 12.7 | 5.6 | 0 | NMR |

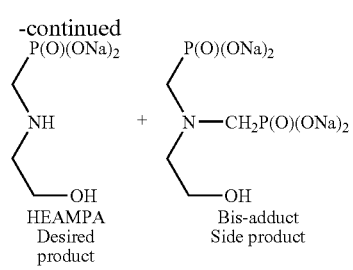

HEAMPA
Desired product

Bis-adduct
Side product

EXAMPLE 4

Reactions of MEA and CMPA were conducted generally in the manner described in Example 3 except that NaOH was replaced by $N(CH_3)_4OH$ and water content was varied. Substitution of $N(CH_3)_4OH$ led to increasing the product of hydrolysis of CMPA, i.e., HMPA. See Table 4.

TABLE 4

CMPA Reaction with a 10-Fold Excess of MEA and 3 Equivalents of $N(CH_3)_4OH$ at 92° C. for 22 Hours, Determined by $^{31}P$ NMR.

| $H_2O$ wt % | HEAMPA Yield % | Bis-adduct Yield % | HMPA Yield % | CMPA Conversion % |
|---|---|---|---|---|
| 2 | 49.2 | — | 30.5 | 98.8 |
| 50 | 55.7 | 3.7 | 38.4 | 97.9 |

EXAMPLE 5

The yield of the desired product, hydroxyethylamino-methylphosphonic acid (HEAMPA) strongly depends on the concentration of water in the reaction mixture. According to $^{31}$P NMR data, with the addition of 50 equivalents of water (42 wt %) the yield of HEAMPA increased to 84% from 55% for 4 $H_2O$ equivalents (19 wt %).

Further reaction runs were conducted in generally the same manner as Example 4, except that the water content was varied. Results of the runs of this Example are set forth in Table 5.

TABLE 5

Influence of Water Concentration on CMPA Reaction with a 10-Fold Excess of MEA and 3 Equivalents of NaOH at 90° C. for 21.5 Hours, Determined by $^{31}$P NMR.

| $H_2O$ wt % | Molar Ratio $H_2O$/CMPA | HEAMPA Yield % | Bis-adduct Yield % | HMPA Yield % | CMPA Conversion % |
|---|---|---|---|---|---|
| 19 | 12.25 | 71.3 | 21.5 | 3.5 | 100 |
| 28 | 23.12 | 77.4 | 18 | 3.6 | 100 |
| 36 | 34.08 | 82.3 | 11.7 | 4.9 | 100 |
| 42 | 46.00 | 84.6 | 9.8 | 5.6 | 100 |
| 47 | 56.08 | 84.2 | 5.7 | 7.6 | 97.5 |
| 51 | 66.34 | 80.5 | 5.3 | 8.4 | 94.4 |

EXAMPLE 6

Further reactions were carried out generally in the manner of Example 5, and in which the charge mixture contained either 42% by weight or 30% by weight water. Various organic solvents were also included in the reaction media. The conditions and results of the first set of reactions (at 42% by weight water) are set forth in Table 6, and the conditions and results of the second set of reactions (at 30% by weight water) are set forth in Table 7. As indicated by these results, some of the solvents like DMF, monomethylether of tetraethyleneglycol, acetonitrile, and 20 wt % tetraglyme (dimethylether of tetraethyleneglycol) were observed to increase the effect of over-alkylation, decreasing the yield of the desired product. A crown-ether, ethylene glycol, methanol, and 10 wt % tetraglyme are practically inactive, i.e., they do not affect the extent of over-alkylation. A favorable effect was obtained with 10 and 20 wt % glycerol, in the presence of which the yield of HEAMPA was improved up to 86% with minimal amounts of products of overalkylation, bis-adduct and hydrolysis, HMPA.

TABLE 6

Solvent Effect in CMPA Reaction with a 10-Fold Excess of MEA and 3 Equivalents of NaOH in Presence of 42 wt % $H_2O$ at 90° C. for 22 Hours, Determined by $^{31}$P NMR.

| Run | Solvent (wt %) | CMPA Conversion | HEAMPA Selectivity % | Bis-adduct Selectivity % | HMPA Selectivity % |
|---|---|---|---|---|---|
| 10 | none | 97.6 | 85 | 11.5 | 3.4 |
| 11 | DMF (10%) | 100 | 67.1 | 24.8 | 3.1 |
| 12 | DMF (20%) | 100 | 50.6 | 28.9 | 4.5 |
| 13 | 15-Crown-5 (10%) | 100 | 80.3 | 12.1 | 7.6 |
| 14 | Tetraglyme | 100 | 81.2 | 13.5 | 5.3 |
| 15 | EG (10%) | 100 | 81.6 | 7.8 | 5.2 |
| 16 | $CH_3OH$ (10%) | 98.4 | 83.1 | 10.3 | 6.5 |
| 17 | Glycerol (10%) | 94.4 | 87.8 | 8.5 | 3.7 |

TABLE 7

Solvent Effect (30 wt % H2O + 20 wt % Solvent) in CMPA Reaction with a 10-Fold Excess of MEA and 3 Equivalents of NaOH at 90° C. for 22 Hours ($^{31}$P NMR)

| Solvent (20 wt %) | CMPA Conversion % | HEAMPA Yield % | Bis-adduct Yield % | HMPA Yield % |
|---|---|---|---|---|
| Tetraethylene glycol mono Me-ester | 100 | 63.3 | 32.2 | 2.0 |
| $CH_3CN$ | 100 | 67.9 | 25.3 | 3.5 |
| Tetraglyme | 100 | 74.9 | 20.3 | 2.9 |
| Ethylene glycol | 100 | 80.6 | 14.1 | 2.1 |
| Glycerol | 100 | 86.2 | 11.7 | 2.0 |
| none | 100 | 82.0 | 16.5 | 2.2 |

EXAMPLE 7

TABLE 8

Reactions of CMPA and IDA in Equimolar Amounts

| Catalyst, eq. NaOH, eq. $H_2O$ | Time, hours | T, ° C. | CMPA Conv. % | GI % | Glyphosate | HMPA % | MPA % | $PO_4$ % | Method |
|---|---|---|---|---|---|---|---|---|---|
| none 4.8 NaOH 25 $H_2O$ | 15.3 | 95 | 79 | 70 | 0 | 9 | 0 | 0 | NMR |
| none 4 NaOH | 20 | 95 | 64 | 54.2 | 0 | 9.4 | 0 | 0 | NMR |
| CuCl 4 NaOH 33 $H_2O$ | 6 | 95 | 95.789.0 | 0 | 0 | 6.7 | 0 | NNR | |
| $CuCl_2$ 4 NaOH 25 $H_2O$ | 3 | 95 | 52 | 52 | 0 | 0 | 0 | 0 | NMR |

TABLE 8-continued

Reactions of CMPA and IDA in Equimolar Amounts

| Catalyst, eq. NaOH, eq. H$_2$O | Time, hours | T, °C. | CMPA Conv. % | GI % | Glyphosate | HMPA % | MPA % | PO$_4$ % | Method |
|---|---|---|---|---|---|---|---|---|---|
| CuCl$_2$ 4 NaOH 25 H$_2$O | 20 | 95 | 91 | 90.2. | 0 | 0 | 0 | 0 | NMR |
| Cu (ClO$_4$)$_2$ 4 NaOH 33 H$_2$O | 6 | 95 | 70.6 | 70.6 | 0 | 0 | 0 | 0 | NMR |
| Cu(ac)$_2$/pvp 4 NaOH 33 H$_2$O | 6 | 95 | 43.6 | 43.6 | 0 | 0 | 0 | 0 | NMR |
| CU(OH)$_2$ 4 NaOH 33 H$_2$O | 6 | 95 | 100 | 90.1 | 4.6 | 0 | 4.5 | 0 | NMR |
| CuO/SiO$_2$ 4 NaOH 25 H$_2$O | 1.5 | 95 | 61 | 61 | 0 | 0 | 0 | 0 | NNR |
| CuO/SiO$_2$ 4 NaOH 25 H$_2$O | 3 | 95 | 81 | 81 | 0 | 0 | 0 | 0 | NMR |
| CuO/SiO$_2$ 4 NaOH 25 H$_2$O | 20 | 95 | 100 | 99.1 | 0 | 0 | 0.9 | 0 | NMR |
| CuO/Al$_2$O$_3$ 4.5 NaOH 55 H$_2$O | 5 | 100 | 52 | 46 56.4 | 0 4.3 | 1.5 1.6 | 0 | 0 0 | NMR HPLC |
| CuO/Al$_2$O$_2$ 4.5 NaOH 68 H$_2$O | 6 | 95 | 60 | 60 | 0 | 0 | 0 | 0 | NM |
| CuO/MnO$_2$ 4.5 NaOH 68 H$_2$O | 6 | 95 | 35 | 35 | 0 | 0 | 0 | 0 | NMR |
| CuO 4.5 NaOH 68 H$_2$O | 6 | 95 | 50 | 45 | 0 | 5 | 0 | 0 | NMR |
| CUO/C$_{R2}$O$_3$ 4.5 NaOH 68 H$_2$O | 6 | 9 | 44 | 44 | 0 | 0 | 0 | 0 | NMR |
| Raney Cu 4.5 NaOH 25 H$_2$O | 1.5 | 95 | 96.6 | 90.4 | 0 | 0 | 6.2 | 0 | NMR |
| Raney Cu 2 NaOH 25 H$_2$O | 1.2 | 95 | 15 | 0 | 0 | 0 | 15.3 | 0 | NMR |
| Raney Cu 2 NaOH 25 H$_2$O | 17 | 95 | 20 | 3 | 2.7 | 0 | 15.3 | 0 | NMR |
| Raney Cu 2 NaOH 25 H$_2$O | 65 | 95 | 30 | 6 | 4 | 0 | 19.5 | 0 | NMR |
| Cu-powder 4 NaOH 33 H$_2$O | 6 | 95 | 100 | 92.3 | 0 | 0 | 7.7 | 0 | NMR |
| Cu-slurry 4 NaOH 33 H$_2$O | 6 | 95 | 100 | 84.9 | 0 | 0 | 15.1 | 0 | NMR |
| Cu-Pd/C 4.5 NaOH 55 H$_2$O | 6 | 100 | 100 | 98.3 | 0 | 0 | 1.7 | 0 | NMR |
| Cu-Pd/C 4 NaOH 25 H$_2$O | 3.2 | 95 | 98.4 | 96.2 | 0 | 0 | 2.2 | 0 | NMR |

TABLE 8-continued

Reactions of CMPA and IDA in Equimolar Amounts

| Catalyst, eq. NaOH, eq. $H_2O$ | Time, hours | T, °C. | CMPA Conv. % | GI % | Glypho-sate | HMPA % | MPA % | $PO_4$ % | Method |
|---|---|---|---|---|---|---|---|---|---|
| Cu-Pd/C 4 NaOH 9 $H_2O$ | 2.5 | 95 | 85 | 84 | 0 | 0 | 1 | 0 | NNR |

Preparation of N-phosphonomehtyliminodiacetic Acid (GI) from Chloromethylphosphonic Acid (CMPA) and Iminodiacetic Acid (IDA)

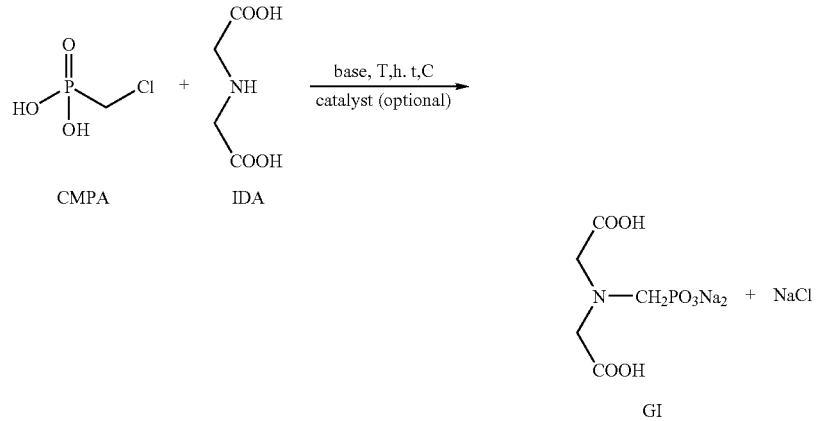

EXAMPLE 8

Preparation of Self-esters of HMPA by Heating under Vacuum

Into a 15 ml flask fitted with a magnetic stirrer was transferred 0.5510 g (3.7 mmol) of crystalline HMPA containing 1.4 molecules of $H_2O$ [$(OH)_2P(O)CH_2OH\cdot1.4H_2O$ ]. The flask was immersed in an oil bath and heated to 100° C. for one hour and twenty minutes under vacuum of about 1 mm/Hg. A light yellow, viscous syrup-like liquid was formed. According to $^1H$, $^{13}C$, and $^{31}P$ NMR, it is composed of self-ester dimer (1)(20%) and its polymeric or oligomeric (with P—O—CH$_2$—P and P—O—P groups) derivatives.

EXAMPLE 9

Preparation of Self-esters of HMPA by Azeotropic Distillation with Xylene

Into a 50 ml flask fitted with a magnetic stirrer and Dean-Stark trap with a condenser and thermometer was transferred 0.982 g (6.6 mmol) of crystalline HMPA contained 1.4 molecules of $H_2O$, [$(OH)_2P(O)CH_2OH\cdot1.4H_2O$ ] and 15 ml of xylene (isomeric mixture, b.p. 137-144° C.). The flask was immersed in an oil bath and heated to 165° C. for 19 hours. About 0.7 ml of water was collected in the trap. A light yellow, dense syrup was formed. According to $^1H$, $^{13}C$, and $^{31}P$ NMR, it is composed of polymeric or oligomeric (with P—O—CH$_2$—P and P—O—P groups) derivatives of self-ester dimer (1), and contains 10% self-ester dimer (1).

EXAMPLE 10

Preparation of Self-esters of HMPA by Azeotropic Distillation with Mesitylene Into a 50 ml flask fitted with a magnetic stirrer and Dean-Stark trap with condenser and thermometer was transferred to 0.982 g (6.6 mmol) of crystalline HMPA containing 1.4 molecules of $H_2O$, [$(OH)_2P(O)CH_2OH\cdot1.4H_2O$ ] and 15 ml of mesitylene (1,3,5-trimethylbenzene, b. p. 164° C.). The flask was immersed in an oil bath and heated to 188° C. for 20 hours. A yellow, solid material like amber was formed. According to $^1H$, $^{13}C$, and $^{31}P$ NMR, it is composed of polymeric or oligomeric (with P—O—CH$_2$—P and P—O—P groups) derivatives of self-ester dimer (1), and contains only trace amount of (1). Obtained by this way "dehydrated HMPA" can be transformed into self-ester dimer under mild hydrolytic conditions.

EXAMPLE 11

Reaction of HMPA Self-esters with Monobenzylamine

A sample of HMPA self-ester, prepared as described above in the example 8 from 1.489 g (10.06 mmol) of $(OH)_2P(O)CH_2OH\cdot1.4H_2O$. After removing mesitylene 10 ml of N-benzylamine was added to HMPA self-esters. The flask was immersed in an oil bath and heated up to 180° C. for 16 hours. Then the reaction mixture was cooled and diluted by 10 ml of $D_2O$ and 5 ml of concentrated HCl. This solution was heated at 95° C. for four hours to give, according $^{31}P$ NMR, 77.8% desired product, N-benzylaminomethylphosphonic acid, 9.1% N,N-dibenzylaminomethylphosphonic acid, 3.3% $H_3PO_4$, and 9.8% sym-HMPA ether $\{[(OH)_2P(O)CH_2]_2O\}$.

EXAMPLE 12

Preparation of Aminomethylphonic Acid (AMPA) from HMPA Self-esters and Monobenzylamine To a sample of HMPA self-esters, prepared as described above in the example 8 from 0.551 g (3.7 mmol) of $(OH)_2P(O)CH_2OH \cdot 1.4H_2O$, 5.5 ml of N-benzylamine was added. The flask was immersed in an oil bath and heated to 180° C. for 16 hours with stirring. In the morning white crystals were present in the liquid. To the reaction, mixture 30 ml of 6% NaOH was added and a homogeneous solution was formed. Excess monobenzylamine was extracted by toluene (4×20 ml) and then ether (2×20 ml). The aqueous layer was diluted by water to 100 g, and 10 g of the solution was hydrogenolyzed under 90 psi $H_2$ pressure in the presence of $Pd(OH)_2/C$ to give, according to HPLC, AMPA in 90.6% yield.

EXAMPLE 13

Preparation of Aminomethylphosphonic Acid (AMPA) from HMPA Self-esters and Urea

To a sample of HMPA self-esters, prepared as described above in example 8 from 0.2975 g (2.13 mmol) of $(OH)_2P(O)CH_2OH \cdot 1.4H_2O$ at 120° C. for 2 hours, urea (1.245 g, 20.75 mmol) was added. The flask was immersed in an oil bath and heated to 185° C. for 15 hours with stirring under $N_2$. To the reaction mixture 10 ml of 15% NaOH was added and the homogeneous solution was hydrolyzed for 10 hours under reflux. According to HPLC, AMPA was obtained in 93% yield with 3.6% $H_3PO_4$, O0.9% $H_3PO_3$, and 4.1% bis-phosphonomethylimine also detected.

EXAMPLE 14

Preparation of N-phosphonomethylglycine(glyphosate) from HMPA Self-esters and Sodium Glycinate in Melt A sample of HMPA self-esters, prepared as described above in example 8 from 0.066 g (0.48 mmol) of $(OH)_2P(O)CH_2OH \cdot 1.4H_2O$, was stirred with an excess of sodium glycinate (0.482 g, 4.97 mmol) in 2 ml of acetonitrile for about ten minutes, followed by removal of the solvent. The flask was immersed in an oil bath and heated to 180° C. for 16 hours with vigorous stirring. At the end of this time the reaction mixture was hydrolyzed by 24% HBr (10 ml) at 110° C. for 6 hours to give, according to HPLC, 16.7% glyphosate, 1.1% AMPA, 2.3% $H_3PO_4$, and 1.5% $H_3PO_3$ at 20% HMPA conversion.

EXAMPLE 15

Preparation of N-phosphonomethylglycine(glyphosate) from HMPA Self-esters and Sodium Glycinate in 15-crown-5 ether A sample of HMPA self-esters, prepared as described above in example 8 from 0.077 g (0.56 mmol) of $(OH)_2P(O)CH_2OH \cdot 1.4H_2O$ was vigorously stirred with an excess of sodium glycinate (0.488 g, 5.03 mmol) in 2 ml of 15-crown-5 ether at 178° C. for 16 hours. At the end of this time the reaction mixture was hydrolyzed by 24% HBr (10 ml) at 110° C. for 6 hours to give, according to HPLC, 18.0% glyphosate, 1.8% AMPA, 1.9% $H_3PO_4$, and 1.9% glyphosine at 23% HMPA conversion.

EXAMPLE 16

Preparation of N-phosphonomethylglycine(glyphosate) from HMPA Self-esters and Sodium Glycinate in Sulfolane A sample of HMPA self-esters, prepared as described above in example 8 from 0.106 g (0.775 mmol) of $(OH)_2P(O)CH_2OH \cdot 1.4H_2O$ was vigorously stirred with an excess of sodium glycinate (0.480 g, 4.96 mmol) in 1.5 ml of sulfolane at 180° C. for 16 hours. At the end of this time the reaction mixture was hydrolyzed by 24% HBr (10 ml) at 110° C. for 6 hours to give, according to HPLC, 15.1 % glyphosate, 1.2% AMPA, 2.2% $H_3PO_4$, 0.7% $H_3PO_3$, and 1.7% glyphosine at 20% HMPA conversion.

EXAMPLE 17

Preparation of N-phosphonomethylglycine(glyphosate) from HMPA Self-esters and Sodium Glycinate in Sulfolane A sample of HMPA self-esters, prepared as described above in example 8 from 0.064 g (0.47 mmol) of $(OH)_2P(O)CH_2OH \cdot 1.4H_2O$ was vigorously stirred with excess of sodium glycinate (0.475 g, 4.90 mmol) in 2 ml of sulfolane in the presence of 0.219 g (1.46 mmol) of NaI at 150° C. for 94 hours. At the end of this time the reaction mixture was hydrolyzed by 24% HBr (10 ml) at 110° C. for 6 hours to give, according to HPLC, 30.3% glyphosate, 2.5% AMPA, 4.7% $H_3PO_4$, and 0.7% glyphosine at 36% HMPA conversion.

EXAMPLE 18

Preparation of N-(hydroxyethyl)aminomethylphosphonic Acid (HEAMPA) from HMPA Self-esters and Monoethanolamine To a sample of HMPA self-esters, prepared as described above in example 8 from 0.140 g (1.02 mmol) of $(OH)_2P(O)CH_2OH \cdot 1.4H_2O$ at 110° C. for 2 hours and placed in the Fisher bottle, 0.620 g (10.15 mmol) of monoethanolamine was added. The bottle was immersed into an oil bath and heated to 185° C. for 17 hours with stirring. Then the excess MEA was extracted by methylene chloride, and the residue was hydrolyzed by 10 ml of 25% HCl at 90° C. for 16 hours to give, according to $^{31}P$ NMR, 18.4% HEAMPA, 2.6% N,N-bis-phosphomethylethanolamine, and 1.9% $H_3PO_4$ at 23% HMPA conversion.

EXAMPLE 19

Preparation of N-(hydroxyethyl)aminomethylphosphonic Acid (HEAMPA) from HMPA Self-esters and Monoethanolamine To a sample of HMPA self-esters, prepared as described above in example 8 from 0.177 g (1.29 mmol) of $(OH)_2P(O)$ CH$_2$OH·1.4H$_2$O at 105° C. for 2 hours, 1.01 g (16.5 mmol) of monoethanolamine and 0.05 g (0.3 mmol) of NaI were added. The flask, fitted with a condenser, was immersed in an oil bath and heated to 163° C. for 68 hours with stirring. Then the excess MEA was extracted by methylene chloride, and the residue was hydrolyzed by 10 ml of 24% HBr at 110° C. for 6 hours to give, according to HPLC, 13.4% HEAMPA at 14% HMPA conversion.

EXAMPLE 20

Preparation of
N-(hydroxyethyl)aminomethylphosphonic Acid
(HEAMPA) from HMPA Self-esters and
Monoethanolamine in Anisole To a sample of HMPA self-esters, prepared as described above in example 8 from 0.343 g (2.5 mmol) of (OH)$_2$P(O)CH$_2$OH·1.4H$_2$O at 110° C. for 2 hours, 1.205 g (19.7 mmol) of monoethanolamine and 2 ml of anisole were added. The flask, fitted with condenser, was immersed in an oil bath and heated to 180° C. for 16 hours with stirring. Then the anisole and excess MEA were extracted by methylene chloride, and the residue was hydrolyzed by 10 ml of 25% HCl at 90° C. for 16 hours to give, according to $^{31}$P NMR, 15.9% HEAMPA, at 16% HMPA conversion.

EXAMPLE 21

Preparation of
N-(hydroxyethyl)aminomethylphosphonic Acid
(HEAMPA) from HMPA Self-esters and
Monoethanolamine in Benzylcyanide To a sample of HMPA self-esters, prepared as described above in example 8 from 0.143 g (1.04 mmol) of (OH)$_2$P(O)CH$_2$OH·1.4H$_2$O at 110° C. for 3 hours, 0.620 g (10.2 mmol) of monoethanolamine and 2 ml of benzylcyanide were added. The flask, fitted with a condenser, was immersed in an oil bath and heated to 185° C. for 17 hours with stirring. Then the benzylcyanide and excess MEA were extracted by methylene chloride, and the residue was hydrolyzed by 10 ml of 25% HCl at 90° C. for 16 hours to give, according to $^{31}$P NMR, 14.6% HEAMPA, at 15% HMPA conversion.

EXAMPLE 22

The preparation of Example 13 was substantially repeated, but with an increased ratio of urea to HMPA. The conditions of the reaction, HMPA conversion, AMPA selectivity, iminobis (i.e., glyphosine) selectivity and phosphate selectivity are set forth below in Table 9 wherein T,h=reaction time in hours, and t, C=reaction temperature in degrees centigrade.

TABLE 9

Free HMPA Reactions with Excess Urea

| T, h | t, C. | HMPA Conversion % | AMPA Selectivity % | Iminobis Selectivity % | PO$_4$ Selectivity % |
|---|---|---|---|---|---|
| 15 | 185 | 100 | 98 | 0.2 | 4.1 |

EXAMPLE 23

In a series of runs, glyphosate salt was prepared by reaction of dehydrated HMPA and a ten fold excess of each of several glycine acid salts. Three runs were conducted with glycine hydrochloride, one with trifluoroacetic acid salt, and another with the sulfuric acid salt. The conditions of the reactions, HMPA conversions, glycine conversions, and selectivities are shown in Table 10.

TABLE 10

Dehydrated HMPA Reactions with 10-Fold Excess of Some Acid Salts of Glycine

| Glysine Salt | T, h t, C. | HMPA Conversion % | Glycine Conversion % | Glyphosate Selectivity (Yield) % | Glyphosine Selectivity % | Method |
|---|---|---|---|---|---|---|
| HCl | 16 180 | 70.5 | 63 | 59.6 (42) | 1.4 | HPLC |
| HCl | 16 171 | 53 | 45 | 92.4 (49) | 1.9 | HPLC |
| HCl | 17 166 | 54 64.6 | 29.5 | 101.9 (55) 87.2(56.3) | 6.1 6.5 | HPLC NMR |
| CF$_3$COOH | 19 162 | 0 | — | 0 | 0 | NMR |
| H$_2$SO$_4$ | 19 162 | 0 | — | 0 | 0 | NMR |

EXAMPLE 24

Additional reactions of glycine hydrochloride and HMPA were conducted under various conditions and, in certain instances, in the presence of various additives. The additives used, reaction conditions and results are shown in Table 11.

TABLE 11

Excess Glycine Hydrochloride

| Conditions | T, h | t, C. | HMPA Conversion % | Glyphosate Selectivity (Yield) % | Glyphosine Selectivity % | Method |
|---|---|---|---|---|---|---|
| house vacuum | 17 | 162 | 44 | 95.4 (42) | 4.5 | NMR |
| HMPA closed vessel | 17 | 154 | 34.6 34.7 | 97.7 (33.8) 100 (34.7) | 0 0 | HPLC NMR |
| molecular sieves | 17 | 162 | 48.8 | 89.1 (43.5) | 7.4 | NMR |
| under reflux | 16 | 152 | 25 | 94.6 (23.2) | 0 | NMR |

EXAMPLE 25

Free, i.e., monomeric HMPA was reacted with MEA hydrochloride in the presence of a molecular sieve additive. Conditions of the reaction, conversions and selectivities are shown in Table 12.

TABLE 12

Dehydrated HMPA Reactions with Excess MEA Hydrochloride

| MEA HCl Equival. | T, h t, C. | Additive | MEA Conversion % | HMPA Conversion % | HEAMPA Selectivity (Yield) % | Bis-adduct Selectivity % | Method |
|---|---|---|---|---|---|---|---|
| 10 | 51 160 | none | 61.3 | 67.4 70 | 42.4(28.6) 41.4 (29) | — — | HPLC NMR |
| 5.5 | 24 153 | molec. sieves | — | 58.2 | 67.4(39.2) | 14.1 | NMR |

EXAMPLE 26

HMPA was reacted with a ten fold excess of MEA:HCl in the presence of molecular sieves. Conditions of the reaction, HMPA conversion and selectivities are shown in Table 13.

TABLE 13

Free HMPA Reactions with 10-Fold Excess of MEA Hydrochloride

| t, C. | T, h | Additive | HMPA Conversion % | HEAMPA Selectivity (Yield) % | Bis-adduct Selectivity % | Method |
|---|---|---|---|---|---|---|
| 154 | 17 | molecular sieves | — 31.6 | 82 (25.9) 61.7 (19.5) | — 0 | HPLC NMR |

EXAMPLE 27

In a series of runs, HMPA was reacted with each of several amine substrates in the presence of a variety of catalysts. The substrates, catalysts, reaction conditions and product yields are set forth in Table 14. In this table, "DSIDA" is disodium iminodiacetate, "DSHMPA" is the disodium salt of HMPA, "TBA$_2$HMBA" is the di-t-butyl ester of HMPA and "TBA$_2$IDA" is the di-t-butyl ester of IDA.

TABLE 14

Reactions of HMPA with functionalized amines

| No. | Acid Base | A B | Catalyst, Ligand Additives (equiv. wrt Acid SM) | T °C. t, hr | % Product | Comments |
|---|---|---|---|---|---|---|
| 1 | HMPA NaGly | 1.1 | RuCl$_3$ 2 NaOH/0.4 mL H$_2$O | 200 16 | 0% Glyphosate | |
| 2 | HMPA NaGly | 1.1 | OsCl$_3$ 2 NaOH/0.25 mL H$_2$O | 200 16 | 0% Glyphosate | |
| 3 | HMPA DSIDA | 1.4 | RuCl$_3$ 2 NaOH/0.47 mL H$_2$O | 200 16 | 3.9% GI | 2 HPLC methods confirm |
| 4 | HMPA DSIDA | 0.77 | OsCl$_3$ 2 NaOH/0.25 mL H$_2$O | 200 16 | 0.4% GI | |
| 5 | TBA$_2$HMPA TBA$_2$IDA | 1.25 | RuCl$_3$ neat | 200 16 | 0% GI | |
| 6 | HMPA IDA | 2 | RuCl$_3$ 4 NaOH | 242 4.5 | 0.3% GI | |
| 7 | TBA$_2$HMPA TBA$_2$IDA | 3 | RuCl$_3$ | 180 20 | 0.2% GI | |
| 8 | HMPA IDA | 3.5 | RuCl$_3$, Tripod 9 NaOH/H$_2$O | 180 20 | 1% GI | |
| 9 | DSHMPA DSIDA | 5 | RuCl$_3$ 0.6 mL H$_2$O | 200 0.5 | 0.3% GI | |

TABLE 14-continued

Reactions of HMPA with functionalized amines

| No. | Acid Base | A B | Catalyst, Ligand Additives (equiv. wrt Acid SM) | T °C. t, hr | % Product | Comments |
|---|---|---|---|---|---|---|
| 10 | DSHMPA DSIDA | 5 | $RuCl_3$ 1 mL $H_2O$ | 200 1.5 | 0.9% GI | |
| 11 | DSHMPA DSIDA | 5 | $RuCl_3$ 1 mL $H_2O$ | 200 16 | 10.6% GI 3.5% Glyphosate 3% Glyphosine | 2.3% N-Me Glypho 1.6% Iminobis 1% AMPA Confirmed by 2 HPLC methods |
| 12 | HMPA DSIDA | 1.5 | $RuCl_3$ 2 NaOH/$H_2O$ | 200 3 | 0.9% GI | |
| 13 | HMPA DSIDA | 2 | $RuCl_3$, Tripod 2 $Na_2CO_3$, 1 mL $H_2O$, 3 mL DMAC | 200 18 | 2.8% GI | |
| 14 | HMPA DSIDA | 4.5 | $RuCl_3$ 4.5 $Na_2CO_3$, 1 NaOH, 1 mL $D_2O$ | 200 16 | 9.8% GI | Confirmed by 2 HPLC methods |

EXAMPLE 28

In a series of runs, HMPA was separately reacted with benzylamine, urea and formamide, in each case in the presence of a catalyst. The substrate, catalyst, conditions of the reaction and results are set forth in Table 15.

TABLE 15

Reactions of HMPA with amines and amides

| No. | Acid Base | A B | Catalyst, Ligand Additives (equiv. wrt Acid SM) | T °C. t, hr | % Product | Comments |
|---|---|---|---|---|---|---|
| 1 | HMPA $BzNH_2$ | 0.33 | $RuCl_3$ | 165 3 | 0% AMPA | After hydrolysis & hydrogenolysis |
| 2 | HMPA $Bz_2NH$ | 0.33 | $RuCl_3$ | 165 3 | 0% AMPA | After hydrolysis % hydrogenolysis |
| 3 | HMPA $Bz_2NH$ | 1.4 | $OsCl_3$, tripod DMAC | 150 3 | 0% AMPA | After hydrolysis & hydrogenolysis |
| 4 | $TBA_2$HMPA $Bz_2NH$ | 1.1 | $RuCl_2(PPh_3)_3$, tripod, DMAC | 150 3 | 0.3% AMPA | After hydrolysis & hydrogenolysis |
| 5 | HMPA $HCONH_2$ | 0.01 | $RuCl_2(PPh_3)_3$ | 180 1 | 4.9 or 0% AMPA | After hydrolysis |
| 6 | HMPA $CH_3CONH_2$ | 0.01 | $RuCl_2(PPh_3)_3$ | 180 16 | 5.0 or 0.7% AMPA | After hydrolysis |

EXAMPLE 29

In each of a series of runs, disodium HMPA was reacted with DSIDA in the presence of a homogeneous ruthenium catalyst. The identity of the catalyst, conditions of the reaction and results are set forth in Table 16.

TABLE 16

Homogeneous ruthenium catalysts in the reaction of DSHMPA with DSIDA

| No. | Catalyst | Additive | Ratio acid:base | T, h t, C. | HMPA Conv % | DSIDA Conv % | GI % | Glyphosate % | Total GI + Glyph % |
|---|---|---|---|---|---|---|---|---|---|
| 1 | RuCl$_3$ | 1 ml H$_2$O | 1:5 | 16 200 | 64 | 59 | 2.6 | 1.3 | 3.9 |
| 2 | RuCl$_3$ | 1 ml H$_2$O | 5:1 | 16 200 | 16 | 96 | 10.6 | 3.5 | 14.1 |
| 3 | RuCl$_3$ | 1 ml H$_2$O 2 ml DMA | 3.5:1 | 20 200 | — | — | 1 | 0 | 1 |
| 4 | RuCl$_3$ | 1 ml H$_2$O 5 ml TDA-1; tripod | 5:1 | 18 200 | — | — | 0 | 0 | 0 |
| 5 | RuCl$_3$ | 1 ml H$_2$O 5 eq HCOOH pd-black | 5:1 | 15 200 | — | — | 0.8 | 0 | 0.8 |
| 6 | RuCl$_3$ | 1 ml H$_2$O 5 eq HCOONa pd-black | 5:1 | 17 200 | 2 | 100 | 3.6 | 0 | 3.6 |
| 7 | RuCl$_3$ | 1 ml H$_2$O 4 eq NaBH$_4$ | 5.5:1 | 18 200 | 29 | 70 | 8.7 | 4.9 | 13.6 |
| 8 | RuCl$_3$ | 1 ml H$_2$O 1 eq HCOONH$_4$ | 5.5:1 | 18 200 | 11 | 71 | 13.4 | 6.4 | 19.8 |
| 9 | RuCl$_3$ | 1 ml H$_2$O 5 eq HCOONH$_4$ | 4.5:1 | 16 200 | 18 | 72 | 22.3 | 5.1 | 27.4 |
| 10 | H(AcO)Ru-(PPh$_3$)$_3$ | 1 ml H$_2$O | 4:1 | 18 200 | — | — | 0 | 0 | 0 |
| 11 | (C$_5$Me$_5$RuCl$_2$)$_n$ | 1 ml H$_2$O | 4:1 | 15 200 | — | — | 3.3 | 0 | 3.3 |
| 12 | Ru(NH$_3$)$_6$Cl$_2$ | 1 ml H$_2$O | 4.5:1 | 19 200 | 6 | 64 | 7.2 | 1.9 | 9.1 |
| 13 | Ru$_3$(CO)$_{12}$ | 1 ml H$_2$O | 5:1 | 15 200 | 13 | 74 | 10.3 | 4.4 | 14.7 |

EXAMPLE 30

In each of a series of runs, disodium HMPA was reacted with DSIDA in the presence of a heterogeneous ruthenium catalyst. The identity of the catalyst, conditions of the reaction and results are set forth in Table 17.

TABLE 17

Heterogeneous ruthenium catalysts in the reaction of DSHMPA + DSIDA (in 1 ml H$_2$O)

| No. | Catalyst | Ratio acid:base | T, h t, C. | HMPA Conv % | DSIDA Conv % | GI % | Glyphosate % | Total GI + Glyph % |
|---|---|---|---|---|---|---|---|---|
| 14 | 5% Ru on C Strem lot 140841-s1 44-4050 | 3.5:1 | 18 200 | 23 | 65 | 8.2 | 4.0 | 12.2 |
| 15 | 5% Ru on Alumina Alfa | 4.5:1 | 19 200 | 7 | 96 | 10.0 | 2.8 | 12.8 |

TABLE 17-continued

Heterogeneous ruthenium catalysts in the reaction of DSHMPA + DSIDA (in 1 ml H$_2$O)

| No. | Catalyst | Ratio acid:base | T, h t, C. | HMPA Conv % | DSIDA Conv % | GI % | Glyphosate % | Total GI + Glyph % |
|---|---|---|---|---|---|---|---|---|
| 16 | lot K12C15 stk 11749 5% Ru on activated C Strem lot 132308-s 44-4040 | 4.5:1 | 19 200 | 28 | 64 | 17.4 | 10.3 | 27.7 |

EXAMPLE 31

A series of runs was conducted to determine the effects of dilution and hydrogen pressure in the reactions of HMPA and DSIDA as catalyzed with a 5 wt. % Ru/C catalyst. Conditions of the reaction, identity of additives and results are set forth in Table 18.

TABLE 18

Effects of dilution, H$_2$, and pH using 5% Ru on activated carbon, Strem (lot 132308-s 44-4040)

| No. | Additive | Ratio acid:base | T, h t, C. | HMPA Conv % | DSIDA Conv % | GI % | Glyphosate % | total GI + Glyph % |
|---|---|---|---|---|---|---|---|---|
| 17 | 3 ml H$_2$O | 4.8:1 | 18 200 | 8 | 70 | 8.8 | 8.4 | 17.2 |
| 18 | 5 eq HCCOONH$_4$ | 5:1 | 18 200 | — | — | 0 | 0 | 0 |
| 19 | H$_2$ 100 psi | 4.6:1 | 20.5 200 | 35 | 75 | 23.5 | 6.8 | 30.3 |
| 20 | NaOH 0.25 mmol, H$_2$ 100 psi | 4.6:1 | 17 200 | 31 | 64 | 11.8 | 4.2 | 16.0 |
| 21 | HMPA 0.5 mmol, H$_2$ 100 psi | 4.5:1 | 18 200 | 8 | 70 | 1.2 | 4.3 | 5.5 |
| 22 | HMPA 0.08 mmol, H$_2$ 100 psi | 4.6:1 | 17 200 | 31 | 81 | 29.0 | 8.9 | 37.9 |

EXAMPLE 32

Two runs were conducted in which DSHMPA was reacted with sarcosine in the presence of a 5% Ru/C catalyst. Conditions and results of these runs are set forth in Table 19.

TABLE 19

Reactions of DSHMPA with sarcosine

| No. | Amino Acid | Catalyst | Ratio acid:base | T, h t, C. | Glyphosate % | NMG % | Total Glyph + NMG % |
|---|---|---|---|---|---|---|---|
| 24 | Sarcosine | 5% Ru on activated C Strem lot 132308-s 44-4040 | 4.1:1 | 16 200 | 8.4 | 2.9 | 11.3 |
| 25 | Sarcosine | 5% Ru on activated C Strem lot 132308-s 44-4040 | 4.6:1 | 16 200 | 9.7 | 3.1 | 12.8 |

EXAMPLE 33

A series of runs was conducted, in each of which DSHMPA was reacted with DSIDA in the presence of a homogeneous ruthenium catalyst. Selection of catalyst, conditions and results of the runs are set forth in Table 20.

TABLE 20

New examples of homogeneous Ru catalysts in the reaction of DSHMPA + DSIDA (100 psi $H_2$)

| No. | Catalyst | Additive | Ratio a:b | Time h | T °C. | IDA Conv % | GI % | Glyphosate % | Total GI + Glyph % |
|---|---|---|---|---|---|---|---|---|---|
| 1 | $K_2RuCl_5(H_2O)$ | | 4:1 | 16 | 200 | 86 | 23.5 | 6.5 | 30.0 |
| 2 | $K_3RuCl_6$ | | 4:1 | 16 | 200 | 64 | 10.3 | 4.6 | 14.9 |
| 3 | $K_3[(RuCl_5)O]$ | | 4.5:1 | 16 | 200 | 73 | 12.0 | 4.3 | 16.3 |
| 4 | $K_4Ru(CN)_6$ | | 4:1 | 16 | 200 | 15 | 0 | 0 | 0 |
| 5 | $K_2RuCl_5(H_2O)$ | $HCOONH_4$ | 4:1 | 16 | 200 | 82 | 13.1 | 6.0 | 19.1 |
| 6 | $K_2RuCl_5(H_2O)$ | 2,6-dicarboxypyridine | 4:1 | 16 | 200 | 85 | 5.4 | 2.8 | 8.2 |

EXAMPLE 34

A series of runs was conducted in which HMPA was reacted with either DSIDA, glyphosate, or PMIDA ("GI") was the amine substrate. In all but one of these runs a 5% Ru/C catalyst was used. In one run, a $RuCl_3$ homogeneous catalyst was employed. Conditions of the reaction and conversions are shown in Table 21.

TABLE 21

Thermal stability of starting materials and products in catalytic reactions of DSHMPA and DSIDA or glyphosate

| No. | Aminoacid | Catalyst | pH (start) | T, h | t, C. | Conversion % |
|---|---|---|---|---|---|---|
| 7 | GI | 5% Ru/C | 9 | 16 | 200 | 42 |
| 8 | GI | 5% Ru/C | 9 | 16 | 200 | 6* |
| 9 | IDA | 5% Ru/C | 7 | 16 | 200 | 53 |
| 10 | DSIDA | 5% Ru/C | 10 | 16 | 200 | 64 |
| 11 | Glyphosate | 5% Ru/C | 9.3 | 16 | 175 | 40 |
| 12 | Glyphosate | 5% Ru/C | 9.3 | 20 | 200 | 64 |
| 13 | Glyphosate | 5% Ru/C | 10 | 16 | 200 | 80 |
| 14 | Glycine** | $RuCl_3$ | 9 | 16 | 150 | 84 |
| 15 | Glycine** | 5% Ru/C | 9 | 16 | 150 | 69 |
| 16 | Glycine** | 5% Ru/C | 9 | 16 | 175 | 95 |
| 17 | Glycine** | 5% Ru/C | 10 | 16 | 200 | 98 |
| 18 | Glycine** | 5% Ru/C | 7 | 16 | 200 | 94 |

*In the presence of 4 eq DSHMPA;
**Sodium salt.

EXAMPLE 35

A series of runs was conducted testing the effect of certain complex ions on the reaction between CMPA and glycine. The conditions of the reactions and results are shown in Table 22.

TABLE 22

Influence of Some Complex Ions on Reactions of CMPA and Glycine (Molar Ratio CMPA:Glycine 1:1, T, 18 hours, t, 75°C.)

| Run | Base Catalyst | CMPA Conversion % | Glyphosate Yield % | Glyphosine Yield % | HMPA Yield % | Method |
|---|---|---|---|---|---|---|
| 18 | 3eq NaOH none | 62.6 | 38.5 | 19.9 | 5.2 | NMR |
| 19 | 3eq NaOH $K_2Zn(CN)_6$ | 54.8 | 34.3 | 15.7 | 4.8 | NMR |
| 20 | 3eq NaOH | 53.6 | 34.2 | 14.6 | 4.7 | NMR |
| 21 | 3eq NaOH $K_4Ru(CN)_6$ | 71.2 | 34.9 | 20.7 | 5.1 | NMR 10% of $PO_4$ was detected |
| 22 | 3eq NaOH $K_2Pt(CN)_6$ | 60.1 | 37.4 | 17.5 | 5.3 | NMR |
| 23 | 3eq NaOH $K_2Pt(CN)_4$ | 63.0 | 38.0 | 19.0 | 6.0 | NMR |

What is claimed is:

1. A process for the preparation of a product corresponding to the formula:

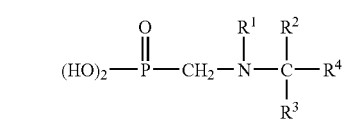

Formula I or a phosphonic acid ester or salt thereof, wherein $R^1$ is selected from the group consisting of substituted or unsubstituted alkyl, alkynyl, aryl, aralkyl, aralkenyl or aralkynyl, $R^2$ and $R^3$ are independently selected from the group consisting of hydrogen, nitro, cyano and substituted or unsubstituted alkyl, alkenyl, alkynyl, aryl, aralkyl, aralkenyl or aralkynyl and $R^4$ is selected from the group consisting of cyano and a substituent corresponding to the formula:

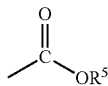

wherein $R^5$ is hydrogen or a moiety forming a carboxylate salt or ester, the process comprising:

contacting a halomethylphosphonic acid reactant with an amine reactant, said halomethylphosphonic acid reactant comprising halomethylphosphonic acid, a halomethylphosphonic acid salt halomethylphosphonic acid ester, or mixtures thereof, said amine reactant comprising a compound corresponding to the formula:

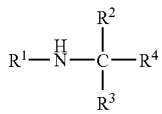

wherein $R^1$, $R^2$, $R^3$ and $R^4$ are as defined above, or a dimer, oligomer or polymer of a compound of Formula III in which $R^4$ corresponds to Formula II.

2. A process as set forth in claim 1 wherein said halomethylphosphonic acid reactant and said amine reactant are contacted in a ratio of no more than about 3 moles of said amine reactant per mole of halomethylphosphonic acid.

3. A process as set forth in claim 1 wherein said halomethylphosphonic acid reactant and said amine reactant are contacted in a ratio of no more than about 2.0 moles of said amine reactant per mole of halomethylphosphonic acid.

4. A process as set forth in claim 1 wherein said halomethylphosphonic acid reactant and said amine reactant are contacted in a ratio of no more than about 1.5 moles of said amine reactant per mole of halomethylphosphonic acid.

5. A process as set forth in claim 1 wherein said halomethylphosphonic acid reactant and said amine reactant are contacted in a ratio of no more than about 1.25 moles of said amine reactant per mole of halomethylphosphonic acid.

6. A process as set forth in claim 1 wherein said halomethylphosphonic acid reactant and said amine reactant are contacted in a ratio of no more than about 1.1 moles of said amine reactant per mole of halomethylphosphonic acid.

7. A process as set forth in claim 1 wherein said halomethylphosphonic acid reactant and said amine reactant are contacted in substantially equivalent proportions.

8. A process as set forth in claim 1 wherein said compound of Formula I is contacted with molecular oxygen in the presence of a noble metal on carbon catalyst.

9. A process as set forth in claim 8 wherein the noble metal catalyst comprises a metal selected from the group consisting of platinum and palladium.

10. A process as set forth in claim 8 wherein the noble metal catalyst is protected from contamination by halide anions.

11. A process as set forth in claim 1 wherein $R^1$ is selected from the group consisting of methyl and propyl.

12. A process as set forth in claim 1 wherein said halomethylphosphonic acid or a salt thereof is contacted with said amine reactant in an aqueous alkaline medium.

13. A process for producing a substantially anhydrous dimeric, trimeric or oligomeric self ester of hydroxymethylphosphonic acid, the process comprising heating hydroxymethylphosphonic acid at a temperature between about 100° and about 200° C. and a pressure between about 1 and about 70 mm Hg in the presence of an organic solvent, said organic solvent being characterized by forming an azeotrope with water at a temperature between about 100° and about 170° C.

14. A process for the preparation of a product corresponding to the formula Ia:

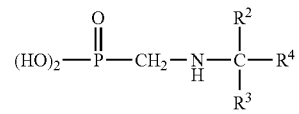

wherein $R^2$ and $R^3$ are independently selected from the group consisting of hydrogen, nitro, cyano and substituted or unsubstituted alkyl, alkenyl, alkynyl, aryl, aralkyl, aralkenyl or aralkynyl and $R^4$ is selected from the group consisting of cyano and a substituent corresponding to the formula:

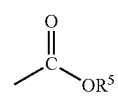

wherein $R^5$ is hydrogen or a moiety forming a carboxylate salt or ester, the process comprising:

contacting a halomethylphosphonic acid reactant with an amine reactant, said halomethylphosphonic acid reactant comprising halomethylphosphonic acid, a halomethylphosphonic acid salt halomethylphosphonic acid ester, or mixtures thereof, said amine reactant comprising a compound corresponding to the formula:

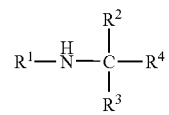

wherein $R^1$ is selected from the group consisting of substituted or unsubstituted alkyl, alkynyl, aryl, aralkyl, aralkenyl or aralkynyl, $R^2$, $R^3$ and $R^4$ are as defined above and/or a dimer, oligomer or polymer of a compound of Formula III in which $R^4$ corresponds to Formula II, thereby producing an intermediate product of Formula I:

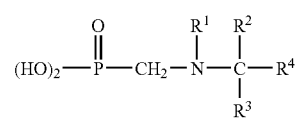

wherein $R^1$, $R^2$, $R^3$, and $R^4$ are as defined above; and
contacting said compound of Formula I with an oxidizing agent in the presence of a catalyst thereby removing substituent $R^1$ and producing a compound of Formula Ia.

15. A process set forth in claim 14 wherein $R^2$ and $R^3$ are each hydrogen and $R^4$ corresponds to Formula II.

16. A process as set forth in claim 15 wherein $R^1$ is selected from the group consisting of alkyl and carboxymethyl.

17. A process as set forth in claim 16 wherein $R^1$ is selected from the group consisting of methyl and carboxymethyl.

18. A process as set forth in claim 14 wherein said halomethylphosphonic acid reactant and said amine reactant are contacted in substantially equivalent proportions.

19. A process for the preparation of a product corresponding to the formula:

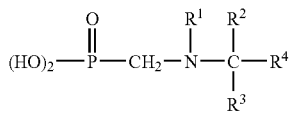

Formula I or a phosphonic acid ester or salt thereof, wherein $R^1$ is selected from the group consisting of substituted or unsubstituted alkyl, alkynyl, aryl, aralkyl, aralkenyl or aralkynyl, $R^2$ and $R^3$ are independently selected from the group consisting of hydrogen, nitro, cyano and substituted or unsubstituted alkyl, alkenyl, alkynyl, aryl, aralkyl, aralkenyl or aralkynyl and $R^4$ is selected from the group consisting of cyano and a substituent corresponding to the formula:

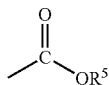

Formula II wherein $R^5$ is hydrogen or a moiety forming a carboxylate salt or ester, the process comprising:

contacting a halomethylphosphonic acid reactant with an amine reactant in an aqueous reaction medium, wherein said halomethylphosphonic acid reactant comprises halomethylphosphonic acid, a halomethylphosphonic acid salt halomethylphosphonic acid ester, or mixtures thereof, said amine reactant comprising a compound corresponding to the formula:

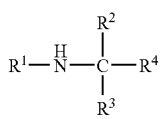

Formula III wherein $R^1$, $R^2$, $R^3$ and $R^4$ are as defined above, or a dimer, oligomer or polymer of a compound of Formula III in which $R^4$ corresponds to Formula II; and wherein said aqueous reaction medium comprises at least about 25 moles of water per mole halomethylphosphonic acid.

20. The process of claim 19 wherein said aqueous reaction medium comprises at least about 40 moles of water per mole halomethylphosphonic acid.

21. The process of claim 19 wherein said halomethylphosphonic acid reactant and said amine reactant are contacted in substantially equivalent proportions.

22. The process of claim 20 wherein said halomethylphosphonic acid reactant and said amine reactant are contacted in substantially equivalent proportions.

23. A process as set forth in claim 1 wherein the reactants are contacted in the presence of catalyst.

24. A process as set forth claim 1 wherein the catalyst comprises copper.

25. A process as set forth in claim 1 wherein the amine reactant comprises iminodiacetic acid.

26. A process as set forth in claim 1 wherein the halomethylphosphonic acid comprises chloromethylphosphonic acid.

27. A process as set forth in claim 1 wherein $R^1$ is alkyl.

28. A process as set forth in claim 1 wherein $R^1$ is methyl.

29. A process as set forth in claim 14 wherein said compound of Formula I is contacted with molecular oxygen in the presence of a noble metal catalyst.

30. A process as set forth in claim 20 wherein the noble metal catalyst comprises a metal selected from the group consisting of platinum, palladium, rhodium, iridium, osmium, and gold.

31. A process as set forth in claim 20 wherein the noble metal catalyst comprises a metal selected from the group consisting of platinum and palladium.

32. A process as set forth in claim 29 wherein the noble metal catalyst comprises platinum.

33. A process as set forth in claim 29 wherein the noble metal catalyst is unsupported.

34. A process as set forth in claim 29 wherein the noble metal catalyst comprises a support selected from the group consisting of carbon, alumina, silica, titania, zirconia, siloxane, and barium sulfate.

35. A process as set forth in claim 29 wherein the noble metal catalyst comprises a support selected from the group consisting of graphite, polyamide, polyimide, polycarbonate, polyurea, and polyester.

36. A process as set forth in claim 29 wherein the noble metal catalyst comprises a carbon support.

37. A process as set forth in claim 29 wherein the noble metal catalyst further comprises a promoter selected from the group consisting of tin, cadmium, magnesium, manganese, nickel, aluminum, cobalt, bismuth, lead, titanium, antimony, selenium, iron, rhenium, zinc, cerium, and zirconium.

38. A process as set forth in claim 29 wherein the noble metal catalyst further comprises a promoter selected from the group consisting of bismuth, iron, tin, and titanium.

39. A process as set forth in claim 14 wherein $R^2$ and $R^3$ are hydrogen and $R^4$ is the substituent corresponding to the formula:

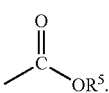

Formula II

* * * * *

UNITED STATES PATENT AND TRADEMARK OFFICE
CERTIFICATE OF CORRECTION

| | | |
|---|---|---|
| PATENT NO. | : 7,750,180 B2 | Page 1 of 1 |
| APPLICATION NO. | : 10/924265 | |
| DATED | : July 6, 2010 | |
| INVENTOR(S) | : James P. Coleman et al. | |

It is certified that error appears in the above-identified patent and that said Letters Patent is hereby corrected as shown below:

Column 72, Claim 24, Line 9: "claim 1" should read -- claim 23 --.

Column 72, Claim 30, Line 20: "claim 20" should read -- claim 29 --.

Column 72, Claim 31, Line 24: "claim 20" should read -- claim 29 --.

Signed and Sealed this
Twenty-fifth Day of January, 2011

David J. Kappos
*Director of the United States Patent and Trademark Office*